(12) United States Patent
Cai et al.

(10) Patent No.: US 11,547,703 B2
(45) Date of Patent: Jan. 10, 2023

(54) SUBSTITUTED FUSED HETEROAROMATIC TRICYCLIC COMPOUNDS AS KINASE INHIBITORS AND THE USE THEREOF

(71) Applicant: IMPACT THERAPEUTICS (SHANGHAI), INC, Shanghai (CN)

(72) Inventors: Suixiong Cai, Shanghai (CN); Ye Edward Tian, Shanghai (CN); Xiaozhu Wang, Jiangsu (CN)

(73) Assignee: IMPACT THERAPEUTICS (SHANGHAI), INC, Shanghai (CN)

( * ) Notice: Subject to any disclaimer, the term of this patent is extended or adjusted under 35 U.S.C. 154(b) by 684 days.

(21) Appl. No.: 16/488,884

(22) PCT Filed: Feb. 26, 2018

(86) PCT No.: PCT/CN2018/077188
§ 371 (c)(1),
(2) Date: Aug. 26, 2019

(87) PCT Pub. No.: WO2018/153365
PCT Pub. Date: Aug. 30, 2018

(65) Prior Publication Data
US 2021/0128535 A1 May 6, 2021

(30) Foreign Application Priority Data
Feb. 27, 2017 (CN) .......................... 201710106900.8

(51) Int. Cl.
| | | |
|---|---|---|
| *A61K 31/444* | (2006.01) |
| *A61P 35/00* | (2006.01) |
| *A61K 33/243* | (2019.01) |
| *A61K 31/167* | (2006.01) |
| *A61K 31/282* | (2006.01) |
| *A61K 31/337* | (2006.01) |
| *A61K 31/436* | (2006.01) |
| *A61K 31/437* | (2006.01) |
| *A61K 31/4545* | (2006.01) |
| *A61K 31/475* | (2006.01) |
| *A61K 31/496* | (2006.01) |
| *A61K 31/4985* | (2006.01) |
| *A61K 31/5025* | (2006.01) |
| *A61K 31/519* | (2006.01) |
| *A61K 31/5377* | (2006.01) |
| *A61K 31/635* | (2006.01) |
| *A61K 31/675* | (2006.01) |
| *A61K 38/31* | (2006.01) |
| *A61K 39/395* | (2006.01) |
| *C07D 471/04* | (2006.01) |
| *C07D 471/14* | (2006.01) |
| *C07D 487/04* | (2006.01) |
| *C07D 487/14* | (2006.01) |

(52) U.S. Cl.
CPC .......... *A61K 31/444* (2013.01); *A61K 31/167* (2013.01); *A61K 31/282* (2013.01); *A61K 31/337* (2013.01); *A61K 31/436* (2013.01); *A61K 31/437* (2013.01); *A61K 31/4545* (2013.01); *A61K 31/475* (2013.01); *A61K 31/496* (2013.01); *A61K 31/4985* (2013.01); *A61K 31/5025* (2013.01); *A61K 31/519* (2013.01); *A61K 31/5377* (2013.01); *A61K 31/635* (2013.01); *A61K 31/675* (2013.01); *A61K 33/243* (2019.01); *A61K 38/31* (2013.01); *A61K 39/3955* (2013.01); *A61P 35/00* (2018.01); *C07D 471/04* (2013.01); *C07D 471/14* (2013.01); *C07D 487/04* (2013.01); *C07D 487/14* (2013.01)

(58) Field of Classification Search
CPC .. C07D 471/04; C07D 471/14; C07D 487/04; C07D 487/14
See application file for complete search history.

(56) References Cited

FOREIGN PATENT DOCUMENTS

| WO | WO 2005016919 A1 | 2/2005 |
|---|---|---|
| WO | WO 2006085067 A1 | 8/2006 |
| WO | WO 2015/170081 A1 | 11/2015 |
| WO | WO 2016155884 A1 | 10/2016 |

OTHER PUBLICATIONS

Rida ("Benzimidazole condensed ring system. 1. Syntheses and biological investigations of some substituted pyrido[1,2a] benzimidazoles" J. Heterocycl. Chem., 25(4), 1988, p. 1087-1093) (Year: 1988).*

(Continued)

*Primary Examiner* — Amy C Bonaparte
(74) *Attorney, Agent, or Firm* — Sterne, Kessler, Goldstein & Fox P.L.L.C.

(57) ABSTRACT

The disclosure relates to substituted fused heteroaromatic tricyclic compounds and the use thereof. Specifically, the disclosure provides compounds of the following Formula I:

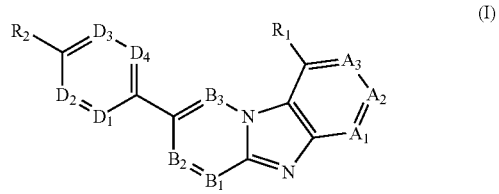

(I)

or a pharmaceutically acceptable salt or prodrug thereof, wherein $A_1$-$A_3$, $B_1$-$B_3$, $D_1$-$D_4$ and $R_1$-$R_2$ are defined herein. Compounds having Formula I are ATM kinase inhibitors. Therefore, compounds of the disclosure may be used to treat clinical conditions caused by DDR functional defects, such as cancer.

20 Claims, No Drawings

(56) References Cited

OTHER PUBLICATIONS

Gonzales ("Generation of tricyclic imidazo[1,2-a]pyrazines as novel PI3K inihibitors by application of a conformation restriction strategy" Bioorganic and Medicinal Chemistry Letters 27, 2017, p. 2536-2543) (Year: 2017).*
Demirayak, S., et al., "Synthesis and anticancer and anti-HIV testing of some pyrazino[1,2-α]benzimidazole derivatives," *European Journal of Medicinal Chemistry* 37: 255-260, Elsevier SAS, Netherlands (2002).
International Search Report for International Application No. PCT/CN2018/077188, State Intellectual Property Office of the P.R. China, Beijing, dated Jun. 5, 2018, 2 pages.
Meric, A., et al., "Synthesis of Some 2,4-Di- and 2,3,4-Trisubstituted Benzimidazo[1,2-a]Pyrimidines and Evaluation of Their Cytotoxicities Towards F2408 and 5RP7 Cells," *Rev. Chim. (Bucuresti)* 57(11): 1090-1097, Chiminform Data SA, Romania (2006).

* cited by examiner

SUBSTITUTED FUSED HETEROAROMATIC TRICYCLIC COMPOUNDS AS KINASE INHIBITORS AND THE USE THEREOF

FIELD OF THE DISCLOSURE

This disclosure is in the field of medicinal chemistry. In particular, the disclosure relates to substituted fused heteroaromatic tricyclic compounds, and the use of these compounds as kinase inhibitors, including ATM protein kinase inhibitors.

RELATED ART

Mammalian cells encounter many external and internal challenges that cause DNA damage every day, including mutations in DNA bases. These mutations cause changes in cell function, including the occurrence of malignant tumors, even directly cause cell death. Therefore, mammalian cells have evolved a sophisticated DNA damage response (DDR) mechanism to address these challenges. This mechanism detects and repairs DNA damage by short cell cycle pauses to ensure genome stability and cell survival.

The occurrence of DDR and cancer has an inextricable relationship. Scientific research has found that deficiencies in DDR repair mechanisms can lead to cancer at multiple levels, such as base mutations in the DDR gene have been found to cause a variety of cancers, including breast cancer and ovarian cancer in women with base mutations in the BRCA1 or BRCA2 gene, which are much higher than in people without mutations. BRCA1 and BRCA2 are important components of DDR to repair DNA double-strand breaks based on homologous recombination. Studies have also found deletions or loss of function of key proteins in DDR cells of various malignant tumors or regulate the cell cycle, including p53, ATM, ATR, BRCA1/2 and so on.

In recent years, with the development of science and understanding of the mechanism of cell DDR, there has been great interest in the development of novel anticancer targeted therapeutic drugs for the mutation and loss of function of DDR constituent proteins. For example, PARP inhibitors can specifically kill cancer cells with BRCA1/2 mutations by inhibiting the single-strand repair mechanism of DNA damage. This mechanism of action is called synthetic lethality.

ATM kinase is one of the important constituent proteins of DDR and belongs to the PI3K related serine/threonine kinase family. ATM kinase gene was cloned when the telangiectasia ataxia syndrome was studied in 1995. ATM gene is located on human chromosome 11q22-23 and is a coding sequence comprising 66 exons and 9168 bases. ATM kinase is a large protein with a molecular weight of approximately 350 kDa. ATM kinase is one of the important components of DDR. ATM kinase is activated when DNA damage causes double-strand breaks. Its function is to achieve cell cycle transition point pause by phosphorylation of downstream proteins, repairing damaged DNA by homologous recombination or entering apoptotic mechanism (Weber and Ryan, 2016).

ATM kinase signal transduction can be roughly divided into two mechanisms: the typical mechanism is activated by DNA double-strand breaks. When DNA double-strand breaks are detected, the ATM kinase is transported to the breaking site and activated. Although the detailed activation mechanism is not well understood, the activation process includes from homodimers into active monomers (Bakkenist et al., 2003), self-phosphorylation of Ser1981 site and other sites, and acetylation. Activated ATM kinase further phosphorylates downstream substrates, including cell cycle checkpoint proteins (such as Chk1 and Chk2), DNA repair proteins (BRCA1 and RAD51), or apoptotic pathway proteins (p53). Studies have shown that there are more than 700 proteins phosphorylated after DNA double-strand breaks (Choi, Kipps and Kurzrock, 2016). In addition, ATM is involved in functions that are not directly related to DNA damage, such as metabolism, stress, etc. These functions are often referred to as atypical mechanisms (Cremona et al., 2013).

The development of new anticancer drugs targeting ATM kinase mainly depends on two considerations. Radiotherapy or cytotoxic chemotherapeutics, such as topoisomerase inhibitors and DNA methylation drugs, etc., which are usually toxic to rapidly differentiated cancer cells based on DNA damage, are greatly reduced in cytotoxicity due to the presence of DDR. Therefore, ATM inhibitors, combined with inhibitors that inhibit the function of DDR constituent proteins, such as PARP inhibitors, can greatly enhance the efficacy of these drugs. Studies by Gilardini Montani M S et al. (J Exp Clin Cancer Res, 2013, 32:95) have shown that reducing ATM expression could enhance the sensitivity of breast cancer cells to PARP inhibitors, which provided a theoretical basis for the possibility of combination of ATM inhibitors and PARP inhibitors in the treatment of breast cancer. In addition, Kubota E et al. (Cell Cycle, 2014, 13 (13): 2129-2137) found that the expression of ATM protein in gastric cancer cells was significantly correlated with the sensitivity of PARP inhibitor olaparib. The use of small-molecule ATM inhibitors enhances the sensitivity of p53-inactivated gastric cancer cells to olaparib. Therefore, the combined use of ATM inhibitors and PARP inhibitors may be used to treat gastric cancer. In addition, for cancer cells with DDR deficiency, ATM kinase inhibitors can be used alone by synthesizing lethal mechanism and targeted anticancer drugs can be developed for specific patients, which have the characteristics of good efficacy and low toxicity.

Degorce S L et al. (J Med Chem, 2016, 59: 6281-6292) reported a series of 3-quinolinformamides as ATM kinase inhibitors, and observed good efficacy of ATM kinase inhibitors combined with irinotecan in animal model.

Sk. Rasheed et al. (J. Org. Chem., 2015, 80: 9321-9327) reported a Cu(II)-catalyzed, inter/intramolecular C—N bond formation for the synthesis of various benzimidazole-fused heterocycles. The robustness of this reaction is demonstrated by the synthesis of a series of benzimidazole-fused heteroaromatics (e.g., pyrido[1,2-a] benzimidazole, benzimidazo[1,2-a]quinolines, benzimidazo [1,2-a]pyrazine, benzo [4,5] imidazo[2,1-b]thiazoles) directly from 2-aminoheteroarenens and 2-iodoarylboronic acids in one-pot. The novel cascade protocol for C—N bond formation operates via unique combination of Chan-Lam type coupling followed by Ullmann-type reaction.

SUMMARY OF THE DISCLOSURE

The disclosure provides novel substituted fused heteroaromatic tricyclic compounds, as represented in Formulae I and II as kinase inhibitors, especially ATM kinase inhibitors.

The present disclosure also provides pharmaceutical compositions comprising a compound of Formula I or II in an effective amount for the treatment of cancer.

In a concrete embodiment, the pharmaceutical composition useful for the treatment of cancer may also contain one or more pharmaceutically acceptable carriers or diluents.

In a concrete embodiment, the pharmaceutical composition useful for the treatment of cancer may also contain at least one known anticancer drugs or its pharmaceutically acceptable salts.

The disclosure is also directed to methods for the preparation of novel compounds of Formula I or II.

DETAILED DESCRIPTION OF THE DISCLOSURE

The disclosure finds novel substituted fused heteroaromatic compounds as kinase inhibitors, including ATM kinase inhibitors, as represented in Formula I.

Specifically, compounds of the present disclosure are represented by Formula I:

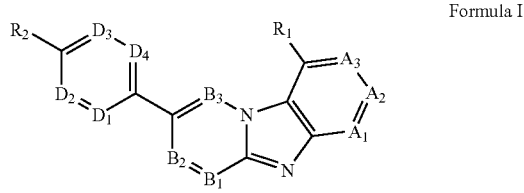

Formula I or pharmaceutically acceptable salts or prodrugs thereof, wherein:

$A_1$-$A_3$ each are independently N or CR';

$B_1$-$B_3$ each are independently N or CR";

$D_1$-$D_4$ each are independently N or CR'";

$R_1$ is H, optionally substituted alkyl, optionally substituted oxy group, optionally substituted amino, optionally substituted carbocyclic group, optionally substituted heterocyclic group, optionally substituted aryl, optionally substituted heterocyclic oxy group or optionally substituted heteroaryl;

$R_2$ is H, optionally substituted alkoxy, optionally substituted amino, optionally substituted carbocyclic group, optionally substituted hetercyclic group, optionally substituted aryl or optionally substituted heteroaryl;

R', R" and R'" each are independently H, halo, optionally substituted amino, optionally substituted alkoxy, optionally substituted C1-10 alkyl (e.g. haloalkyl, hydroxyalkyl, aminoalkyl, carboxyalkyl), alkenyl, alkynyl, nitro, cyano, acylamido, hydroxy, thiol, acyloxy, azido, carboxy, ethylenedioxo, hydroxyacylamido or optionally substituted alkylthiol.

In one or more embodiment, in compound of Formula I, the ring including $A_1$-$A_3$ is phenyl or pyridyl.

In one or more of the foregoing embodiments, in compound of Formula I, the ring including $B_1$-$B_3$ is pyridyl, pyrimidinyl, pyrazinyl or pyradazinyl.

In one or more of the foregoing embodiments, in compound of Formula I, R', R" and R'" are H.

In one or more of the foregoing embodiments, in compound of Formula I, $A_1$-$A_3$ are all CH. In some embodiments, $A_1$ is N, $A_2$ and $A_3$ are CH; in some embodiments, $A_1$ and $A_3$ are CH, $A_2$ is N; in some embodiments, $A_1$ and $A_2$ are CH, $A_3$ is N; in some embodiments, $A_1$ and $A_3$ are N, $A_2$ is CH.

In one or more of the foregoing embodiments, in compound of Formula I, $B_1$-$B_3$ are all CH. In some embodiments, $B_1$ is N, $B_2$ and $B_3$ are CH; in some embodiments, $B_1$ and $B_3$ are CH, $B_2$ is N; in some embodiments, $B_1$ and $B_2$ are CH, $B_3$ is N.

In one or more of the foregoing embodiments, in compound of Formula I, the ring including $A_1$-$A_3$, imidazolyl ring and the ring including $B_1$-$B_3$ are fused to benzo[4,5]imidazo[1,2-a]pyridinyl, benzo[4,5]imidazo[1,2-a]pyrimidinyl, benzo[4,5]imidazo[1,2-a]pyrazinyl, benzo[4,5]imidazo[1,2-b]pyridazinyl, imidazo[1,2-a:4,5-c']dipyridinyl or imidazo[1,2-a: 5,4-c']dipyridinyl.

In one or more of the foregoing embodiments, in compound of Formula I, the substituent on $R_1$ is selected from the group consisting of $C_{1-6}$ alkyl, heterocyclic, aryl, heteroaryl and —$NR_3R_4$ groups, wherein the number of the substituents is 1-4, and $R_3$ and $R_4$ are independently selected from H and $C_{1-6}$ alkyl groups. In certain embodiments, $R_1$ is an optionally substituted alkyl, oxy group, amino, heterocyclic group, aryl group or heteroaryl group, wherein the substituent on the alkyl group, oxy group and amino group may be one heterocyclic group such as tetrahydrofuryl, tetrahydropyranyl, pyranyl, piperidyl, piperazinyl, pyrrolidinyl, imidazolidinyl, imidazolinyl, dihydroindolyl, dihydroisoindolyl, morpholinyl, pyrazolidinyl, pyrazolinyl and the like; the substituents on the heterocyclic group, aryl group and heteroaryl group may be 1-4 substituents selected from $C_{1-6}$ alkyl and —$NR_3R_4$ groups.

In one or more of the foregoing embodiments, in compound of Formula I, $R_1$ is selected from the group consisting of dihydropyranyl; tetrahydropyranyl; piperidyl that is not substituted or optionally substituted with 1-4 $C_{1-6}$ alkyl or —$NR_3R_4$ groups; morpholinyl; imidazolyl; piperazinyl that is optionally substituted with 1-4 $C_{1-6}$ alkyl groups; or $C_{1-6}$ alkyl or amino or oxy group that is optionally substituted with a heterocyclic group (tetrahydrofuryl, tetrahydropyranyl, pyranyl, piperidyl, piperazinyl, pyrrolidinyl, imidazolidinyl, imidazolinyl, dihydroindolyl, dihydroisoindolyl, morpholinyl, pyrazolidinyl and pyrazolinyl, etc, wherein said heterocyclic group can be optionally substituted by 1-3 $C_{1-6}$ alkyl); wherein $R_3$ and $R_4$ are independently selected from H and $C_{1-6}$ alkyl groups. In certain embodiments, in compound of Formula I, $R_1$ is selected from the group consisting of dihydropyranyl that is not substituted or optionally substituted with 1-2 $C_{1-4}$ alkyl groups, tetrahydropyranyl, piperidyl that is not substituted or optionally substituted with —$NR_3R_4$ or 1-2 $C_{1-4}$ alkyl groups, morpholinyl that is not substituted or optionally substituted with 1-2 $C_{1-4}$ alkyl groups, and piperazinyl that is optionally substituted with 1-3 $C_{1-4}$ alkyl groups (preferably, piperazinyl is connected to rings containing $A_1$-$A_3$ by one of the ring N atoms, and at least one of the alkyl substituents is located in para-position). Preferred $R_1$ is selected from optionally substituted heterocyclic groups, including:

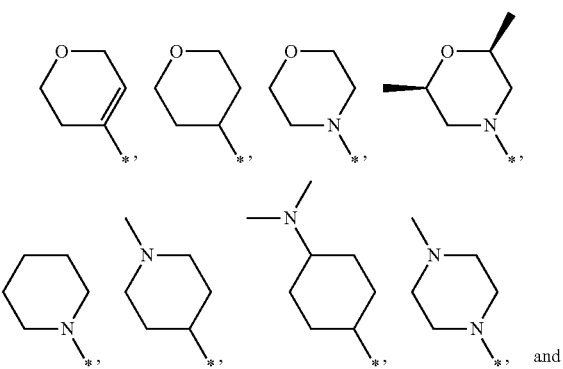

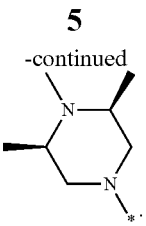

More preferably, $R_1$ is selected from:

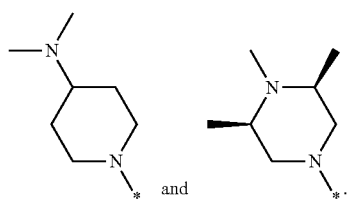

and

In one or more of the foregoing embodiments, in compound of Formula I, the ring comprising $D_1$-$D_4$ is pyridinyl or optionally substituted phenyl. Preferably, the ring comprising $D_1$-$D_4$ in compound of Formula I is optionally substituted phenyl. In some embodiment, the substituents on the ring comprising $D_1$-$D_4$ contain $R'''$ in addition to $R_2$.

In one or more of the foregoing embodiments, in compound of Formula I, $D_1$ is CH, $D_2$ is N, $D_3$ is CH, $D_4$ is CH; in some embodiments, $D_1$ is N, $D_2$ is CH, $D_3$ is CH, $D_4$ is CH; in some embodiments, $D_1$ is CH, $D_2$ is CR', $D_3$ is CH, $D_4$ is CH; wherein preferably, $R'''$ is independently H, halo, and halo $C_{1-4}$ alkyl. More preferably, $R'''$ independently is halo and halo $C_{1-4}$ alkyl.

In one or more of the foregoing embodiments, in compound of Formula I, the substituent on $R_2$ may be selected from the group consisting of —$NR_3R_4$, $C_{1-4}$ alkyl, and $C_{1-6}$ alkyl substituted with —$NR_3R_4$, wherein the number of the substituents is 1-4, and $R_3$ and $R_4$ are independently selected from H and $C_{1-6}$ alkyl groups.

In one or more of the foregoing embodiments, in compound of Formula I, $R_2$ is selected from the group consisting of H, —$NR_3R_4$, $C_{1-6}$ alkoxyl optionally substituted with —$NR_3R_4$, $C_{1-6}$ alkyl-NH— optionally substituted with —$NR_3R_4$, $C_{1-6}$ alkyl-$NHR_3$— optionally substituted with —$NR_3R_4$, piperazinyl optionally substituted with 1-3 $C_{1-4}$ alkyl groups, piperidyl optionally substituted with —$NR_3R_4$, and $C_{3-8}$ cycloalkyl optionally substituted with —$NR_3R_4$; wherein, $R_3$ and $R_4$ are independently selected from H or $C_{1-6}$ alkyl groups. In preferred embodiments, in compound of Formula I, $R_2$ is selected from the group consisting of $C_{1-6}$ alkoxyl optionally substituted with —$NR_3R_4$, piperazinyl optionally substituted with 1-3 $C_{1-4}$ alkyl groups (preferably, piperazinyl is connected to rings containing $D_1$-$D_4$ by one of the ring N atoms, and at least one of the alkyl substituents is located in para-position), piperidyl optionally substituted with —$NR_3R_4$ (preferably, piperidyl is connected to rings containing $D_1$-$D_4$ by one of the ring N atoms, and the —$NR_3R_4$ substituent is located in para-position); wherein, $R_3$ and $R_4$ are independently selected from H or $C_{1-6}$ alkyl groups. Preferred $R_2$ includes:

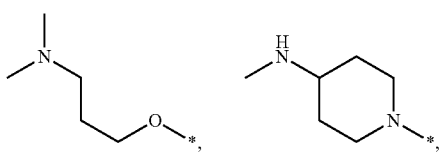

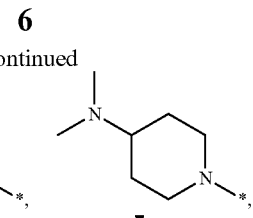

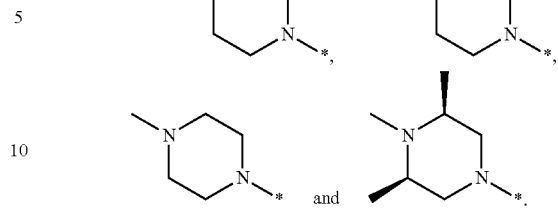

and

More preferably, $R_2$ is selected from:

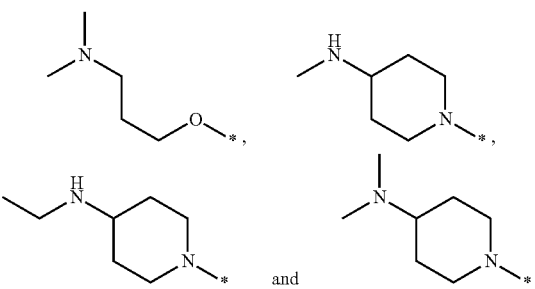

and

One group of preferred compounds of the present disclosure are represented by Formula IIa or IIb (Formula II):

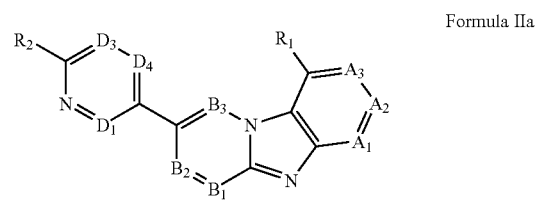

Formula IIa

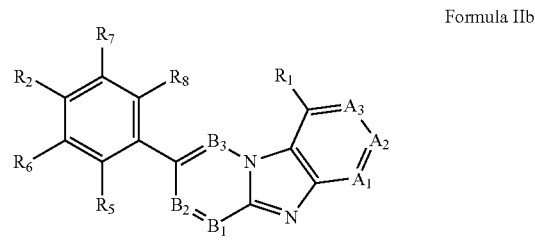

Formula IIb or pharmaceutically acceptable salts or prodrugs thereof, wherein:

$A_1$-$A_3$, $B_1$-$B_3$, $D_1$, $D_3$-$D_4$ and $R_1$-$R_2$ are defined as in Formula I;

in Formula IIIb, $R_5$-$R_8$ are independently hydrogen, halo, optionally substituted amino, optionally substituted alkoxy, optionally substituted $C_{1-10}$ alkyl (e.g. haloalkyl, hydroxyalkyl, aminoalkyl, carboxyalkyl), alkenyl, alkynyl, nitro, cyano, acylamido, hydroxy, thiol, acyloxy, azido, carboxy, ethylenedioxo, hydroxyacylamido or optionally substituted alkylthiol.

In one or more embodiments of compounds of Formulae IIa and IIb, the said $A_1$-$A_3$, $B_1$-$B_3$, $D_1$, $D_3$-$D_4$ and $R_1$-$R_2$ are described in any one of the foregoing embodiments of Formula I.

In one or more of the foregoing embodiments, in compound of Formula IIb, each of $R_5$-$R_8$ is H.

In one or more of the foregoing embodiments, in compound of Formula IIb, $R_6$ is independently H, halo, or halo $C_{1-4}$ alkyl.

In one or more of the foregoing embodiments, in compound of Formula IIb, $R_6$ is halo or halo $C_{1-4}$ alkyl.

In one or more of the foregoing embodiments, in compound of Formula IIa or IIb, $A_1$-$A_3$ is CH. In some embodiments, $A_1$ is N, $A_2$ and $A_3$ is CH; in some embodiments, $A_1$ and $A_3$ are CH, $A_2$ is N; in some embodiments, $A_1$ and $A_2$ are CH, $A_3$ is N; in some embodiments, $A_1$ and $A_3$ are N, $A_2$ is CH.

In one or more of the foregoing embodiments, in compound of Formula IIa or IIb, $B_1$-$B_3$ is CH. In some embodiments, $B_1$ is N, $B_2$ and $B_3$ are CH; in some embodiments, $B_1$ and $B_3$ are CH, $B_2$ is N; in some embodiments, $B_1$ and $B_2$ is CH, $B_3$ is N.

In one or more of the foregoing embodiments, in compound of Formula IIa or III), R'" is H.

In one or more of the foregoing embodiments, in compound of Formula IIa or IIb, the ring including $B_1$-$B_3$ is pyridyl, pyrimidinyl, pyrazinyl or pyradazinyl. Preferably, the said ring including $B_1$-$B_3$ is pyridyl.

In one or more of the foregoing embodiments, in compound of Formula IIa or IIb, the ring including $A_1$-$A_3$, imidazolyl ring and the ring including $B_1$-$B_3$ are fused to benzo[4,5]imidazo[1,2-a]pyridinyl, benzo[4,5]imidazo[1,2-a]pyrimidinyl, benzo[4,5]imidazo[1,2-a]pyrazinyl, benzo[4,5]imidazo[1,2-b]pyridazinyl, imidazo[1,2-a:4,5-c']dipyridinyl or imidazo[1,2-a:5,4-c']dipyridinyl. In preferred embodiments, the ring including $A_1$-$A_3$, imidazolyl ring and the ring including $B_1$-$B_3$ are fused to benzo[4,5]imidazo[1,2-a]pyridinyl.

In one or more of the foregoing embodiments, in compound of Formula IIa or IIb, $R_1$ is selected from the group consisting of dihydropyranyl; tetrahydropyranyl; piperidyl that is not substituted or optionally substituted with 1-4 $C_{1-6}$ alkyl or —$NR_3R_4$ groups; morpholinyl; imidazolyl; piperazinyl that is optionally substituted with 1-4 $C_{1-6}$ alkyl groups; or $C_{1-6}$ alkyl or amino or oxy group that is optionally substituted with a heterocyclic group (tetrahydrofuryl, tetrahydropyranyl, pyranyl, piperidyl, piperazinyl, pyrrolidinyl, imidazolidinyl, imidazolinyl, dihydroindolyl, dihydroisoindolyl, morpholinyl, pyrazolidinyl and pyrazolidinyl, etc, wherein said heterocyclic group can be optionally substituted by 1-3 $C_{1-6}$ alkyl); wherein $R_3$ and $R_4$ are independently selected from H or $C_{1-6}$ alkyl groups. In certain embodiments, in compound of Formula I, $R_1$ is selected from the group consisting of dihydropyranyl that is not substituted or optionally substituted with 1-2 $C_{1-4}$ alkyl groups, tetrahydropyranyl, piperidyl that is not substituted or optionally substituted with —$NR_3R_4$ or 1-2 $C_{1-4}$ alkyl groups, morpholinyl that is not substituted or optionally substituted with 1-2 $C_{1-4}$ alkyl groups, and piperazinyl that is optionally substituted with 1-3 $C_{1-4}$ alkyl groups (preferably, piperazinyl is connected to rings containing $A_1$-$A_3$ by one of the ring N atoms, and at least one of the alkyl substituents is located in para-position). Preferred $R_1$ is selected from optionally substituted heterocyclic groups, including:

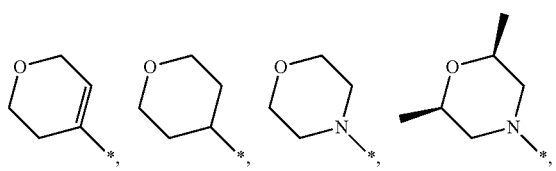

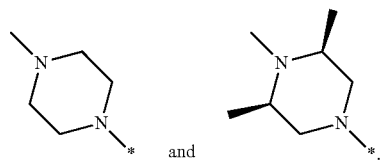

More preferably, $R_1$ is selected from:

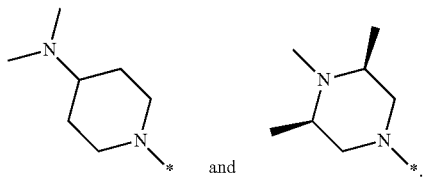

In one or more of the foregoing embodiments, in compound of Formula IIa, the ring including $D_1$ and $D_3$-$D_4$ is an optionally substituted pyridyl ring. It should be understood herein the substituents on the ring comprising $D_1$ and $D_3$-$D_4$ contain R'" in addition to $R_2$. Preferred R'" is selected from the group of H, halo, $C_{1-4}$ alkyl and halo $C_{1-4}$ alkyl.

In one or more of the foregoing embodiments, in compound of Formula IIa or IIb, $R_2$ is selected from the group consisting of $C_{1-6}$ alkoxyl optionally substituted with —$NR_3R_4$, piperazinyl optionally substituted with 1-3 $C_{1-4}$ alkyl groups (preferably, piperazinyl is connected to rings containing $D_1$-$D_4$ by one of the ring N atoms, and at least one of the alkyl substituents is located in para-position), piperidyl optionally substituted with —$NR_3R_4$ (preferably, piperidyl is connected to rings containing $D_1$-$D_4$ by one of the ring N atoms, and the —$NR_3R_4$ substituent is located in para-position); wherein, $R_3$ and $R_4$ are independently selected from H or $C_{1-6}$ alkyl groups. Preferred $R_2$ includes:

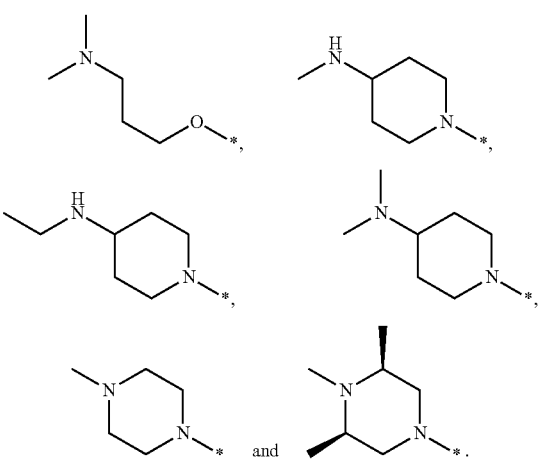

More preferably, $R_2$ is selected from:

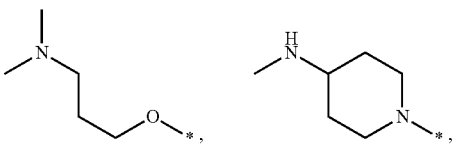

-continued

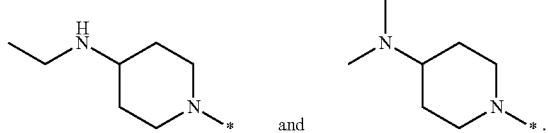

and

In one or more of the foregoing embodiments, in Formulae I, IIa and IIb, the substituents on the ring including $A_1$-$A_3$ are selected from one or more of the said heteroaryl substituents in the present disclosure.

In one or more of the foregoing embodiments, in Formulae I, IIa and IIb, the said alkyl, alkoxy, amino, carbocyclic group, heterocyclic group, aryl or heteroaryl groups for $R_1$ may be substituted with one or more substituents selected from alkyl, alkoxy, amino, carbocyclic group, heterocyclic group, aryl or heteroaryl described in the present disclosure.

In one or more of the foregoing embodiments, in Formulae I, IIa and IIb, the said alkoxy, amino, carbocyclic group, heterocyclic group, aryl or heteroaryl groups for $R_2$ may be substituted with one or more substituents selected from alkoxy, amino, carbocyclic group, heterocyclic group, aryl or heteroaryl described in the present disclosure.

In one or more of the foregoing embodiments, in Formulae I, IIa and IIb, the substituents of said optionally substituted amino, optionally substituted alkoxy, optionally substituted $C_{1-10}$ alkyl and optionally substituted alkylthio for R', R" and R''' are selected from one or more of the amino, alkoxy, alkyl and alkylthio substituents described in the present disclosure.

In one or more of the foregoing embodiments, in Formula IIb, the substituents of said optionally substituted amino, optionally substituted alkoxy, optionally substituted $C_{1-10}$ alkyl and optionally substituted alkylthio substituents for $R_5$-$R_8$ are selected from one or more of the amino, alkoxy, alkyl and alkylthio substituents described in the present disclosure.

In one or more of the foregoing embodiments, in Formula II, an exemplary preferred compound is compound of Formula IIb.

In one or more of the foregoing embodiments, an exemplary preferred compound is compound of Formula IIb, wherein each of $A_1$-$A_3$ is CH; $B_1$-$B_3$ is CH; $R_6$ is H, haloalkyl or halo; $R_5$, $R_7$ and $R_8$ are H; $R_1$ is an optionally substituted heterocyclic group; $R_2$ is an optionally substituted heterocyclic group or $C_{1-6}$ alkoxy substituted with —$NR_3R_4$, wherein $R_3$ and $R_4$ are independently selected from H or $C_{1-6}$ alkyl. More preferably, $R_6$ is $CF_3$, F, Br or Cl; $R_5$, $R_7$ and $R_8$ are H; $R_2$ is the said optionally substituted heterocyclic group or $C_{1-6}$ alkoxy substituted with —$NR_3R_4$.

In one or more of the foregoing embodiments, preferred compounds of Formulae I, IIa and IIb include, without limitation:

N,N-dimethyl-3-((5-(9-(3,6-dihydro-2H-pyran-4-yl)benzo[4,5]imidazo[1,2-a]pyridin-2-yl)pyridin-2-yl)oxy)propan-1-amine (Example 1);
N,N-dimethyl-3-(4-(9-(3,6-dihydro-2H-pyran-4-yl)benzo[4,5]imidazo[1,2-a]pyridin-2-yl)phenoxy)propan-1-amine (Example 2);
N,N-dimethyl-3-(4-(9-(4-methylpiperazin-1-yl)benzo[4,5]imidazo[1,2-a]pyridin-2-yl)phenoxy)propan-1-amine (Example 3);
N,N-dimethyl-3-(4-(9-morpholinobenzo[4,5]imidazo[1,2-a]pyridin-2-yl)phenoxy)propan-1-amine (Example 4);
N,N-dimethyl-3-((5-(9-(piperidin-1-yl)benzo[4,5]imidazo[1,2-a]pyridin-2-yl)pyridin-2-yl)oxy)propan-1-amine (Example 5);
N,N-dimethyl-3-((5-(9-morpholinobenzo[4,5]imidazo[1,2-a]pyridin-2-yl)pyridin-2-yl)oxy)propan-1-amine (Example 6);
N,N-dimethyl-3-((5-(9-(4-methylpiperazin-1-yl)benzo[4,5]imidazo[1,2-a]pyridin-2-yl)pyridin-2-yl)oxy)propan-1-amine (Example 7);
N,N-dimethyl-3-((5-(9-((3S,5R)-3,4,5-trimethylpiperazin-1-yl)benzo[4,5]imidazo[1,2-a]pyridin-2-yl)pyridin-2-yl)oxy)propan-1-amine (Example 8);
N,N-dimethyl-3-((5-(9-(1H-imidazol-1-yl)benzo[4,5]imidazo[1,2-a]pyridin-2-yl)pyridin-2-yl)oxy) propan-1-amine (Example 9);
N,N-dimethyl-3-((5-(9-(morpholinomethyl)benzo[4,5]imidazo[1,2-a]pyridin-2-yl)pyridin-2-yl)oxy)propan-1-amine (Example 10);
N,N-dimethyl-3-((5-(9-(4-methylpiperazin-1-yl)methyl)benzo[4,5]imidazo[1,2-a]pyridin-2-yl)pyridin-2-yl)oxy)propan-1-amine (Example 11);
N,N-dimethyl-3-((5-(9-((1-methylpiperidin-4-yl)oxy)benzo[4,5]imidazo[1,2-a]pyridin-2-yl)pyridin-2-yl)oxy)propan-1-amine (Example 12);
N,N-dimethyl-3-((5-(9-((tetrahydro-2H-pyran-4-yl)oxy)benzo[4,5]imidazo[1,2-a]pyridin-2-yl)pyridin-2-yl)oxy)propan-1-amine (Example 13);
N,N-dimethyl-3-((5-(9-(tetrahydro-2H-pyran-4-ylamino)benzo[4,5]imidazo[1,2-a]pyridin-2-yl)pyridin-2-yl)oxy)propan-1-amine (Example 14);
N,N-dimethyl-3-((5-(9-(1-methylpiperidin-4-ylamino)benzo[4,5]imidazo[1,2-a]pyridin-2-yl)pyridin-2-yl)oxy)propan-1-amine (Example 15);
1-(6-(4-methylpiperazin-1-yl)pyridin-3-yl)-8-morpholinobenzo[4,5]imidazo[1,2-a]pyridine (Example 16);
1-(6-((3S,5R)-3,4,5-trimethylpiperazin-1-yl)pyridin-3-yl)-8-morpholinobenzo[4,5]imidazo[1,2-a]pyridine (Example 17);
N,N-dimethyl-3-((6-(9-(3,6-dihydro-2H-pyran-4-yl)benzo[4,5]imidazo[1,2-a]pyridin-2-yl)pyridin-3-yl)oxy)propan-1-amine (Example 18);
1-(6-(4-methylpiperazin-1-yl)pyridin-3-yl)-8-(3,6-dihydro-2H-pyran-4-yl)benzo[4,5]imidazo[1,2-a]pyridine (Example 19);
1-(6-((3 S,5R)-3,4,5-trimethylpiperazin-1-yl)pyri din-3-yl)-8-(3,6-dihydro-2H-pyran-4-yl)benzo[4,5]imidazo[1,2-a] pyridine (Example 20);
N,N-dimethyl-3-((5-(9-(tetrahydro-2H-pyran-4-yl)benzo[4,5]imidazo[1,2-a]pyridin-2-yl)pyridin-2-yl)oxy)propan-1-amine (Example 21);
N,N-dimethyl-3-((5-(9-(1-methylpiperidin-4-yl)benzo[4,5]imidazo[1,2-a]pyridin-2-yl)pyridin-2-yl)oxy)propan-1-amine (Example 22);
N,N-dimethyl-3-((5-(9-(1H-imidazol-4-yl)benzo[4,5]imidazo[1,2-a]pyridin-2-yl)pyridin-2-yl)oxy)propan-1-amine (Example 23);
N,N-dimethyl-3-((5-(9-(piperidin-4-yloxy)benzo[4,5]imidazo[1,2-a]pyridin-2-yl)pyridin-2-yl)oxy)propan-1-amine (Example 24);
N,N-dimethyl-3-((5-(6-(3,6-dihydro-2H-pyran-4-yl)benzo[4,5]imidazo[1,2-a]pyrimidin-3-yl)pyridin-2-yl)oxy)propan-1-amine (Example 25);
N,N-dimethyl-3-((5-(6-(tetrahydro-2H-pyran-4-yl)benzo[4,5]imidazo[1,2-a]pyrimidin-3-yl)pyridin-2-yl)oxy)propan-1-amine (Example 26);

N,N-dimethyl-3-((5-(6-morpholinobenzo[4,5]imidazo[1,2-a]pyrimidin-3-yl)pyridin-2-yl)oxy)propan-1-amine (Example 27);

N,N-dimethyl-3-((5-(6-(3,6-dihydro-2H-pyran-4-yl)benzo[4,5]imidazo[1,2-a]pyrazin-3-yl)pyridin-2-yl)oxy)propan-1-amine (Example 28);

N,N-dimethyl-3-((5-(6-(tetrahydro-2H-pyran-4-yl)benzo[4,5]imidazo[1,2-a]pyrazin-3-yl)pyridin-2-yl)oxy)propan-1-amine (Example 29);

N,N-dimethyl-3-((5-(6-morpholinobenzo[4,5]imidazo[1,2-a]pyrazin-3-yl)pyridin-2-yl)oxy)propan-1-amine (Example 30);

N,N-dimethyl-3-((5-(9-(3,6-dihydro-2H-pyran-4-yl)benzo[4,5]imidazo[1,2-b]pyridazin-2-yl)pyridin-2-yl)oxy)propan-1-amine (Example 31);

N,N-dimethyl-3-((5-(9-morpholinobenzo[4,5]imidazo[1,2-b]pyridazin-2-yl)pyridin-2-yl)oxy)propan-1-amine (Example 32);

N,N-dimethyl-3-((5-(4-(3,6-dihydro-2H-pyran-4-yl)imidazo[1,2-a:4,5-b]dipyridin-7-yl)pyridin-2-yl)oxy)propan-1-amine (Example 33);

N,N-dimethyl-3-((5-(4-morpholinoimidazo[1,2-a:4,5-b]dipyridin-7-yl)pyridin-2-yl)oxy)propan-1-amine (Example 34);

N,N-dimethyl-3-((5-(4-(3,6-dihydro-2H-pyran-4-yl)imidazo[1,2-a:4,5-c]dipyridin-7-yl)pyridin-2-yl)oxy)propan-1-amine (Example 35);

N,N-dimethyl-3-((5-(4-morpholinoimidazo[1,2-a:4,5-c]dipyridin-7-yl)pyridin-2-yl)oxy)propan-1-amine (Example 36);

N,N-dimethyl-3-((5-(1-(3,6-dihydro-2H-pyran-4-yl)imidazo[1,2-a:5,4-c]dipyridin-8-yl)pyridin-2-yl)oxy)propan-1-amine (Example 37);

N,N-dimethyl-3-((5-(1-morpholinoimidazo[1,2-a:5,4-c]dipyridin-8-yl)pyridin-2-yl)oxy)propan-1-amine (Example 38);

N,N-dimethyl-1-(4-(9-(3,6-dihydro-2H-pyran-4-yl)benzo[4,5]imidazo[1,2-a]pyridin-2-yl)phenyl)piperidin-4-amine (Example 39);

N,N-dimethyl-1-(5-(9-(3,6-dihydro-2H-pyran-4-yl)benzo[4,5]imidazo[1,2-a]pyridin-2-yl)pyridin-2-yl)piperidin-4-amine (Example 40);

N,N-dimethyl-1-(4-(9-morpholinobenzo[4,5]imidazo[1,2-a]pyridin-2-yl)phenyl)piperidin-4-amine (Example 41);

N,N-dimethyl-1-(5-(9-morpholinobenzo[4,5]imidazo[1,2-a]pyridin-2-yl)pyridin-2-yl)piperidin-4-amine (Example 42);

N,N-dimethyl-1-(2-(trifluoromethyl)-4-(9-(4-methylpiperazin-1-yl)benzo[4,5]imidazo[1,2-a]pyridin-2-yl)-phenyl)piperidin-4-amine (Example 43);

N,N-dimethyl-3-(2-(trifluoromethyl)-4-(9-(4-methylpiperazin-1-yl)benzo[4,5]imidazo[1,2-a]pyridin-2-yl)phenoxy)propan-1-amine (Example 44);

N,N-dimethyl-1-(4-(9-((3S,5R)-3,4,5-trimethylpiperazin-1-yl)benzo[4,5]imidazo[1,2-a]pyridin-2-yl)phenyl)piperidin-4-amine (Example 45);

N,N-dimethyl-1-(2-fluoro-4-(9-((3S,5R)-3,4,5-trimethylpiperazin-1-yl)benzo[4,5]imidazo[1,2-a]pyridin-2-yl)phenyl)piperidin-4-amine (Example 46);

N,N-dimethyl-1-(2-chloro-4-(9-((3S,5R)-3,4,5-trimethylpiperazin-1-yl)benzo[4,5]imidazo[1,2-a]pyridin-2-yl)phenyl)piperidin-4-amine (Example 47);

N,N-dimethyl-1-(2-(trifluoromethyl)-4-(9-((3S,5R)-3,4,5-trimethylpiperazin-1-yl)benzo[4,5]imidazo[1,2-a]pyridin-2-yl)phenyl)piperidin-4-amine (Example 48);

N,N-dimethyl-3-(4-(9-((3S,5R)-3,4,5-trimethylpiperazin-1-yl)benzo[4,5]imidazo[1,2-a]pyridin-2-yl)phenoxy)propan-1-amine (Example 49);

N,N-dimethyl-3-(2-fluoro-4-(9-((3S,5R)-3,4,5-trimethylpiperazin-1-yl)benzo[4,5]imidazo[1,2-a]pyridin-2-yl)phenoxy)propan-1-amine (Example 50);

N,N-dimethyl-3-(2-chloro-4-(9-((3S,5R)-3,4,5-trimethylpiperazin-1-yl)benzo[4,5]imidazo[1,2-a]pyridin-2-yl)phenoxy)propan-1-amine (Example 51);

N,N-dimethyl-3-(2-bromo-4-(9-((3S,5R)-3,4,5-trimethylpiperazin-1-yl)benzo[4,5]imidazo[1,2-a]pyridin-2-yl)phenoxy)propan-1-amine (Example 52);

N,N-dimethyl-3-(2-(trifluoromethyl)-4-(9-((3S,5R)-3,4,5-trimethylpiperazin-1-yl)benzo[4,5]imidazo[1,2-a]pyridin-2-yl)phenoxy)propan-1-amine (Example 53);

N,N-dimethyl-1-(2-(trifluoromethyl)-4-(9-((2S,6R)-2,6-dimethylmorpholino)benzo[4,5]imidazo[1,2-a]pyridin-2-yl)phenyl)piperidin-4-amine (Example 54);

N,N-dimethyl-3-(2-(trifluoromethyl)-4-(9-((2S,6R)-2,6-dimethylmorpholino)benzo[4,5]imidazo[1,2-a]pyridin-2-yl)phenoxy)propan-1-amine (Example 55);

N,N-dimethyl-1-(4-(9-(4-(dimethylamino)piperidin-1-yl)benzo[4,5]imidazo[1,2-a]pyridin-2-yl)phenyl)piperidin-4-amine (Example 56);

N,N-dimethyl-1-(2-(3-fluoro-4-(4-(dimethylamino)piperidin-1-yl)phenyl)benzo[4,5]imidazo[1,2-a]pyridin-9-yl)piperidin-4-amine (Example 57);

N,N-dimethyl-1-(2-(3-chloro-4-(4-(dimethylamino)piperidin-1-yl)phenyl)benzo[4,5]imidazo[1,2-a]pyridin-9-yl)piperidin-4-amine (Example 58);

N,N-dimethyl-1-(2-(3-bromo-4-(4-(dimethylamino)piperidin-1-yl)phenyl)benzo[4,5]imidazo[1,2-a]pyridin-9-yl)piperidin-4-amine (Example 59);

N,N-dimethyl-1-(2-(3-(trifluoromethyl)-4-(4-(dimethylamino)piperidin-1-yl)phenyl)benzo[4,5]imidazo[1,2-a]pyridin-9-yl)piperidin-4-amine (Example 60);

N,N-dimethyl-1-(2-(3-(trifluoromethyl)-4-(4-(methylamino)piperidin-1-yl)phenyl)benzo[4,5]imidazo[1,2-a]pyridin-9-yl)piperidin-4-amine (Example 61);

N,N-dimethyl-1-(2-(3-(trifluoromethyl)-4-(4-(ethylamino)piperidin-1-yl)phenyl)benzo[4,5]imidazo[1,2-a]pyridin-9-yl)piperidin-4-amine (Example 62);

N,N-dimethyl-1-(2-(6-(3-(dimethylamino)propoxy)pyridin-3-yl)benzo[4,5]imidazo[1,2-a]pyridin-9-yl)piperidin-4-amine (Example 63);

N,N-dimethyl-1-(2-(4-(3-(dimethylamino)propoxy)phenyl)benzo[4,5]imidazo[1,2-a]pyridin-9-yl)piperidin-4-amine (Example 64);

N,N-dimethyl-1-(2-(3-fluoro-4-(3-(dimethylamino)propoxy)phenyl)benzo[4,5]imidazo[1,2-a]pyridin-9-yl)piperidin-4-amine (Example 65);

N,N-dimethyl-1-(2-(3-chloro-4-(3-(dimethylamino)propoxy)phenyl)benzo[4,5]imidazo[1,2-a]pyridin-9-yl)piperidin-4-amine (Example 66);

N,N-dimethyl-1-(2-(3-bromo-4-(3-(dimethylamino)propoxy)phenyl)benzo[4,5]imidazo[1,2-a]pyridin-9-yl)piperidin-4-amine (Example 67);

N,N-dimethyl-1-(2-(3-(trifluoromethyl)-4-(3-(dimethylamino)propoxy)phenyl)benzo[4,5]imidazo[1,2-a]pyridin-9-yl)piperidin-4-amine (Example 68);

N,N-dimethyl-1-(2-(trifluoromethyl)-4-(9-((1-methylpiperidin-4-yl)oxy)benzo[4,5]imidazo[1,2-a]pyridin-2-yl)phenyl)piperidin-4-amine (Example 69);

N,N-dimethyl-3-(2-(trifluoromethyl)-4-(9-((1-methylpiperidin-4-yl)oxy)benzo[4,5]imidazo[1,2-a]pyridin-2-yl)phenoxy)propan-1-amine (Example 70);

N,N-dimethyl-1-(4-(4-(((3 S,5R)-3,4,5-trimethylpiperazin-1-yl)pyridazino[6,1-f]purin-7-yl)phenyl)piperidin-4-amine (Example 71);

or pharmaceutically acceptable salts or prodrugs thereof.

The term "alkyl" as employed herein refers to alkyl itself or straight or branched chain radicals of up to ten carbons. Useful alkyl groups include straight-chained or branched $C_{1-10}$ alkyl groups, more preferably $C_{1-6}$ alkyl groups, e.g., $C_{1-4}$ alkyl. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein means a straight or branched chain radical of 2-10 carbon atoms, unless the chain length is limited thereto, wherein there is at least one double bond between two of the carbon atoms in the chain. The chain length of alkenyl can be from two to six carbon atoms. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. The chain length of alkynyl can be from two to six carbon atoms. Typical alkynyl groups include ethynyl, 1-propynyl, 1-methyl-2-propynyl, 2-propynyl, 1-butynyl and 2-butynyl.

Useful alkoxy groups include oxy group substituted by $C_{1-10}$ alkyl groups, such as $C_1$-$C_6$ alkoxy or $C_1$-$C_4$ alkoxy, mentioned above. The alkyl in the alkoxy group may be optionally substituted. The substituents for alkoxy include, without limitation, halo, morpholinyl, amino including alkylamino and dialkylamino, and carboxy including ester group thereof.

Useful alkylthio groups include thio group substituted by $C_{1-10}$ alkyl groups as mentioned above. The alkyl in the alkylthio group may be optionally substituted. Also included are the sulfoxides and sulfones of such alkylthio groups.

Useful amino and optionally substituted amino groups include $NR_3R_4$, wherein $R_3$ and $R_4$ are hydrogen, optionally substituted $C_{1-10}$ alkyl (e.g. $C_{1-6}$ alkyl or $C_{1-4}$ alkyl), optionally substituted cycloalkyl, optionally substituted aryl, optionally substituted heteroaryl, or optionally substituted amino; or $R_3$ and $R_4$ are combined with the N to form a 5-8 membered heterocyclic ring, such as a piperidine; or $R_3$ and $R_4$ are combined with the N and an additional N or O atom to form a 5-8 membered heterocyclic ring, such as a piperazine. The alkyl and heterocyclic ring are optionally substituted.

Useful halo or halogen groups include fluoro, chloro, bromo and iodo.

The term "aryl" as employed herein by itself or as part of another group refers to monocyclic, bicyclic or tricyclic aromatic groups containing from 6 to 14 carbon atoms in the ring portion.

Useful aryl groups include $C_6$-$C_{14}$ aryl, preferably $C_6$-$C_{10}$ aryl. Typical $C_6$-$C_{14}$ aryl groups include phenyl, naphthyl, phenanthrenyl, anthracenyl, indenyl, azulenyl, biphenyl, biphenylenyl and fluorenyl groups.

The term "heteroaryl" as employed herein refers to groups having 5 to 14 ring atoms; 6, 10 or 14 π electrons shared in a cyclic array; and containing, as ring atom, carbon atoms and 1-3 heteroatoms selected from oxygen, nitrogen and sulfur.

Useful heteroaryl groups include thienyl (thiophenyl), benzo[d]isothiazol-3-yl, benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, imidazolyl, pyrazolyl, pyridyl (pyridinyl, including without limitation 2-pyridyl, 3-pyridyl, and 4-pyridyl), pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-amino-isocoumarin, pyrido[1,2-a]pyrimidin-4-one, tetrahydrocyclopenta[c]pyrazol-3-yl, pyrazolo[1,5-c]pyrimidinyl, pyrrolopyridyl such as pyrrolo[2,3-b]pyridyl, benzoisoxazolyl such as 1,2-benzoisoxazol-3-yl, benzimidazolyl, 2-oxindolyl, thiadiazolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "carbocycle (carbocyclic group)" as employed herein includes saturated or partially saturated carbocyclic groups. Saturated carbocyclic groups include cycloalkyl, such as $C_3$-$C_5$ cycloalkyl. Typical cycloalkyl groups include cyclopropyl, cyclobutyl, cyclopentyl, cyclohexyl and cycloheptyl.

Partially saturated carbocyclic groups are cycloalkenyl groups, such as $C_3$-$C_5$ cycloalkenyl, for example, cyclopentenyl, cycloheptenyl and cyclooctenyl.

The term "heterocycle (heterocyclic group)" is used herein to mean a saturated or partially saturated 3-7 membered monocyclic, or 7-10 membered bicyclic ring system, which consists of carbon atoms and one to four heteroatoms independently selected from the group consisting of 0, N, and S, wherein the nitrogen and sulfur heteroatoms can be optionally oxidized, the nitrogen can be optionally quaternized. The term also includes any bicyclic group in which any of the above-defined heterocyclic rings is fused to a benzene ring. The heterocyclic ring of heterocycle can be substituted on carbon or nitrogen atoms if the resulting compound is stable.

Useful saturated or partially saturated heterocyclic groups include tetrahydrofuranyl, dihydropyranyl, tetrahydropyranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups, which are optionally substituted.

In this disclosure, "optionally subsituted", "can be substituted" or similar expression have the same meaning. When substituted, the aryl, heteroaryl, carbocyclic and heterocyclic groups may be substituted by one or more (such as 1, 2, 3, or 4) substituents selected from the group consisting of halo, hydroxy, carboxyl, amino, nitro, cyano, $C_{1-6}$ acylamino, $C_{1-6}$ acyloxy, $C_{1-6}$ alkoxy, aryloxy, alkylthio, $C_{1-6}$ alkyl, $C_{6-10}$ aryl, $C_{3-8}$ cycloalkyl, $C_{2-6}$ alkenyl, $C_{2-6}$ alkynyl, $C_{6-10}$ aryl($C_{2-6}$)alkenyl, $C_{6-10}$ aryl($C_{2-6}$)alkynyl, saturated and unsaturated heterocyclic or heteroaryl, methylenedioxy, $C_{1-6}$ haloalkyl, $C_{6-10}$ aryl($C_{1-6}$)alkyl, $C_{1-6}$ hydroxyalkyl, ureido, thiol, azido, carbonyl, di($C_{1-10}$ alkyl)amino, alkyl sulfonyl, aminosulfonyl, dialkylaminosulfonyl, and alkylsulfinyl, and the like. The substituent itself may also be optionally substituted.

In this disclosure, when substituted, alkyl, alkoxy, alkylthio, alkenyl, alkynyl, and cycloalkyl may be optionally substituted by one or more (such as 1, 2, 3, or 4) substituents selected from the group consisting of halo, hydroxy, carboxyl, amino, nitro, cyano, $C_{1-6}$ acylamino, $C_{1-6}$ acyloxy, $C_{1-6}$ alkoxy, aryloxy, alkylthio, $C_{1-6}$ alkyl, $C_{6-10}$ aryl, $C_{3-8}$ cycloalkyl, $C_{2-6}$ alkenyl, $C_{2-6}$ alkynyl, $C_{6-10}$ aryl($C_{2-6}$)alkenyl, $C_{6-10}$ aryl($C_{2-6}$)alkynyl, saturated and unsaturated heterocyclic or heteroaryl, methylenedioxy, $C_{1-6}$ haloalkyl, $C_{6-10}$ aryl($C_{1-6}$)alkyl, $C_{1-6}$ hydroxyalkyl, ureido, thiol, azido, carbonyl, di($C_{1-10}$ alkyl)amino, alkyl sulfonyl, aminosulfonyl, dialkylaminosulfonyl, and alkylsulfinyl, and the like. The substituent itself may also be optionally substituted.

In preferred embodiments, when substituted, alkyl, alkoxy, alkylthio, alkenyl, alkynyl, cycloalkyl, carbonyl, carbocyclic and heterocyclic groups, may be optionally substituted by one or more (such as 1, 2, 3, or 4) substituents selected from the group consisting of halo, hydroxy, carboxyl, amino, nitro, cyano, $C_{1-6}$ acylamino, $C_{1-6}$ acyloxy, $C_{1-6}$ alkoxy, aryloxy, alkylthio, $C_{1-6}$ alkyl, $C_{6-10}$ aryl, $C_{3-8}$ cycloalkyl, $C_{2-6}$ alkenyl, $C_{2-6}$ alkynyl, $C_{6-10}$ aryl($C_{2-6}$)alkenyl, $C_{6-10}$ aryl($C_{2-6}$)alkynyl, saturated and unsaturated heterocyclic or heteroaryl.

It should be understood that in each embodiment, when the substituent is an aryl, a heteraryl, or a heterocyclic group, the number thereof is usually 1.

The term "arylalkyl" includes $C_{1-10}$ alkyl groups substituted by any of the above-mentioned $C_{6-14}$ aryl groups. Preferably the arylalkyl group is benzyl, phenethyl or naphthylmethyl.

The term "arylalkenyl" includes $C_{2-10}$ alkenyl groups substituted by any of the above-mentioned $C_{6-14}$ aryl groups.

The term "arylalkynyl" includes $C_{2-10}$ alkynyl groups substituted by any of the above-mentioned $C_{6-14}$ aryl groups.

The term "aryloxy" includes oxy group substituted by any of the above-mentioned $C_{6-14}$ aryl groups, which may be optionally substituted. Useful aryloxy groups include phenoxy and 4-methylphenoxy.

The term "arylalkoxy" includes $C_{1-10}$ alkoxy groups substituted by any of the above-mentioned aryl groups, which may be optionally substituted. Useful arylalkoxy groups include benzyloxy and phenethyloxy.

Useful haloalkyl groups include $C_{1-10}$ alkyl, or preferably $C_{1-6}$ alkyl substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido. Useful acyl includes $C_{1-6}$ acyl, such as acetyl.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

In addition, it should be understood that one or more groups may be selected from each of the ranges defined for $A_1$-$A_3$, $B_1$-$B_3$, $D_1$-$D_4$, and $R_1$-$R_8$ in the above Formulae I and II respectively and combined to form preferred embodiments of the present disclosure; and the various technical features in the various embodiments described in the present disclosure, the definitions of the various groups, and the various technical features described specifically hereafter (e.g., in the Examples) may be combined with each other to form preferred technical solutions. For example, in some embodiments, the ring including $A_1$-$A_3$ is preferably phenyl or pyridyl; in some embodiments, the ring including $B_1$-$B_3$ is pyridyl, pyrimidinyl, pyrazinyl or pyradazinyl; in some embodiments, R', R" and R'" are H. In some embodiments, $A_1$-$A_3$ are all CH; in some embodiments, $B_1$-$B_3$ are all CH; in some embodiments, the ring including $A_1$-$A_3$, imidazolyl ring and the ring including $B_1$-$B_3$ are fused to form benzo[4,5]imidazo[1,2-a]pyridinyl, benzo[4,5]imidazo[1,2-a]pyrimidinyl, benzo[4,5]imidazo[1,2-a]pyrazinyl, benzo[4,5]imidazo[1,2-b]pyridazinyl, imidazo[1,2-a:4,5-b'] dipyridinyl, imidazo[1,2-a:4,5-c']dipyridinyl or imidazo[1,2-a:5,4-c']dipyridinyl; in some embodiments, $R_1$ is selected from the group consisting of dihydropyranyl; tetrahydropyranyl; piperidyl that is not substituted or optionally substituted with 1-4 $C_{1-6}$ alkyl or —$NR_3R_4$ groups; morpholinyl; imidazolyl; piperazinyl that is optionally substituted with 1-4 $C_{1-6}$ alkyl groups; or $C_{1-6}$ alkyl or amino or oxy group that is optionally substituted with an optionally substituted heterocyclic group; in some embodiments, the ring including $D_1$-$D_4$ is pyridyl or optionally substituted phenyl; in some embodiments, $R_2$ is selected from the group consisting of $C_{1-6}$ alkoxyl optionally substituted with —$NR_3R_4$, piperazinyl optionally substituted with 1-3 $C_{1-4}$ alkyl groups, piperidyl optionally substituted with —$NR_3R_4$; wherein $R_3$ and $R_4$ are independently selected from H and $C_{1-6}$ alkyl groups. The technical features of each implementation scheme can be arbitrarily combined.

Therefore, for example, in some embodiments, the ring including $A_1$-$A_3$, imidazolyl ring and the ring including $B_1$-$B_3$ in the compounds of the present disclosure are fused to form benzo[4,5]imidazo[1,2-a]pyridinyl, benzo[4,5]imidazo[1,2-a]pyrimidinyl, benzo[4,5]imidazo[1,2-a]pyrazinyl, benzo[4,5]imidazo[1,2-b]pyridazinyl, imidazo[1,2-a:4,5-c] dipyridinyl or imidazo[1,2-a:5,4-c']dipyridinyl; the ring including $D_1$-$D_4$ is pyridyl or optionally substituted phenyl; R', R" and R'" are H; $R_1$ is selected from the group consisting of dihydropyranyl; tetrahydropyranyl; piperidyl that is not substituted or optionally substituted with 1-4 $C_{1-6}$ alkyl or —$NR_3R_4$ groups; morpholinyl; imidazolyl; piperazinyl that is optionally substituted with 1-4 $C_{1-6}$ alkyl groups; or $C_{1-6}$ alkyl or amino or oxy group that is optionally substituted with an optionally substituted heterocyclic group; and $R_2$ is selected from the group consisting of $C_{1-6}$ alkoxyl optionally substituted with —$NR_3R_4$, piperazinyl optionally substituted with 1-3 $C_{1-4}$ alkyl groups, piperidyl optionally substituted with —$NR_3R_4$; wherein $R_3$ and $R_4$ are independently selected from H and $C_{1-6}$ alkyl groups.

In some embodiments, the ring including $A_1$-$A_3$, imidazolyl ring and the ring including $B_1$-$B_3$ in the compounds of the present disclosure are fused to form benzo[4,5]imidazo [1,2-a]pyridinyl; the ring including $D_1$-$D_4$ is pyridyl or optionally substituted phenyl; R', R" and R'" are H; $R_1$ is selected from the group consisting of dihydropyranyl; tetrahydropyranyl; piperidyl that is not substituted or optionally substituted with 1-4 $C_{1-6}$ alkyl or —$NR_3R_4$ groups; morpholinyl; imidazolyl; piperazinyl that is optionally substituted with 1-4 $C_{1-6}$ alkyl groups; or $C_{1-6}$ alkyl or amino or oxy group optionally substituted by morpholinyl, 1-3 $C_{1-6}$ alkyl-substituted piperazinyl, $C_{1-6}$ alkyl-substituted piperidinyl or tetrahydropyranyl; and $R_2$ is selected from the group consisting of $C_{1-6}$ alkoxyl optionally substituted with —$NR_3R_4$, piperazinyl optionally substituted with 1-3 $C_{1-4}$ alkyl groups, piperidyl optionally substituted with —$NR_3R_4$; wherein $R_3$ and $R_4$ are independently selected from H and $C_{1-6}$ alkyl groups. In some embodiments, the ring including $A_1$-$A_3$, imidazolyl ring and the ring including $B_1$-$B_3$ in the compounds of the present disclosure are fused to form benzo[4,5]imidazo[1,2-a]pyrimidinyl or benzo[4,5] imidazo[1,2-a]pyrazinyl; the ring including $D_1$-$D_4$ is pyridyl; R', R" and R'" are H; $R_1$ is selected from the group consisting of dihydropyranyl, tetrahydropyranyl or morpholinyl; and $R_2$ is selected from the group consisting of $C_{1-6}$ alkoxy substituted by —$NR_3R_4$, wherein $R_3$ and $R_4$ are independently selected from H and $C_{1-6}$ alkyl. In some embodiments, the ring including $A_1$-$A_3$, imidazolyl ring and the ring including $B_1$-$B_3$ in the compounds of the present disclosure are fused to form benzo[4,5]imidazo[1,2-b]pyridazinyl, imidazo[1,2-a:4,5-c]dipyridinyl or imidazo[1,2-a: 5,4-c']dipyridinyl; the ring including $D_1$-$D_4$ is pyridyl; R', R" and R'" are H; $R_1$ is selected from dihydropyranyl or morpholinyl; and $R_2$ is selected from $C_{1-6}$ alkoxy substituted by —$NR_3R_4$, wherein $R_3$ and $R_4$ are independently selected from H and $C_{1-6}$ alkyl.

Some of the compounds of the present disclosure may exist as stereoisomers including optical isomers. The disclosure includes all stereoisomers and both the racemic mixtures of such stereoisomers as well as the individual enantiomers that may be separated according to methods that are well known to those of ordinary skill in the art.

Examples of pharmaceutically acceptable salts include inorganic and organic acid salts, such as hydrochloride, hydrobromide, phosphate, sulphate, citrate, lactate, tartrate, maleate, fumarate, mandelate and oxalate; and inorganic and organic base salts with bases, such as sodium hydroxy, tris(hydroxymethyl)aminomethane (TRIS, tromethamine) and N-methyl-glucamine.

Examples of prodrugs of the compounds of the disclosure include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The compounds of this disclosure may be prepared using methods known to those skilled in the art, or the novel methods of this disclosure. Specifically, the compounds of this disclosure with Formula I can be prepared as illustrated by the exemplary reaction in Scheme 1. 2-Amino-3-nitrophenol and an aqueous solution of 30% sulfuric acid are reacted in DMSO under heating, followed by dropwise addition of a sodium nitrite aqueous solution to react at room temperature, then followed by dropwise addition of a potassium iodide aqueous solution to react at room temperature, resulting in a product 2-iodo-3-nitrophenol. 2-Iodo-3-nitrophenol, potassium carbonate and benzyl bromide are reacted at room temperature in DMF to obtain a product 1-(benzyloxy)-2-iodo-3-nitrobenzene. 1-(Benzyloxy)-2-iodo-3-nitrobenzene, iron powder and ammonium chloride are reacted at room temperature in ethanol and water to obtain a product 3-(benzyloxy)-2-iodoaniline. 3-(Benzyloxy)-2-iodoaniline, 2-iodo-5-bromopyridine, cesium carbonate, cuprous iodide and 1,10-phenanthroline are reacted in xylene under heating to obtain a product 9-(benzyloxy)-2-bromobenzo[4,5]imidazo[1,2-a]pyridine. 9-(Benzyloxy)-2-bromobenzo[4,5]imidazo[1,2-a]pyridine, 6-(3-(dimethylamino)propoxy-3-pyridinyl)boronic acid, cesium carbonate and [1,1'-bis(diphenylphosphine)ferrocene] palladium dichloride dichloromethane complex are reacted in dioxane and water under heating to obtain a product 3-((5-(9-(benzyloxy)benzo[4,5]imidazo[1,2-a]pyridin-2-yl)pyridin-2-yl)oxy)-N,N-dimethyl-1-propylamine. 3-((5-(9-(Benzyloxy)benzo[4,5]imidazo[1,2-a]pyridin-2-yl)pyridin-2-yl)oxy)-N,N-dimethyl-1-propylamine and 10% palladium on carbon are reacted in methanol to obtain a product 2-(6-(3-(dimethylamino)propoxy)pyridin-3-yl)benzo[4,5]imidazo[1,2-a]pyridine-9-phenol. 2-(6-(3-(Dimethylamino)propoxy)pyridin-3-yl)benzo[4,5]imidazo[1,2-a]pyridine-9-phenol, cesium carbonate and N-phenyl bis(trifluoromethanesulfonimide) are reacted in tetrahydrofuran at room temperature to obtain a product 2-(6-(3-(dimethylamino) propoxy)pyridin-3-yl)benzo[4,5]imidazo[1,2-a]pyridin-9-yl trifluoromethanesulfonate. 2-(6-(3-(Dimethylamino)propoxy)pyridin-3-yl)benzo[4,5]imidazo[1,2-a]pyridin-9-yl trifluoromethanesulfonate, 3,6-dihydro-2H-pyran-4-boronic add pinacol ester, sodium carbonate and tetrakis(triphenylphosphine)palladium are reacted under heating reaction in dioxane and water to produce a target compound N,N-dimethyl-3-((5-(9-(3,6-dihydro-2H-pyran-4-yl)benzo[4,5]imidazo[1,2-a]pyridin-2-yl)pyridin-2-yl)oxy)propan-1-amine.

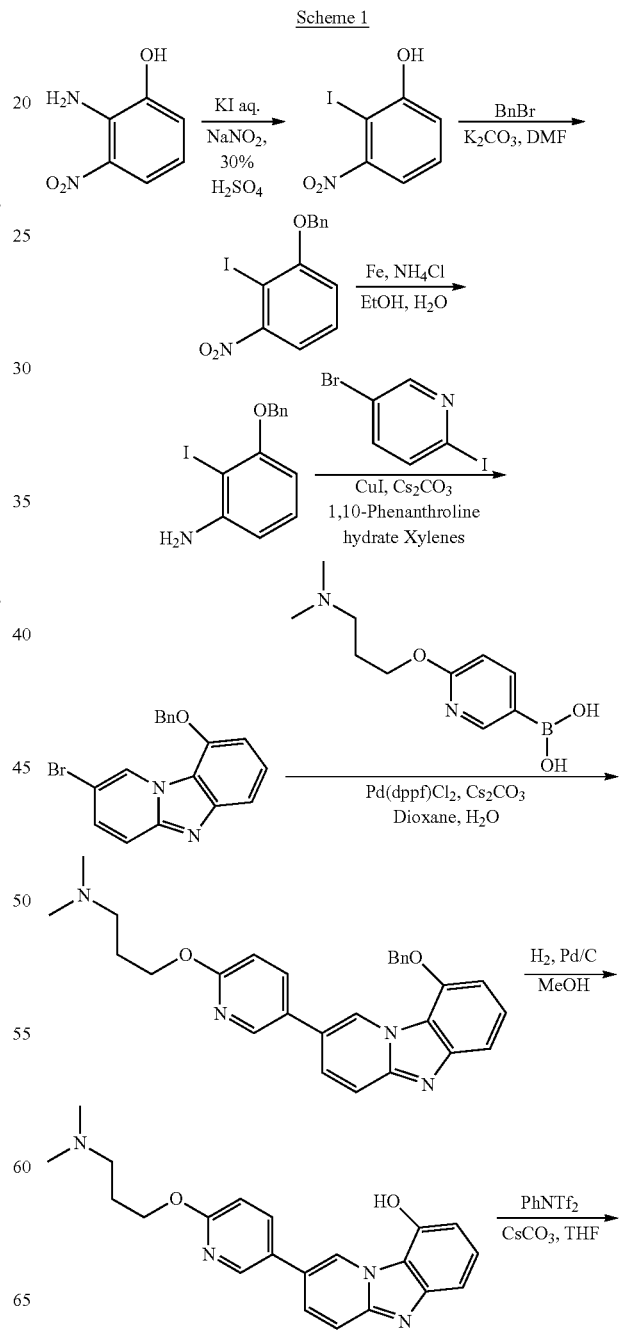

Scheme 1

-continued

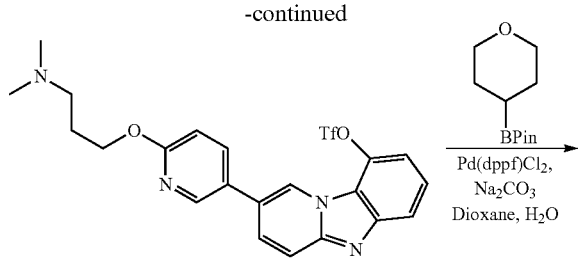

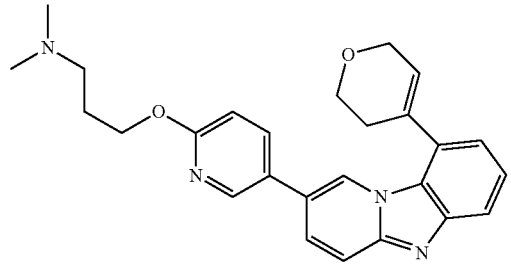 [SMILES: CN(C)CCCOc1ccc(-c2ccc3nc4cccc(C5=CCOCC5)c4n3c2)cn1]

Other related compounds can be prepared similarly. For example, replacement of 6-(3-(dimethylamino)propoxy-3-pyridinyl)boronic acid with 4-(3-(dimethylamino)propoxy) phenylboronic acid may produce a target compound N,N-dimethyl-3-(4-(9-(3,6-dihydro-2H-pyran-4-yl)benzo[4,5]imidazo[1,2-a]pyridin-2-yl) phenoxy)propan-1-amine. Replacement of 6-(3-(dimethylamino)-propoxy-3-pyridinyl) boronic acid with 6-(4-methylpiperazin-1-yl)-3-pyridinyl-boronic acid may produce a target compound 1-(6-(4-methylpiperazin-1-yl)pyridin-3-yl)-8-(3,6-dihydro-2H-pyran-4-yl)benzo[4,5]imidazo[1,2-a]pyridine. Replacement of 3,6-dihydro-2H-pyran-4-boronic acid pinacol ester with tetrahydro-2H-pyran-4-boronic acid pinacol ester may produce a target compound N,N-dimethyl-3-((5-(9-(tetrahydro-2H-pyran-4-yl)benzo[4,5]imidazo[1,2-a]pyridin-2-yl)pyridin-2-yl)oxy)propan-1-amine. Replacement of 2-iodo-5-bromopyridine with 5-bromo-2-iodopyrimidine may produce a target compound N,N-dimethyl-3-((5-(6-(3,6-dihydro-2H-pyran-4-yl)benzo[4,5]imidazo[1,2-a]pyrimidin-3-yl)pyridin-2-yl)oxy)propan-1-amine. Replacement of 2-amino-3-nitrophenol with 3-amino-2-nitro-4-hydroxypyridine may produce a target compound N,N-dimethyl-3-((5-(4-(3,6-dihydro-2H-pyran-4-yl)imidazo[1,2-a:4,5-b] dipyridin-7-yl)pyridin-2-yl)oxy)propan-1-amine.

3-Chloro-2-nitroaniline, N-methylpiperazine and potassium carbonate are reacted in N,N-dimethylformamide under heating to obtain a product 3-(4-methylpiperazin-1-yl)-2-nitroaniline. 3-(4-Methylpiperazin-1-yl)-2-nitroaniline, a sulfuric acid aqueous solution, a sodium nitrite aqueous solution and a potassium iodide aqueous solution are reacted at 0° C. to obtain a product 1-(3-iodo-2-nitrophenyl)-4-methylpiperazine. 1-(3-Iodo-2-nitrophenyl)-4-methylpiperazine, reduced iron powder and ammonium chloride are reacted in ethanol and water under heating to obtain a product 2-iodo-6-(4-methylpiperazin-1-yl)aniline. 2-Iodo-6-(4-methyl piperazin-1-yl) aniline, cuprous bromide and isoamyl nitrite are reacted in acetonitrile at 0° C. to obtain a product 1(2-bromo-3-iodophenyl)-4-methylpiperazine. 1-(2-Bromo-3-iodophenyl)-4-methylpiperazine and 2-amino-5-bromopyridine are reacted in toluene under heating under the catalysis of palladium acetate, 2,2'-bis-(diphenylphosphino)-1,1'-dinaphthalene and cesium carbonate to obtain a product 5-bromo-N-(2-bromo-3-(4-methylpiperazin-1-yl)phenyl)pyridin-2-amine. 5-Bromo-N-(2-bromo-3-(4-methylpiperazin-1-yl)phenyl)pyridin-2-amine, N,N'-dimethylethylenediamine, cuprous iodide and cesium carbonate are reacted in dimethyl sulfoxide under heating to obtain a product 2-bromo-9-(4-methylpiperazin-1-yl)benzo [4,5]imidazo[1,2-a]pyridine. 2-Bromo-9-(4-methylpiperazin-1-yl)benzo[4,5]imidazo[1,2-a]pyridine and 3-(N,N-dimethylamino)propoxyphenylboronic acid pinacol ester are reacted in dioxane and water under heating under the catalysis of [1,1'-bis(diphenylphosphine)ferrocene] palladium dichloride and potassium carbonate to obtain a target compound N,N-dimethyl-3-(4-(9-(4-methylpiperazin-1-yl) benzo[4,5]imidazo[1,2-a]pyridin-2-yl)phenoxy)propan-1-amine.

Scheme 2

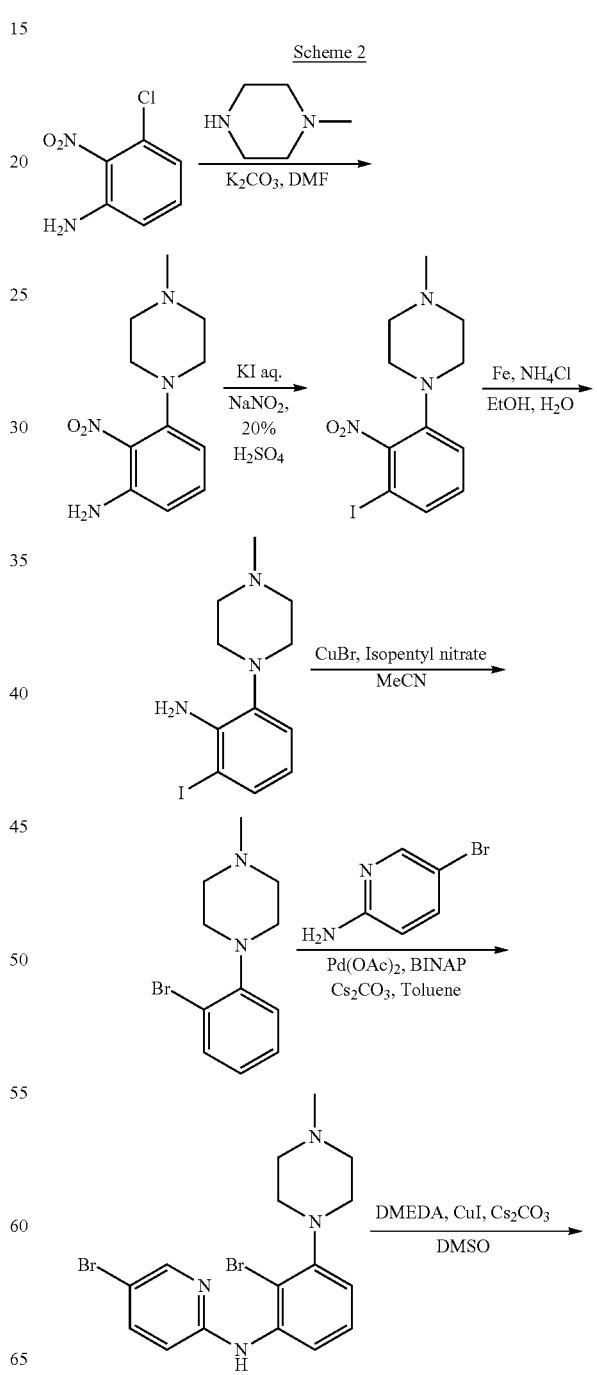

-continued

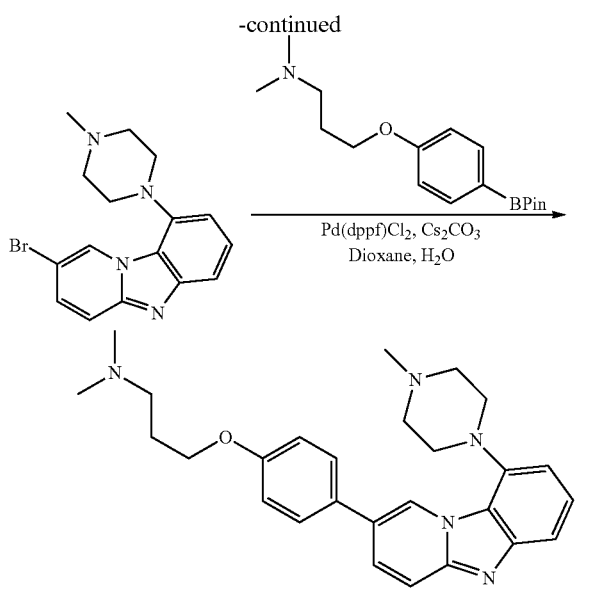

Scheme 3

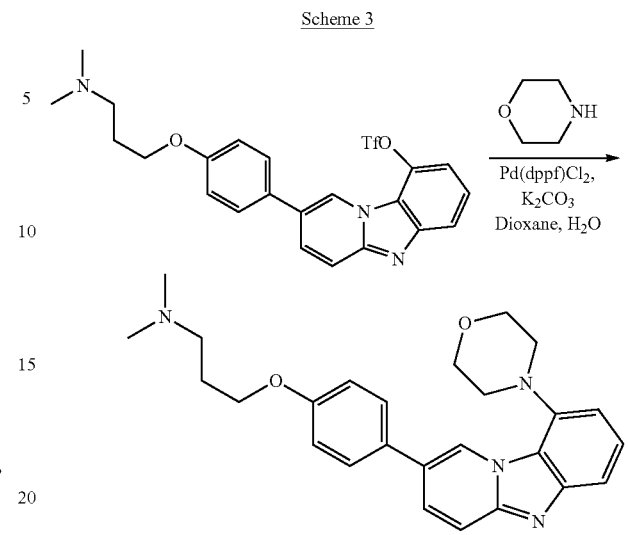

Other related compounds can be prepared using similar methods. For example, replacement of 1-methylpiperazine with (2R,6S)-1,2,6-trimethylpiperazine may produce a target compound N,N-dimethyl-3-(4-(9-((3S,5R)-3,4,5-trimethylpiperazin-1-yl)benzo[4,5]imidazo[1,2-a]pyridin-2-yl)phenoxy)propan-1-amine. Replacement of 1-methylpiperazine with morpholine may produce a target compound 1-(6-(4-methylpiperazine-1-yl)pyridin-3-yl)-8-morpholinobenzo[4,5]imidazo[1,2-a] pyridine. Replacement of 3-(N,N-dimethylamino)propoxyphenylboronic acid pinacol ester with N,N-dimethyl-4-(4-(4,4,5,5-tetramethyl-1,3,2-dioxaborolan-2-yl)-2-(trifluoromethyl)phenyl)piperidin-4-amine may produce a target compound N,N-dimethyl-1-(2-(trifluoromethyl)-4-(9-(4-methylpiperazin-1-yl)benzo[4,5]imidazo[1,2-a]pyridin-2-yl)phenyl)piperidin-4-amine. Replacement of 1-methylpiperazine with (2S,6R)-2,6-dimethylmorpholine may produce a target compound N,N-dimethyl-1-(2-(trifluoromethyl)-4-(9-((2S,6R)-2,6-dimethylmorpholino)benzo[4,5]imidazo[1,2-a]pyridin-2-yl)phenyl)piperidin-4-amine. Use of N,N-dimethylpiperidin-4-amine may produce a target compound N,N-dimethyl-1-(2-(3-(trifluoromethyl)-4-(4-(dimethylamino)piperidin-1-yl)phenyl)benzo[4,5]imidazo[1,2-a]pyridin-9-yl)piperidin-4-amine.

The compounds of this disclosure can be prepared as illustrated by the exemplary reaction in Scheme 3. First, following the synthesis method of Scheme 1, an intermediate product 2-(4-(3-(dimethylamino)propoxy)phenyl)benzo[4,5]imidazo[1,2-a]pyridin-9-yl trifluoromethanesulfonate is prepared using 4-(3-(dimethylamino)propoxy)phenylboronic acid in place of 6-(3-(dimethylamino)propoxy-3-pyridinyl)boronic acid. Then, 2-(4-(3-(dimethylamino)propoxy)phenyl)benzo[4,5]imidazo[1,2-a]pyridin-9-yl trifluoromethanesulfonate and morpholine are reacted in toluene under heating under the catalysis of palladium acetate, 2,2'-bis-(diphenylphosphino)-1,1'-dinaphthalene and cesium carbonate to obtain a target compound N,N-dimethyl-3-(4-(9-morpholinobenzo[4,5]imidazo[1,2-a]pyridin-2-yl)phenoxy)propan-1-amine.

Other related compounds can be prepared using similar methods. For example, replacement of 2-(4-(3-(dimethylamino)propoxy)phenyl)benzo[4,5]imidazo[1,2-a]pyridin-9-yl trifluoromethanesulfonate with 2-(6-(3-(dimethylamino)propoxy)pyridin-3-yl)benzo[4,5]imidazo[1,2-a]pyridin-9-yl trifluoromethanesulfonate may produce a target compound N,N-dimethyl-3-((5-(9-morpholinobenzo[4,5]imidazo[1,2-a]pyridin-2-yl)pyridin-2-yl)oxy)propan-1-amine. Replacement of morpholine with piperidine may lead to preparation of a target compound N,N-dimethyl-3-((5-(9-(piperidin-1-yl)benzo[4,5]imidazo[1,2-a]pyridin-2-yl)pyridin-2-yl)oxy)-1-propylamine. Replacement of 2-(4-(3-(dimethylamino)propoxy)phenyl)benzo[4,5]imidazo[1,2-a]pyridin-9-yl trifluoromethanesulfonate with 2-(4-(4-(dimethylamino)piperidin-1-yl) phenyl)benzo[4,5]imidazo[1,2-a]pyridin-9-yl trifluoromethanesulfonate may lead to preparation of a target compound N,N-dimethyl-1-(4-(9-morpholinobenzo[4,5]imidazo[1,2-a]pyridin-2-yl)phenyl)piperidin-4-amine.

The compounds of this disclosure can be prepared as illustrated by the exemplary reaction in Scheme 4. A solution of 2,6-dinitroaniline in acetic acid, a sodium nitrite solution in concentrated sulfuric acid and an aqueous solution of potassium iodide are reacted under heating to obtain a product 2,6-dinitroiodobenzene. 2,6-Dinitroiodobenzene and reduced iron powder are reacted in acetic acid under heating to obtain a product 2-iodo-3-nitroaniline. 2-Iodo-3-nitroaniline, 2-iodo-5-bromopyridine, cuprous iodide, 1,10-phenanthroline and cesium carbonate are reacted in anhydrous xylene under heating to obtain a product 2-bromo-9-nitrobenzo[4,5]imidazo[1,2-a]pyridine. 2-Bromo-9-nitrobenzo[4,5]imidazo[1,2-a]pyridine, ammonium chloride and reduced iron powder are reacted in ethanol and water at room temperature to obtain a product 2-bromobenzo[4,5]imidazo[1,2-a]pyridin-9-amine. 2-Bromobenzo[4,5]imidazo[1,2-a]pyridin-9-amine, glyoxal, formaldehyde and ammonium chloride are reacted in methanol under heating for a period of time, and phosphoric acid is added to continue the reaction to obtain a product 2-bromo-9-(1H-imidazol-1-yl)benzo[4,5]imidazo[1,2-a]pyridine. 2-Bromo-9-(1H-imidazol-1-yl)benzo[4,5]imidazo[1,2-a]pyridine and (6-(3-(dimethylamino)propyl)pyridin-3-yl)boronic acid pinacol ester are reacted in dioxane and water under heating under the catalysis of [1,1'-bis(diphenylphosphine)ferrocene] palladium dichloride and cesium carbonate to obtain a target compound N,N-dimethyl-3-((5-(9-(1H-imidazol-1-yl)benzo[4,5]imidazo[1,2-a]pyridin-2-yl)pyridin-2-yl)oxo)propan-1-amine.

Scheme 4

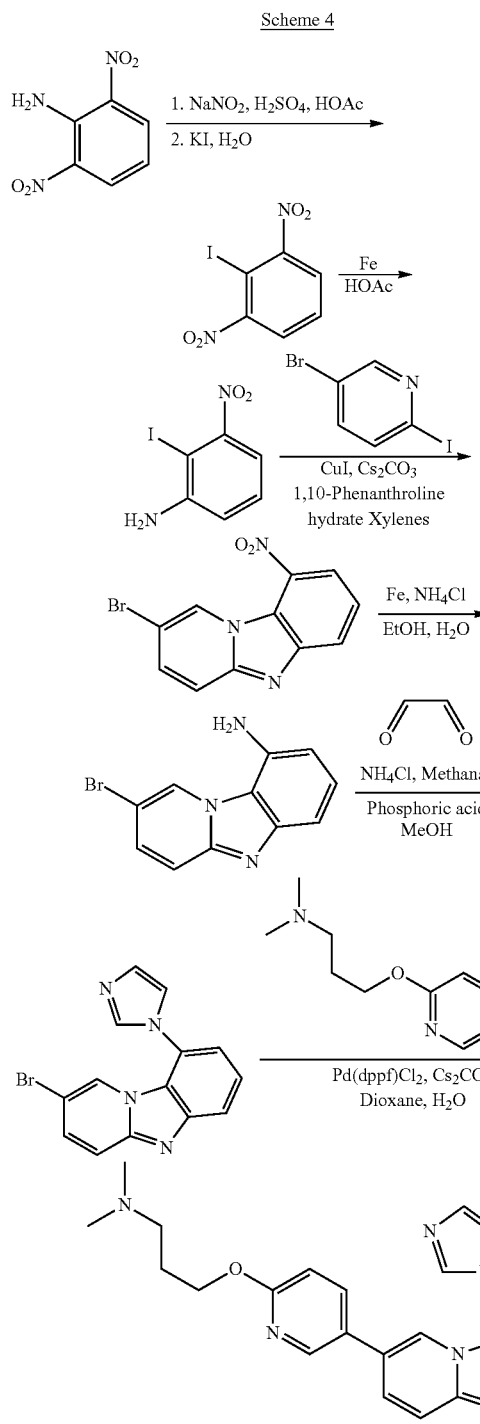

borohydride are reacted in methanol at 0° C. to obtain a product (2-bromobenzo[4,5]imidazo[1,2-a]pyridin-9-yl)benzyl alcohol, (2-Bromobenzo[4,5]imidazo[1,2-a]pyridin-9-yl)benzyl alcohol and manganese dioxide are reacted in dichloromethane and N,N-dimethylformamide at room temperature to obtain a product 2-bromobenzo[4,5]imidazo[1,2-a]pyridine-9-carbaldehyde. 2-Bromobenzo[4,5]imidazo[1,2-a]pyridine-9-carbaldehyde, morpholine and tetraisopropyl titanate are reacted in tetrahydrofuran under heating, and then sodium borohydride is added to react at room temperature to obtain a product 4-((2-bromobenzo[4,5]imidazo[1,2-a]pyridin-9-yl)methyl)morpholine. 4-((2-Bromobenzo[4,5]imidazo[1,2-a]pyridin-9-yl)methyl)morpholine and (6-(3-(dimethylamino)propyl)pyridin-3-yl) boronic acid pinacol ester are subjected to microwave reaction in dioxane and water under heating under the catalysis of [1,1'-bis (diphenylphosphine)ferrocene] palladium dichloride and cesium carbonate to obtain a target compound N,N-dimethyl-3-((5-(9-(morpholinomethyl)benzo[4,5]imidazo[1,2-a]pyridin-2-yl)pyridin-2-yl)oxy)propan-1-amine.

Scheme 5

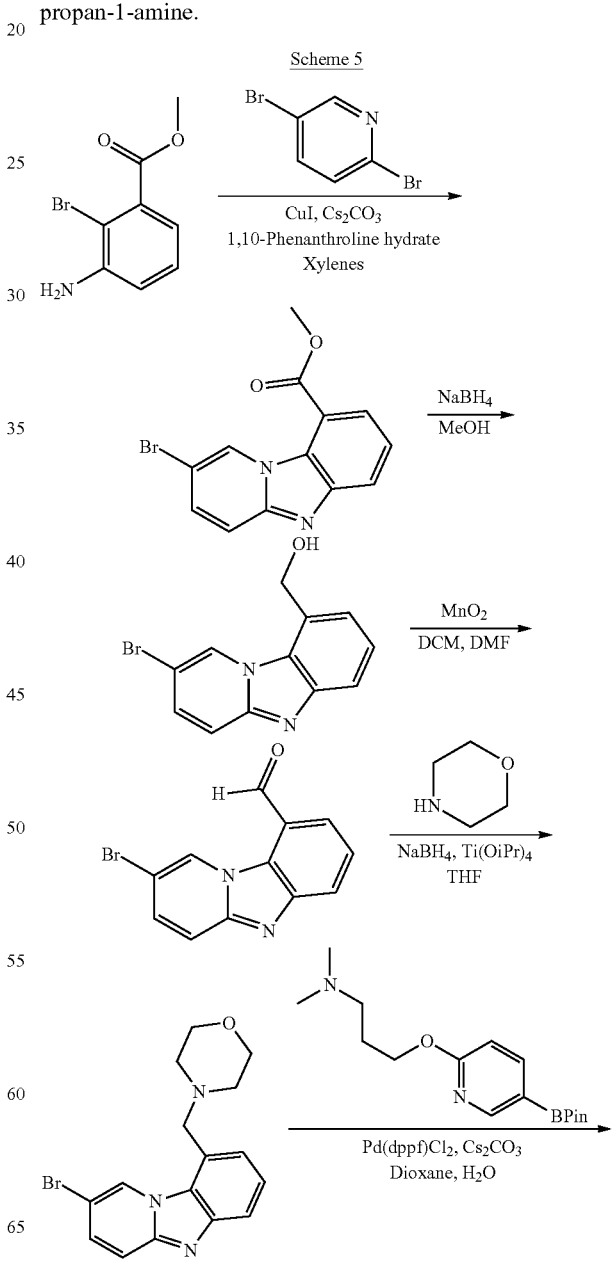

The compounds of this disclosure can be prepared as illustrated by the exemplary reaction in Scheme 5. Methyl 3-amino-2-bromobenzoate, 2,5-dibromopyridine, cuprous iodide, 1,10-phenanthroline and cesium carbonate are subjected to microwave reaction under heating in anhydrous toluene to obtain a product methyl 2-bromobenzo[4,5]imidazo[1,2-a]pyridine-9-carboxylate. Methyl 2-bromobenzo[4,5]imidazo[1,2-a]pyridine-9-carboxylate and sodium -continued

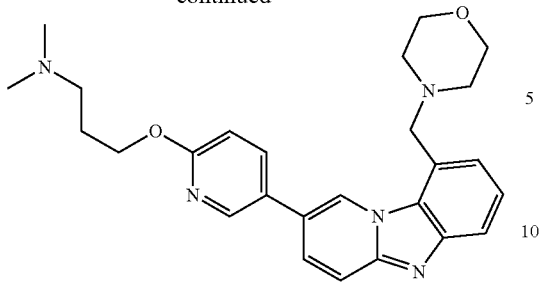

Other related compounds can be prepared using similar methods. For example, replacement of morpholine with N-methylpiperazine may lead to preparation of a target compound. N,N-dimethyl-3-((5-(9-((4-methylpiperazin-1-yl)methyl)benzo[4,5]imidazo[1,2-a]pyridin-2-yl)pyridin-2-yl)oxy)propan-1-amine.

The compounds of this disclosure can be prepared as illustrated by the exemplary reaction in Scheme 6. 9-Benzyloxy-2-bromobenzo[4,5]imidazo[1,2-a]pyridine is reacted in trifluoroacetic acid to obtain a product 2-bromobenzo[4,5]imidazo[1,2-a]pyridin-9-ol. 2-Bromobenzo[4,5]imidazo[1,2-a]pyridin-9-ol, tert-butyl 4-(tosyloxy)piperidine-1-carboxylate and potassium carbonate are reacted in N,N-dimethylformamide under heating to obtain a product tert-butyl 4-((2-bromobenzo[4,5]imidazo[1,2-a]pyridin-9-yl)oxy)piperidine-1-carboxylate. Tert-butyl 4-((2-bromobenzo[4,5]imidazo[1,2-a]pyridin-9-yl)oxy)piperidine-1-carboxylate and a hydrochloric acid solution in 1,4-dioxane are reacted in methanol at room temperature to obtain a product 2-bromo-9-(piperidin-4-yloxy)benzo[4,5]imidazo[1,2-a]pyridine. 2-Bromo-9-(piperidin-4-yloxy)benzo[4,5]imidazo[1,2-a]pyridine and paraformaldehyde are reacted in formic acid under heating to obtain a product 9-(1-methylpiperidin-4-oxy)-2-bromobenzo[4,5]imidazo[1,2-a] pyridine. 9-(1-Methylpiperidin-4-oxy)-2-bromobenzo[4,5]imidazo[1,2-a] pyridine and N,N-dimethyl-3-((5-(4,4,5,5-tetramethyl-1,3,2-dioxaborolan-2-yl)pyridin-2-yl)oxy)propan-1-amine are reacted in dioxane and water under heating under the catalysis of cesium carbonate and [1,1'-bis(diphenylphosphine)ferrocene]palladium dichloride to obtain a target compound N,N-dimethyl-3-((5-(9-((1-methylpiperidin-4-yl)oxy)benzo[4,5]imidazo[1,2-a]pyridin-2-yl)pyridin-2-yl)oxy)propan-1-amine.

Scheme 6

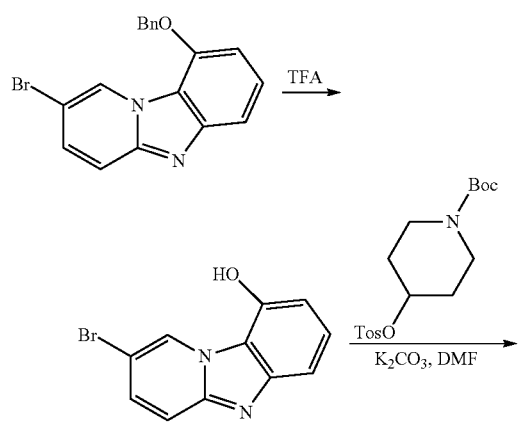

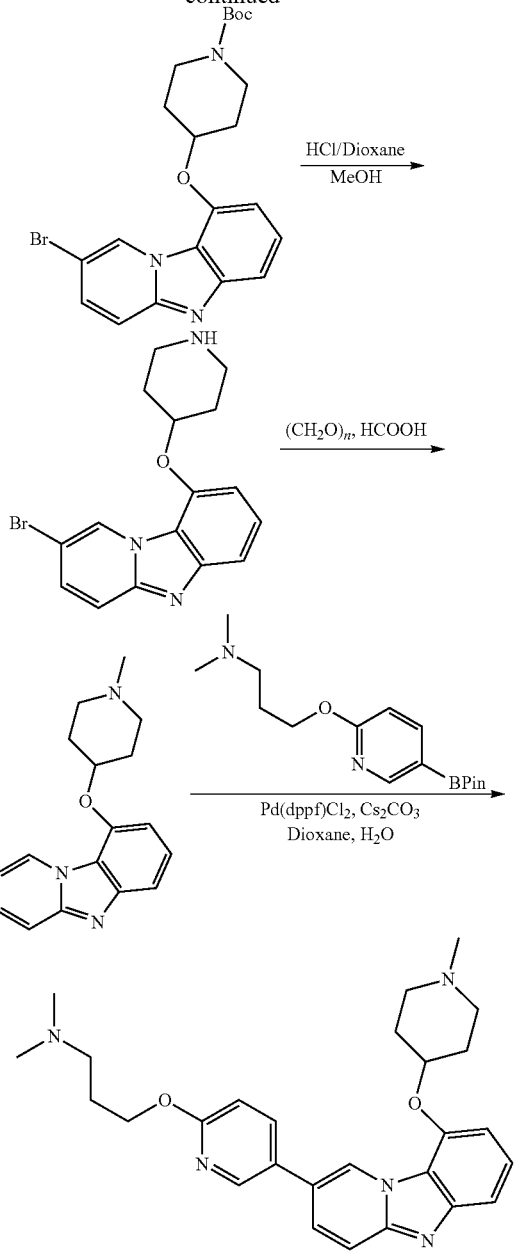

Other related compounds can be prepared using similar methods. For example, replacement of tert-butyl 4-(tosyloxy)piperidine-1-carboxylate with tetrahydro-2H-pyran-4-yl-4-toluene sulfonate may produce a target compound N,N-dimethyl-3-((5-(9-(tetrahydro-2H-pyran-4-yl)oxy)benzo[4,5]imidazo[1,2-a]pyridin-2-yl)pyridin-2-yl)oxy)propan-1-amine.

One important aspect of the present disclosure is the find that the compounds of Formulae I and II are kinase inhibitors, including ATM kinase inhibitors. Therefore, these compounds can be used to treat or prevent a variety of clinical diseases caused by DDR dysfunction or diseases that benefit from the inhibition of ATM kinase activity, such as cancer. In some embodiments, a disease that may be treated or prevented by a compound, pharmaceutical composition, or method of the present disclosure is a DDR-mediated or ATM kinase-mediated disease, as described below.

The present disclosure includes a treatment or prevention method comprising administering to an animal an effective amount of a compound of Formula I or II, or a pharmaceutically acceptable salt or prodrug thereof, wherein the treatment or prevention method is used for the treatment or prevention of clinical conditions caused by DDR dysfunction or diseases benefiting from the inhibition of ATM kinase activity, or DDR-mediated or ATM kinase-mediated diseases, such as cancer. Such diseases include, but are not limited to, liver cancer, melanoma, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head and neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds of Formula I or II formulated for oral, intravenous, local or topical application, for the treatment of cancer and other diseases, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to an effective regimen. The amount may cure the disease but, typically, is administered in order to ameliorate the symptoms of the disease. Typically, repeated administration is required to achieve the desired amelioration of symptom.

In another embodiment, there is provided a pharmaceutical composition comprising a ATM kinase inhibitor of Formula I or II or a pharmaceutically acceptable salt thereof and a pharmaceutically acceptable carrier.

Another embodiment of the present disclosure is directed to a pharmaceutical composition effective to treat or prevent cancer comprising a compound of Formula I or II, or a pharmaceutically acceptable salt or prodrug thereof, which functions as a ATM kinase inhibitor, in combination with at least one known anticancer agent or a pharmaceutically acceptable salt thereof. In particular, the compound herein can be combined with other anticancer drugs related to the mechanism of DNA damage and repair, including PARP inhibitors Olaparib, Niraprib, Rucaparib and Talazoparib; HDAC inhibitors Volinota, Romididesin, Papiseta and Bailesta; and so on. And the compound herein can be combined with other anticancer drugs related to cell division detection sites, including Chk1/2 inhibitors, CDK4/6 inhibitors such as Paposinib, Weel/ATR inhibitors, and so on. Known anticancer agents which may be used for combination therapy include, but are not limited to alkylating agents, such as busulfan cis-platin, mitomycin C, and carboplatin; antimitotic agent such as colchicine, vinblastine, paclitaxel, and docetaxel; topoisomerase I inhibitors, such as camptothecin and topotecan; topoisomerase II inhibitors, such as doxorubicin, and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; antibodies such as campath, trastuzumab and rituximab. Other known anticancer agents which may be used for combination therapy include melphalan, chlorambucil, cyclophosphamide, iphosfamide, vincristine, mitoguazone, epirubicin, aclacinomycin, bleomycin, mitoxantrone, methylhydroxy ellipticine, fludarabine, octreotide, retinoic acid, tamoxifen, arsenic trioxide, gemcitabine, letrozole, fulvestrant, bendamustine, pralatrexate, pemetrexed, nelarabine, temozolomide, zoledronic acid, irinotecan, ixabepilone, cabazitazel, vinorebine, panitumumab, Ofatumumab, avastin, imatinib, gefitinib, erlotinib, lapatinib, sorafinib, sunitinib, nilotinib, dasatinib, pazopanib, bortezomib, vorinostat, romidepsin, torisel, everolimus, thalidomide, lenalidomide, and thioguanine.

In practicing the methods of the present disclosure, the compound of the disclosure may be administered together with at least one known anticancer agent as part of a unitary pharmaceutical composition. Alternatively, the compound of the disclosure may be administered apart from at least one known anticancer agent. In one embodiment, the compound of the disclosure and at least one known anticancer agent are administered substantially simultaneously, i.e. the compounds are administered at the same time or one after the other, so long as the compounds reach therapeutic levels in the blood at the same time. In another embodiment, the compound of the disclosure and at least one known anticancer agent are administered according to their individual dose schedule, so long as the compounds reach therapeutic levels in the blood.

Another embodiment of the present disclosure is directed to a bioconjugate, which functions as a ATM kinase inhibitor, that comprises a compound described herein and is effective to inhibit neoplasia. The bioconjugate that inhibits neoplasia is consisted of a compound described herein and at least one known therapeutically useful antibody, such as trastuzumab or rituximab, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of the therapeutically useful antibodies, such as trastuzumab or rituximab.

Similarly, another embodiment of the present disclosure is directed to a composition effective to inhibit neoplasia comprising a compound of Formula I or II, or its pharmaceutically acceptable salt or prodrug, which functions as a ATM kinase inhibitor, in combination with radiation therapy. In this embodiment, the compound of the disclosure may be administered at the same time as the radiation therapy is administered or at a different time.

Yet another embodiment of the present disclosure is directed to a pharmaceutical composition effective for post-surgical treatment of cancer, comprising a compound of Formula I or II, or its pharmaceutically acceptable salt or prodrug, which functions as a ATM kinase inhibitor. The disclosure also relates to a method of treating cancer by surgically removing the tumor and then treating the cancer of the mammal with one of the pharmaceutical compositions described herein.

Pharmaceutical compositions within the scope of this disclosure include all compositions wherein the compounds of the present disclosure are contained in an amount that is effective to achieve its intended purpose. While individual needs vary, determination of optimal ranges of effective amounts of each component is within the skill of the art. Typically, the compounds or the pharmaceutically acceptable salt thereof may be administered to mammals, orally at a dose of from about 0.0025 to 50 mg/kg of body weight, per day. Preferably, from approximately 0.01 to approximately 10 mg/kg of body weight is orally administered. If a known anticancer agent is also administered, it is administered in an amount that is effective to achieve its intended purpose. The optimal amounts of such known anticancer agents effective for cancer are well known to those skilled in the art.

The unit oral dose may comprise from approximately 0.01 to approximately 50 mg, preferably approximately 0.1 to approximately 10 mg of the compound of the disclosure. The unit dose may be administered one or more times daily, as one or more tablets, each containing from approximately 0.1 to approximately 50 mg, conveniently approximately 0.25 to 10 mg of the compound or its solvates.

In a topical formulation, the compound may be present at a concentration of approximately 0.01 to 100 mg per gram of carrier.

The compounds of the present disclosure may be administered as a raw chemical. The compounds of the disclosure may be also administered as part of a suitable pharmaceutical preparation containing pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, as well as suitable solutions for administration by injection or orally, contain from approximately 0.01 to 99 percent, preferably from approximately 0.25 to 75 percent of active compound(s), together with the excipient.

Also included within the scope of the present disclosure are the non-toxic pharmaceutically acceptable salts of the compounds of the present disclosure. Acid addition salts are formed by mixing a solution of the compounds of the present disclosure with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Base addition salts are formed by mixing a solution of the compounds of the present disclosure with a solution of a pharmaceutically acceptable non-toxic base, such as sodium hydroxide, potassium hydroxide, choline hydroxide, sodium carbonate, tris(hydroxymethyl)aminomethane (TRIS), N-methyl-glucamine and the like.

The pharmaceutical preparations of the disclosure may be administered to any mammals, so long as they may experience the therapeutic effects of the compounds of the disclosure. Foremost among such mammals are humans and veterinary animals, although the disclosure is not intended to be so limited.

The pharmaceutical preparations of the present disclosure may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present disclosure are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, including, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose, such as cellulose acetate phthalate or hydroxypropylmethyl-cellulose phthalate, are used. Dye stuffs or pigments may be added to the tablets or dragee coatings, e.g., for identification or in order to characterize combinations of active compound doses.

Other pharmaceutical preparations, which may be used orally, include push-fit capsules made of gelatin, as well as soft, sealed capsules made of gelatin and a plasticizer, such as glycerol or sorbitol. The push-fit capsules may contain the active compounds in the form of granules, which may be mixed with fillers, such as lactose; binders, such as starches; and/or lubricants, such as talc or magnesium stearate and/or stabilizers. In soft capsules, the active compounds are preferably dissolved or suspended in suitable liquids, such as fatty oils, or liquid paraffin. In addition, stabilizers may be added.

Suitable formulations for parenteral administration include aqueous solutions of the active compounds, e.g., aqueous solutions and alkaline solutions of water-soluble salts. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400, or cremophor, or cyclodextrins. Aqueous injection suspensions may contain substances which increase the viscosity of the suspension, e.g., sodium carboxymethyl cellulose, sorbitol, and/or dextran. Optionally, the suspension may also contain stabilizers.

In accordance with one aspect of the present disclosure, compounds of the disclosure are employed in topical and parenteral formulations and are used for the treatment of skin cancer.

The topical formulations of this disclosure are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The following examples are illustrative, but not limiting, of the method and compositions of the present disclosure. Other suitable modifications and adaptations of the variety of conditions and parameters normally encountered in clinical therapy and which are obvious to those skilled in the art are within the spirit and scope of the disclosure.

EXAMPLES

General Remarks

All reagents were of commercial quality. Solvents were dried and purified by standard methods. Mass spectrum analyses were recorded on a Platform II (Agilent 6110) quadrupole mass spectrometer fitted with an electrospray. $^1$H NMR spectra was recorded at 400 MHz, on a Brucker Ascend 400 apparatus. Chemical shifts were recorded as parts per million (ppm) downfield from TMS (0.00 ppm), and J coupling constants were reported in hertz (Hz).

Example 1

N,N-dimethyl-3-((5-(9-(3,6-dihydro-2H-pyran-4-yl)benzo[4,5]imidazo[1,2-a]pyridin-2-yl)pyridin-2-yl)oxy)propan-1-amine a) 2-Iodo-3-nitrophenol: 2-amino-3-nitrophenol (300 mg, 1.95 mmol) was dissolved in DMSO (3 mL), and a aqueous solution of 30% sulfuric acid (3 mL) was added dropwise slowly. The resulting reaction solution was allowed to react under agitation at 50° C. for 45 min, and then cooled to room temperature. A sodium nitrite aqueous solution (161 mg dissolved in 1 mL of water) was added dropwise slowly. After the reaction solution was allowed to react under agitation at room temperature for 1 h, a potassium iodide aqueous solution (485 mg dissolved in 1 mL water) was added dropwise slowly. After the reaction solution was allowed to react under agitation at room temperature overnight, the reaction was quenched with a saturated aqueous solution of sodium bicarbonate (10 mL). Ethyl acetate (10 mL) was used for extraction and liquid separation. The organic phase was washed with a saturated aqueous solution of sodium thiosulfate and then with a saturated saline solution, dried with anhydrous sodium sulfate, filtered, and concentrated at reduced pressure to obtain a crude product. Isolation and purification by column chromatography (silica gel, petroleum ether: ethyl acetate=2:1 as an eluant) were performed to obtain the target compound (190 mg, 37% yield, yellow solid). LC-MS (ESI): m/z (M−1) 264.21.

b) 1-(Benzyloxy)-2-iodo-3-nitrobenzene: 2-iodo-3-nitrophenol (6.7 g, 25.3 mmol) and potassium carbonate (7.0 g, 50.6 mmol) were mixed in DMF (150 mL), and benzyl bromide (6.5 g, 37.9 mmol) was added dropwise slowly. After the reaction solution was allowed to react under agitation at room temperature for 1 h, ethyl acetate (100 mL) and water (300 mL) were added, and extraction and liquid separation were performed. The organic phase was washed with a saturated saline solution, dried with anhydrous sodium sulfate, filtered, and concentrated at reduced pressure to obtain a crude product. Isolation and purification by column chromatography (silica gel, petroleum ether: ethyl acetate=3:1 as an eluant) were performed to obtain the target compound (8.6 g, 96% yield, pale yellow solid). $^1$H NMR (400 MHz, CDCl$_3$): δ 7.50-7.46 (m, 2H), 7.43-7.31 (m, 4H), 7.29 (dd, J=8.0, 1.3 Hz, 1H), 7.00 (dd, J=8.2, 1.2 Hz, 1H), 5.21 (s, 2H).

c) 3-(Benzyloxy)-2-iodoaniline: 1-(benzyloxy)-2-iodo-3-nitrobenzene (8.6 g, 24.2 mmol) was dissolved in ethanol (200 mL) and water (100m mL), and iron powder (8.1 g, 144 mmol) and ammonium chloride (13 g, 242 mmol) were added. The reaction solution was allowed to react under agitation at room temperature for 3 hours, filtration was performed with diatomite. After the solvent was removed from the filtrate at reduced pressure, ethyl acetate (200 mL) and water (200 mL) were used for extraction and liquid separation. The organic phase was washed with a saturated saline solution, dried with anhydrous sodium sulfate, filtered, and concentrated at reduced pressure to obtain a crude product. Isolation and purification by column chromatography (silica gel, petroleum ether: ethyl acetate=3:1 as an eluant) were performed to obtain the target compound (7.4 g, 94% yield, colorless oily substance). LC-MS (ESI): m/z (M+1) 326.31.

d) 9-(Benzyloxy)-2-bromobenzo[4,5]imidazo[1,2-a]pyridine: 3-(benzyloxy)-2-iodoaniline (1.0 g, 3.1 mmol), 2-iodo-5-bromopyridine (1.3 g, 4.6 mmol)), cesium carbonate (3.0 g, 9.2 mmol), cuprous iodide (240 mg, 1.26 mmol) and 1,10-phenanthroline (440 mg, 2.4 mmol) were mixed in xylene (15 mL). Under the protection of nitrogen, the reaction solution was allowed to react overnight under agitation at 120° C. The solvent was removed at reduced pressure to obtain a crude product. Isolation and purification by column chromatography (silica gel, petroleum ether: ethyl acetate=3:1 as an eluant) were performed to obtain the target compound (400 mg, 37% yield, pale yellow solid). LC-MS (ESI): m/z (M+1) 353.31.

e) N,N-Dimethyl-3-((5-(9-(benzyloxy))benzo[4,5]imidazo[1,2-a]pyridin-2-yl)pyridin-2-yl)oxy)propan-1-amine: 9-(benzyloxy)-2-bromobenzo[4,5]imidazo[1,2-a]pyridine (300 mg, 0.85 mmol), 6-(3-(dimethylamino)propoxy-3-pyridine boronic acid (480 mg, 2.13 mmol), cesium carbonate (830 mg, 2.55 mmol) and [1,1'-bis(diphenylphosphine)ferrocene] palladium dichloride dichloromethane complex (70 mg, 0.085 mmol) were mixed in dioxane (10 mL) and water (2.5 mL). After reaction under agitation at 100° C. for 1 h under the protection of nitrogen, the reaction solution was cooled to room temperature, and then subjected to extraction and liquid separation with ethyl acetate (10 mL) and water (10 mL). The organic phase was washed with a saturated saline solution, dried with anhydrous sodium sulfate, filtered, and concentrated at reduced pressure to obtain a crude product. Isolation and purification by column chromatography (silica gel, methylene dichloride:methanol=10:1 as an eluant) were performed to obtain the target compound (180 mg, 47% yield, pale yellow solid). LC-MS (ESI): m/z (M+1) 453.60.

f) 2-(6-(3-(Dimethylamino)propoxy)pyridin-3-yl)benzo[4,5]imidazo[1,2-a]pyridine-9-phenol: N,N-dimethyl-3-((5-(9-(benzyloxy)benzo[4,5]imidazo[1,2-a]pyridin-2-yl)pyridin-2-yl)oxy) propan-1-amine (180 mg, 0.40 mmol)) and 10% palladium on carbon (100 mg, 0.09 mmol) were mixed in methanol (5 mL). After the reaction solution was allowed to react under agitation in a hydrogen atmosphere (ambient pressure) for 5 hours, filtration was performed with diatomite. The solvent was removed from the filtrate at reduced pressure to obtain the target compound (120 mg, 83% yield and pale yellow oily substance) which was used directly for the reaction in the next step without purification. LC-MS (ESI): m/z (M+1) 363.51.

g) 2-(6-(3-(Dimethylamino)propoxy)pyridin-3-yl)benzo[4,5]imidazo[1,2-a]pyridin-9-yl trifluoromethanesulfonate: 2-(6-(3-(dimethylamino)propoxy)pyridin-3-yl)benzo[4,5]imidazo[1,2-a]pyridine-9-phenol (120 mg, 0.33 mmol)) and cesium carbonate (213 mg, 0.65 mmol) were mixed in tetrahydrofuran (3 mL), and N-phenylbis(trifluoromethanesulfonimide) (117 mg, 0.33 mmol) was added. After the reaction solution was allowed to react under agitation at room temperature for 1.5 h, the reaction was quenched with a saturated aqueous solution of ammonium chloride (10 mL). Ethyl acetate (10 mL) was used for extraction and liquid separation. The organic phase was washed with a saturated saline solution, dried with anhydrous sodium sulfate, filtered, and concentrated at reduced pressure to obtain a crude product. Isolation and purification by column chromatography (silica gel, methylene dichloride:methanol=10:1 as an eluant) were performed to obtain the target compound (100 mg, 61% yield, pale yellow oily substance). LC-MS (ESI): m/z (M+1) 495.32.

h) N,N-Dimethyl-3-((5-(9-(3,6-dihydro-2H-pyran-4-yl)benzo[4,5]imidazo[1,2-a]pyridin-2-yl)pyridin-2-yl)oxy) propan-1-amine: 2-(6-(3-(dimethylamino)propoxy)pyridin-3-yl)benzo[4,5]imidazo[1,2-a]pyridin-9-yl trifluoromethanesulfonate (100 mg, 0.20 mmol), 3,6-dihydro-2H-pyran-4-boronic acid pinacol ester (80 mg, 0.38 mmol), sodium carbonate (60 mg, 0.57 mmol) and tetrakis(triphenylphosphine)palladium (30 mg, 0.026 mmol) were mixed in dioxane (4 mL) and water (1 mL). Under the protection of nitrogen, the reaction solution was allowed to react under agitation at 100° C. for 30 min. The solvent was removed at reduced pressure to obtain a crude product. Isolation and purification by preparative liquid chromatography (C18 column, 0-100% acetonitrile/water as a mobile phase) were performed to obtain the target compound (50 mg, 58% yield, white solid).

Example 2 was prepared using a synthetic process similar to that described in Example 1e-1h, wherein the starting materials were 9-(benzyloxy)-2-bromobenzo[4,5]imidazo[1,2-a]pyridine (Example 1d), 4-(3-(dimethylamino)propoxy)phenylboronic acid and 3,6-dihydro-2H-pyran-4-boronic acid pinacol ester.

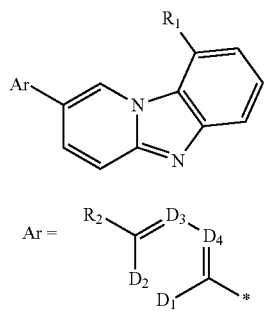

| Example | Ar | $R_1$ | LC-MS (ESI) | $^1$H NMR, 400 MHz |
|---|---|---|---|---|
| 1 | | | (M + 1) 429.48 | DMSO-$d_6$: δ 8.93 (s, 1H), 8.50 (d, J = 2.4 Hz, 1H), 8.03 (dd, J = 8.6, 2.6 Hz, 1H), 7.91 (dd, J = 9.5, 1.7 Hz, 1H), 7.86-7.75 (m, 2H), 7.55-7.47 (m, 1H), 7.14 (d, J = 6.7 Hz, 1H), 6.99 (d, J = 8.6 Hz, 1H), 6.08 (s, 1H), 4.39-4.31 (m, 4H), 3.99-3.97 (m, 2H), 2.58 (t, J = 7.3 Hz, 2H), 2.54-2.51 (m, 2H), 2.32 (s, 6H), 2.01-1.91 (m, 2H). |
| 2 | | | (M + 1) 428.32 | DMSO-$d_6$: δ 9.13 (s, 1H), 8.35 (d, J = 9.5 Hz, 1H), 8.08 (d, J = 9.5 Hz, 1H), 7.89 (d, J = 8.1 Hz, 1H), 7.81-7.61 (m, 3H), 7.36 (d, J = 7.3 Hz, 1H), 7.18 (d J = 8.6 Hz, 2H), 6.18 (s, 1H), 4.37-4.33 (m, 2H), 4.15 (t, J = 5.8 Hz, 2H), 4.01-3.95 (m, 2H), 3.30-3.21 (m, 2H), 2.84 (s, 6H), 2.60-2.52 (m, 2H), 2.19-2.11 (m, 2H). |

Example 3

N,N-dimethyl-3-(4-(9-(4-methylpiperazin-1-yl)benzo[4,5]imidazo[1,2-a]pyridin-2-yl)phenoxy)propan-1-amine a) 3-(4-Methylpiperazin-1-yl)-2-nitroaniline: at room temperature, 3-chloro-2-nitroaniline (2 g, 11.6 mmol), N-methylpiperazine (1.74 g, 17.38 mmol) and potassium carbonate (3.2 g, 23.2 mmol) were added to N,N-dimethylformamide (30 mL). After reaction under agitation at 110° C. for 18 hours, the reaction mixture was cooled to room temperature. Ethyl acetate (50 mL) and water (30 mL) were added to perform extraction and liquid separation. The aqueous phase was extracted with ethyl acetate (50 mL×2). The organic phases were combined, washed with a saturated saline solution (30 mL), dried with anhydrous sodium sulfate, filtered and concentrated at reduced pressure to obtain a crude product. Isolation and purification by column chromatography (silica gel, methylene dichloride:methanol=10:1 as an eluant) were performed to obtain the target compound (2.17 g, 79.2% yield, brownish red solid). LC-MS (ESI): m/z (M+1) 237.14.

b) 1-(3-Iodo-2-nitrophenyl)-4-methylpiperazine: at 0° C., 3-(4-methylpiperazin-1-yl)-2-nitroaniline (2.17 g, 9.18 mmol)) was dissolved in a sulfuric acid solution (20%, 30 mL), and a solution of sodium nitrite (760 mg, 11.02 mmol) in water (5 mL) was added slowly. After reaction under agitation at 0° C. for 5 min, a solution of potassium iodide (3.05 g, 18.36 mmol) in water (20 mL) was added slowly. After reaction under agitation at 0° C. for 10 min, the reaction mixture was added into a saturated aqueous solution of sodium sulfite (20 mL). After agitation for another 5 min, the pH of the mixed solution was adjusted to 8 with a sodium bicarbonate solid, and ethyl acetate (50 mL) was added to perform extraction and liquid separation. The aqueous phase was extracted with ethyl acetate (50 mL×2). The organic phases were combined, washed with a saturated saline solution (30 mL), dried with anhydrous sodium sulfate, filtered and concentrated at reduced pressure to obtain a crude product. Isolation and purification by column chromatography (silica gel, methylene dichloride:methanol=20:1 as an eluant) were performed to obtain the target compound (1.55 g, 48.6% yield, brownish red solid). LC-MS (ESI): m/z (M+1) 347.95.

c) 2-Iodo-6-(4-methylpiperazin-1-yl)aniline: at room temperature, 1-(3-iodo-2-nitrophenyl)-4-methylpiperazine (1.55 g, 4.46 mmol) was dissolved in ethanol (20 mL) and water (5 mL), and reduced iron powder (1.25 g, 22.3 mmol) and ammonium chloride (2.39 g, 44.6 mmol) were added sequentially. After reaction under agitation at 70° C. for 2 h, the reaction mixture was filtered while it was warm. Then, ethyl acetate (50 mL) and water (30 mL) were added to perform extraction and liquid separation. The aqueous phase was extracted with ethyl acetate (50 mL×2). The organic phases were combined, washed with a saturated saline solution (30 mL), dried with anhydrous sodium sulfate, filtered, and concentrated at reduced pressure to obtain a crude compound. Isolation and purification by column chromatography (silica gel, methylene dichloride:methanol=10:1 as an eluant) were performed to obtain the target compound (1.3 g, 91.9% yield, pale yellow solid). LC-MS (ESI): m/z (M+1) 317.94.

d) 1-(2-Bromo-3-iodophenyl)-4-methylpiperazine: at 0° C., 2-iodo-6-(4-methylpiperazin-1-yl)aniline (1.3 g, 4.1 mmol) was dissolved in acetonitrile (20 and cuprous bromide (2.94 g, 20.5 mmol) was added. Isoamyl nitrite (14.4 g, 123 mmol) was added dropwise slowly into the reaction system in 5 batches. After reaction under agitation at 0° C. for 1 h, the reaction mixture was added into a saturated aqueous solution of sodium sulfite (20 mL), agitated for another 5 min, and then filtered. Ethyl acetate (50 mL) and water (30 mL) were added into the filtrate to perform extraction and liquid separation. The aqueous phase was extracted with ethyl acetate (50 mL×2). The organic phases were combined, washed with a saturated saline solution (30 mL), dried with anhydrous sodium sulfate, filtered and concentrated at reduced pressure to obtain a crude product. Isolation and purification by column chromatography (silica gel, methylene dichloride:methanol=20:1 as an eluant) were performed to obtain the target compound (1 g, 64% yield, black solid). LC-MS (ESI): m/z (M+1) 380.85.

e) 5-Bromo-N-(2-bromo-3-(4-methylpiperazine-1-yl)phenyl)pyridin-2-amine: at room temperature, 1-(2-bromo-3-iodophenyl)-4-methylpiperazine (1 g, 2.62 mmol), 2-amino-5-bromopyridine (543.9 mg, 3.14 mmol), palladium acetate (58.8 mg, 0.262 mmol), 2,2'-bis-(diphenylphosphino)-1,1'-dinaphthalene (244.7 mg, 0.393 mmol) and cesium carbonate (2.58 g, 7.86 mmol) were added into toluene (10 mL). The atmosphere in the reaction system was replaced with nitrogen three times. After reaction under agitation at 100° C. for 3 h, the reaction mixture was cooled to room temperature. After filtration, concentration by removing the organic solvent at reduced pressure was performed to obtain a crude product. Isolation and purification by column chromatography (silica gel, methylene dichloride:methanol=10:1 as an eluant) was performed to obtain the target compound (875 mg, 78.4% yield, black solid). LC-MS (ESI): m/z (M+1) 425.01.

f) 2-Bromo-9-(4-methylpiperazin-1-yl)benzo[4,5]imidazo[1,2-a]pyridine: at room temperature, 5-bromo-N-(2-bromo-3-(4-methylpiperazin-1-yl)phenyl)pyridin-2-amine (875 mg, 2.05 mmol), N,N'-dimethylethylenediamine (72.4 mg, 0.82 mmol), cuprous iodide (78.1 m, 0.41 mmol) and cesium carbonate (2.02 g, 6.15 mmol) were added into dimethyl sulfoxide (10 mL). The atmosphere in the reaction system was replaced with nitrogen three times. After reaction under agitation at 100° C. for 3 h, the reaction mixture was cooled to room temperature. Ethyl acetate (50 mL) and water (30 mL) were added to perform extraction and liquid separation. The aqueous phase was extracted with ethyl acetate (50 mL×2). The organic phases were combined, washed with a saturated saline solution (30 mL×2), dried with anhydrous sodium sulfate, filtered and concentrated at reduced pressure to obtain a crude product. Isolation and purification by column chromatography (silica gel, methylene dichloride:methanol=5:1 as an eluant) were performed to obtain the target compound (395 mg, 55.9% yield, pale yellow solid). LC-MS (ESI): m/z (M+1) 345.05.

g) N,N-dimethyl-3-(4-(9-(4-methylpiperazin-1-yl)benzo[4,5]imidazo[1,2-a]pyridin-2-yl)phenoxy)propan-1-amine: at room temperature, 2-bromo-9-(4-methylpiperazin-1-yl)benzo[4,5]imidazo[1,2-a]pyridine (100 mg, 0.29 mmol), 3-(N,N-dimethylamino)propoxy phenylboronic acid pinacol ester (176.9 mg, 0.58 mmol), [1,1'-bis(diphenylphosphino)ferrocene] palladium dichloride (23.7 mg, 0,029 mmol) and potassium carbonate (240 mg, 1.74 mmol) were added into a mixed solvent of dioxane (2 mL) and water (0.5 mL). The atmosphere in the reaction system was replaced with nitrogen three times. After reaction under agitation at 100° C. for 1 h, the reaction mixture was cooled to room temperature. After filtration, concentration by removing the organic solvent at reduced pressure was performed to obtain a crude product. Isolation and purification by preparative liquid chromatography (C18 column, 0-100% acetonitrile/water as a mobile phase) were performed to obtain the target compound (9 mg, 8% yield, pale yellow solid).

Example 4

N,N-dimethyl-3-(4-(9-morpholinobenzo[4,5]imidazo[1,2-a]pyridin-2-yl)phenoxy)propan-1-amine At room temperature, 4-(3-(dimethylamino)propoxy)phenyl)benzo[4,5]imidazo[1,2-a]pyridin-9-yl trifluoromethanesulfonate (an intermediate of Example 2, 80 mg, 0.16 mmol), morpholine (49 mg, 0.24 mmol), palladium acetate (3 mg, 0.01 mmol), 2,2'-bis-(diphenylphosphino)-1,1'-dinaphthalene (10 mg, 0.02 mmol) and cesium carbonate (160 mg, 0.49 mmol) were added into toluene (1.0 mL). The atmosphere in the reaction system was replaced with nitrogen three times. After reaction under agitation at 100° C. for 30 min, the reaction mixture was cooled to room temperature. After filtration, concentration by removing the organic solvent at reduced pressure was performed to obtain a crude product. Isolation and purification by preparative liquid chromatography (C18 column, 0-100% acetonitrile/water as a mobile phase) were performed to obtain the target compound (10 mg, 14.5% yield, pale yellow solid).

Examples 5-7 were prepared using a synthetic process similar to that described in Example 4, wherein the starting materials were 2-(6-(3-(dimethylamino)propoxy)pyridin-3-yl)benzo[4,5]imidazo[1,2-a]pyridin-9-yl trifluoromethanesulfonate (Example 1h) and piperidine or morpholine or N-methylpiperazine.

Example 8 was prepared using a synthetic process similar to that described in Example 3, wherein the starting materials were 3-chloro-2-nitroaniline, (2S,6R)-1,2,6-trimethylpiperazine, potassium iodide, cuprous bromide, 5-bromopyridin-2-amine and N,N-dimethyl-3-((5-(4,4,5,5-tetramethyl-dioxaborolan-2-yl)pyridin-2-yl)oxy)propan-1-amine.

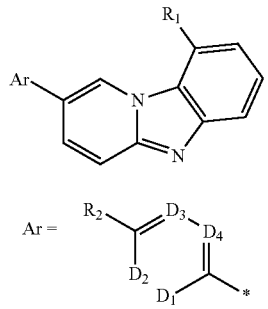

| Example | Ar | $R_1$ | LC-MS (ESI) | $^1$H NMR, 400 MHz |
|---|---|---|---|---|
| 3 | (dimethylaminopropoxy-phenyl) | (N-methylpiperazinyl) | (M + 1) 444.19 | CDCl$_3$: δ 9.43 (s, 1H), 7.75-7.65 (m, 3H), 7.59-7.54 (m, 2H), 7.46 (t, J = 7.9 Hz, 1H), 7.11 (d, J = 7.6 Hz, 1H), 7.08-7.03 (m, 2H), 4.13 (t, J = 6.1 Hz, 2H), 3.26-3.21 (m, 2H), 3.19-3.12 (m, 2H), 3.04-2.99 (m, 2H), 2.81-2.75 (m, 2H), 2.52-2.43 (m, 11H), 2.19-2.12 (m, 2H). |
| 4 | (dimethylaminopropoxy-phenyl) | (morpholinyl) | (M + 1) 431.34 | DMSO-d$_6$: δ 9.57 (s, 1H), 8.35 (d, J = 9.3 Hz, 1H), 8.08 (d, J = 9.4 Hz, 1H), 7.75 (d, J = 8.6 Hz, 2H), 7.73-7.61 (m, 2H), 7.48-7.34 (m, 1H), 7.23-7.14 (m, 2H), 4.16 (t, J = 5.6 Hz, 2H), 4.06-3.99 (m, 2H), 3.80 (t, J = 10.8 Hz, 2H), 3.29-3.24 (m, 2H), 3.23-3.16 (m, 2H), 3.08 (t, J = 11.4 Hz, 2H), 2.85 (s, 6H), 2.20-2.11 (m, 2H). |
| 5 | (dimethylaminopropoxy-pyridinyl) | (piperidinyl) | (M + 1) 430.38 | DMSO-d$_6$: δ 9.33-9.26 (m, 1H), 8.52 (d, J = 2.2 Hz, 1H), 8.06 (dd, J = 8.6, 2.5 Hz, 1H), 7.88 (dd, J = 9.5, 1.5 Hz, 1H), 7.79 (d, J = 9.5 Hz, 1H), 7.55 (d, J = 8.1 Hz, 1H), 7.44 (t, J = 7.9 Hz, 1H), 7.12 (d, J = 7.5 Hz, 1H), 7.00 (d, J = 8.6 Hz, 1H), 4.35 (t, J = 6.6 Hz, 2H), 3.29-3.24 (m, 2H), 2.79 (t, J = 11.0 Hz, 2H), 2.37 (t, J = 7.1 Hz, 2H), 2.16 (s, 6H), 1.93-1.70 (m, 7H), 1.45-1.36 (m, 1H). |
| 6 | (dimethylaminopropoxy-pyridinyl) | (morpholinyl) | (M + 1) 432.22 | DMSO-d$_6$: δ 9.38 (s, 1H), 8.55 (d, J = 2.4 Hz, 1H), 8.09 (dd, J = 8.6, 2.6 Hz, 1H), 7.91 (dd, J = 9.5, 1.8 Hz, 1H), 7.80 (d, J = 9.5 Hz, 1H), 7.60 (d, J = 8.0 Hz, 1H), 7.48 (t, J = 7.9 Hz, 1H), 7.18 (d, J = 5.7 Hz, 1H), 7.02 (d, J = 8.6 Hz, 1H), 4.38 (t, J = 6.4 Hz, 2H), 4.05-3.94 (m, 2H), 3.81 (t, J = 10.5 Hz, 2H), 3.19-3.12 (m, 2H), 3.03 (t, J = 10.4 Hz, 2H), 2.73 (t, J = 7.2 Hz, 2H), 2.43 (s, 6H), 2.06-1.94 (m, 2H). |

| Example | Ar | R$_1$ | LC-MS (ESI) | $^1$H NMR, 400 MHz |
|---|---|---|---|---|
| 7 | [structure: dimethylamino-propoxy-pyridine] | [structure: N-methylpiperazine] | (M + 1) 445.49 | DMSO-d$_6$: δ 9.23 (s, 1H), 8.59 (d, J = 2.2 Hz, 1H), 8.19-8.10 (m, 2H), 7.99 (d, J = 9.5 Hz, 1H), 7.71 (d, J = 8.2 Hz, 1H), 7.62 (t, J = 7.9 Hz, 1H), 7.31 (d, J = 7.7 Hz, 1H), 7.04 (d, J = 8.6 Hz, 1H), 4.41 (t, J = 6.1 Hz, 2H), 3.73-3.66 (m, 2H), 3.57-3.44 (m, 4H), 3.29-3.17 (m, 4H), 2.95 (s, 3H), 2.84 (d, J = 4.5 Hz, 6H), 2.20-2.12 (m, 2H). |
| 8 | [structure: dimethylamino-propoxy-pyridine] | [structure: 2,5-dimethylpiperazine] | (M + 1) 473.24 | CDCl$_3$: δ 9.45-9.40 (m, 1H), 8.38 (d, J = 2.3 Hz, 1H), 7.85-7.77 (m, 2H), 7.71 (d, J = 8.0 Hz, 1H), 7.61 (dd, J = 9.5, 1.9 Hz, 1H), 7.50-7.44 (m, 1H), 7.13 (d, J = 7.4 Hz, 1H), 6.89 (d, J = 8.6 Hz, 1H), 4.47 (t, J = 6.0 Hz, 2H), 3.20-3.13 (m, 2H), 3.12-3.05 (m, 2H), 2.98 (t, J = 11.3 Hz, 2H), 2.77-2.69 (m, 8H), 2.48 (s, 3H), 2.31-2.23 (m, 2H), 1.26 (d, J = 6.3 Hz, 6H). |

Example 9

N,N-dimethyl-3-((5-(9-(1H-imidazol-1-yl)benzo[4,5]imidazo[1,2-a]pyridin-2-yl)pyridin-2-yl)oxy)propan-1-amine a) 2,6-Dinitroiodobenzene: sodium nitrite (1.75 g, 25.4 mmol) was added into concentrated sulfuric acid (19 mL). The mixture was heated to 70° C., and cooled to room temperature after sodium nitrite was completely dissolved. 2,6-Dinitroaniline (4.2 g, 22.9 mmol) was dissolved in acetic acid (40 mL), then the above solution of sodium nitrite in concentrated sulfuric acid was added dropwise while the temperature was controlled to be no more than 40° C. After reaction for 30 min, the temperature of the reaction solution was raised to 70° C., and a solution of potassium iodide (4.2 g, 25.4 mmol) in water (40 mL) was added dropwise slowly. After reaction for 30 min, the reaction solution was poured into ice water (150 mL). Solid precipitated. After suction filtration and drying, the target compound (5.2 g, 78% yield, yellow solid) was obtained. $^1$H NMR (400 MHz, CDCl$_3$): δ 7.84 (d, J=8.0 Hz, 2H), 7.67 (t, J=8.0 Hz, 1H).

b) 2-Iodo-3-nitroaniline: 2,6-dinitroiodobenzene (5.2 g, 17.7 mmol) was dissolved in acetic acid (50 mL), and then reduced iron powder (3.0 g, 53.1 mmol) was added. The mixture was allowed to react at 75° C. for 30 min. After the reaction was completed, the reaction solution was poured into water. The resulting mixture was extracted with dichloromethane (100 mL×3). The organic phase was dried with anhydrous sodium sulfate, and concentrated by removing the organic solvent at reduced pressure to obtain a crude product. Isolation and purification by column chromatography (silica gel column, 0-50% ethyl acetate/petroleum ether as a mobile phase) were performed to obtain the target compound (2.4 g, 52% yield, orange solid). LC-MS (ESI) m/z (M+1) 264.93.

c) 2-Bromo-9-nitrobenzo[4,5]imidazo[1,2-a]pyridine: at room temperature, 2-iodo-3-nitroaniline (2.4 g, 9.1 mmol), 2-iodo-5-bromopyridine (3.4 g, 11.83 mmol), cuprous iodide (347 mg, 1.82 mmol), 1,10-phenanthroline (328 mg, 2.82 mmol) and cesium carbonate (5.9 g, 18.2 mmol) were added into anhydrous xylene (25 mL). The atmosphere in the reaction system was replaced with nitrogen three times. After microwave reaction at 100° C. for 14 hours, the reaction mixture was cooled to room temperature, and concentrated by removing the organic solvent at reduced pressure to obtain a crude product. Isolation and purification by column chromatography (silica gel column, 0-60% ethyl acetate/petroleum ether as a mobile phase) were performed to obtain the target compound (1.3 g, 49% yield, yellow solid). LC-MS (ESI): m/z (M+1) 291.93.

d) 2-Bromobenzo[4,5]imidazo[1,2-a]pyridin-9-amine: at room temperature, 2-bromo-9-nitrobenzo[4,5]imidazo[1,2-a]pyridine (1.2 g, 4.16 mmol) was dissolved in ethanol (15 mL) and water (15 mL), then ammonium chloride (2.19 g, 41.6 mmol) and reduced iron powder (1.39 g, 24.96 mmol) were added sequentially. The resulting mixture was allowed to react at room temperature for 14 hours. After the reaction was completed, the reaction solution was filtered. The filtrate was extracted with dichloromethane (100 mL×3). The organic phase was dried with anhydrous sodium sulfate, and concentrated by removing the organic solvent at reduced pressure to obtain a crude product. Isolation and purification by column chromatography (silica gel column, 0-70% ethyl acetate/petroleum ether as a mobile phase) were performed to obtain the target compound (656 mg, 61% yield, orange solid). LC-MS (ESI): m/z (M+1) 261.98.

e) 2-Bromo-9-(1H-imidazol-1-yl)benzo[4,5]imidazo[1,2-a]pyridine: at room temperature, 2-bromobenzo[4,5]imidazo[1,2-a]pyridin-9-amine (140 mg, 0.50 mmol)), glyoxal (154 mg, 2.66 mmol), formaldehyde (147 mg, 49 mmol) and ammonium chloride (266 mg, 4.9 mmol) were added into methanol (3 mL). The atmosphere in the reaction system was replaced with nitrogen three times. After the reaction mixture was allowed to react at 65° C. for 3 hours, phosphoric acid was added to continue the reaction for another 14 hours. The reaction mixture was cooled to room temperature, and concentrated by removing the organic solvent at reduced pressure to obtain a crude product. Isolation and purification with preparative silica gel plate (0-15% methanol/dichloromethane as a mobile phase) were performed to obtain the target compound (75 mg, 51% yield). LC-MS (ESI): m/z (M+1) 312.92.

f) N,N-Dimethyl-3-((5-(9-(1H-imidazol-1-yl)benzo[4,5]imidazo[1,2-a]pyridin-2-yl)pyridin-2-yl)oxy)propan-1-amine: it was prepared using a synthetic process similar to that described in Example 3g, wherein the starting materials were 2-bromo-9-(1H-imidazol-1-yl)benzo[4,5]imidazo[2-a]pyridine and (6-(3-(dimethylamino)propyl)pyridin-3-yl)boronic acid pinacol ester. After purification, the target compound (8 mg, 7.5% yield) was obtained.

Example 10

N,N-dimethyl-3-((5-(9-(morpholinomethyl)benzo[4,5]imidazo[1,2-a]pyridin-2-yl)pyridin-2-yl)oxy)propan-1-amine a) Methyl 2-bromobenzo[4,5]imidazo[1,2-a]pyridin-9-carboxylate: at room temperature, methyl 3-amino-2-bromobenzoate (4.5 g, 19.56 mmol), 2,5-dibromopyridine (6.0 g, 25.43 mmol), cuprous iodide (1.5 g, 7.8 mmol), 1,10-phenanthroline (2.82 g, 15.65 mmol) and cesium carbonate (19.1 g, 58.68 mmol) were added into anhydrous toluene (50 mL). The atmosphere in the reaction system was replaced with nitrogen three times. After microwave reaction at 100° C. for 14 hours, the reaction mixture was cooled to room temperature, and concentrated by removing the organic solvent at reduced pressure. The resulting crude product was subjected to isolation and purification with a chromatographic column (silica gel column, 0-50% ethyl acetate/petroleum ether as a mobile phase) to obtain the target compound (2.3 g, 39% yield). LC-MS (ESI): (M+1) 304.93.

b) (2-Bromobenzo[4,5]imidazo[1,2-a]pyridin-9-yl)benzyl alcohol: methyl 2-bromobenzo[4,5]imidazo[1,2-a]pyridin-9-carboxylate (2.3 g, 7.54 mmol) was dissolved in methanol (30 mL), and sodium borohydride (1.43 g, 37.71 mmol) was added in batches in an ice-water bath. After the reaction mixture reacted at 0° C. for 2 hours, the reaction was quenched with a sodium bicarbonate saturated solution. The mixed solution was extracted with dichloromethane (40 mL×3), and concentrated by removing the organic solvent at reduced pressure to obtain a crude product. Isolation and purification with column chromatography (silica gel column, 0-50% methanol/dichloromethane as a mobile phase) were performed to obtain the target compound (1.2 g, 58% yield). LC-MS (ESI): (M+1) 277.01.

c) 2-Bromobenzo[4,5]imidazo[1,2-a]pyridine-9-carbaldehyde: (2-bromobenzo[4,5]imidazo[1,2-a]pyridin-9-yl)benzyl alcohol (600 mg, 2.17 mmol) was dissolved in dichloromethane (5 mL) and N,N-dimethylformamide (5 mL), and manganese dioxide (3.77 g, 43.3 mmol) was added in batches in an ice-water bath. After reaction under agitation at room temperature for 14 hours, the reaction mixture was filtered, and concentrated by removing the organic solvent at reduced pressure to obtain the target compound (530 mg, 89% yield). LC-MS (ESI): (M+1) 274.95.

d) 4-((4-Bromobenzo[4,5]imidazo[1,2-a]pyridin-9-yl)methyl)morpholine: at room temperature, 2-bromobenzo[4,5]imidazo[1,2-a]pyridine-9-carbaldehyde (220 mg, 0.80 mmol) and morpholine (140 mg, 1.60 mmol) were sequentially dissolved in tetrahydrofuran (5 mL), and then tetraisopropyl titanate (682 mg, 2.40 mmol) was added. After reaction at 60° C. for 4 hours, the reaction mixture was cooled to room temperature, and sodium borohydride (152 mg, 4.0 mmol) was added in batches. The reaction mixture continued to react at room temperature for 2 hours. The reaction solution was diluted with ethyl acetate (20 mL), and the reaction was quenched with a saturated sodium bicarbonate solution (30 mL). The reaction solution was filtered to remove the solid, and then concentrated by removing the organic solvent at reduced pressure to obtain a crude product. Isolation and purification with column chromatography (silica gel column, 0-60% methanol/dichloromethane as a mobile phase) were performed to obtain the target compound (160 mg, 58% yield). LC-MS (ESI): (M+1) 346.05.

e) N,N-Dimethyl-3-((5-(9-(morpholinomethyl)benzo[4,5]imidazo[1,2-a]pyridin-2-yl)pyridin-2-yl)oxy)propan-1-amine: it was prepared using a synthetic process similar to that described in Example 3g, wherein the starting materials were 4-((2-bromobenzo[4,5]imidazo[1,2-a]pyridin-9-yl)methyl)morpholine and (6-(3-(dimethylamino)propyl)pyridin-3-yl)boronic acid pinacol ester. After purification, the target compound (31 mg, 17% yield, white solid) was obtained.

Example 11

N,N-dimethyl-3-((5-(9-(4-methylpiperazin-1-yl)methyl)benzo[4,5]imidazo[1,2-a]pyridin-2-yl)pyridin-2-yl)oxy)propan-1-amine The target compound was prepared using a synthetic process similar to Example 10 d-e, wherein the starting materials were 2-bromobenzo[4,5]imidazo[1,2-a]pyridine-9-carbaldehyde, N-methylpiperazine and (6-(3-(dimethylamino)propyl)pyridin-3-yl) boronic acid pinacol ester.

Example 12

N,N-dimethyl-3-((5-(9-(1-methylpiperidin-4-yl)oxy)benzo[4,5]imidazo[1,2-a]pyridin-2-yl)pyridin-2-yl)oxy)propan-1-amine a) 2-Bromobenzo[4,5]imidazo[1,2-a]pyridine-9-phenol: trifluoroacetic acid (40 mL) was added into 9-benzyloxy-2-bromobenzo[4,5]imidazo[1,2-a]pyridine (Example 1d, 4 g, 11.36 mmol). The reactants were allowed to react at 70° C. for 3 hours, and then cooled to room temperature. The reactants were concentrated, and then adjusted to be weakly alkaline (pH ~8) with a saturated sodium bicarbonate solution. Extraction was performed with ethyl acetate (100 mL×2). The organic phases were combined, washed with a saturated saline solution, dried with anhydrous sodium sulfate, suction filtered, and concentrated by removing the organic solvent at reduced pressure to obtain a crude product. Isolation and purification by column chromatography (silica gel, dichloromethane: methanol=15:1 as an eluant) were performed to obtain the target compound (2.0 g, 67.2% yield, black solid). LC-MS (ESI): m/z (M+1) 262.99.

b) Tert-butyl 4-((2-bromobenzo[4,5]imidazo[1,2-a]pyridin-9-yl)oxy)piperidine-1-carboxylate: 2-bromobenzo[4,5]imidazo[1,2-a]pyridin-9-phenol (800 mg, 3.05 mmol), tert-butyl 4-(tosyloxy)piperidine-1-carboxylate (1.3 g, 3.66 mmol) and potassium carbonate (837 mg, 6.10 mmol) were dissolved in N,N-dimethylformamide (20 mL). The resulting mixture was allowed to react under agitation at 70° C. for 2 hours, and then cooled to room temperature. Water (20 mL) was added. Extraction was performed with ethyl acetate (50 mL×2). The organic phase was washed with a saturated saline solution (50 mL×2), dried with anhydrous sodium sulfate, filtered, and concentrated at reduced pressure to obtain a crude product. Isolation and purification by column chromatography (silica gel, dichloromethane: methanol=20:1 as an eluant) were performed to obtain the target compound (220 mg, 16.2% yield, yellow solid). LC-MS (ESI): m/z (M+1) 446.10.

c) 9-(Piperidin-4-oxo)-2-bromobenzo[4,5]imidazo[1,2-a]pyridine: tert-butyl 4-((2-bromobenzo[4,5]imidazo[1,2-a]pyridin-9-yl)oxy)piperidin-1-carboxylate (220 mg, 0.49 mmol) was added into a solution of HCl in 1,4-dioxane (2 mL) and methanol (2 mL). After reaction under agitation at ambient temperature for 20 min, the reaction mixture was spin-dried to obtain a crude product (150 mg, 88.2% yield, yellow solid). LC-MS (ESI): m/z (M+1) 346.00.

d) 9-(1-Methylpiperidin-4-oxo)-2-bromobenzo[4,5]imidazo[1,2-a]pyridine: 9-(piperidin-4-oxy)-2-bromobenzo[4,5]imidazo[1,2-a]pyridine (150 mg, 0.43 mmol) and paraformaldehyde (65 mg, 2.17 mmol) were added into formic acid (5 mL). After agitated at 70° C. overnight, the reaction mixture was cooled to room temperature. The reaction mixture was then adjusted to be weakly alkaline (pH 8) with a saturated sodium bicarbonate solution Extraction was performed with ethyl acetate (10 mL×2). The organic phases were combined, washed with a saturated saline solution (10 mL×2), dried with anhydrous sodium sulfate, suction filtered, and concentrated by removing the organic solvent at reduced pressure to obtain a crude product. Isolation and purification by column chromatography (silica gel, methylene dichloride:methanol=10:1 as an eluant) were performed to obtain the target compound (80 mg, 51.3% yield, yellow solid). LC-MS (ESI): m/z (M+1) 360.05.

e) N,N-dimethyl-3-((5-(9-((1-methylpiperidin-4-yl))oxy)benzo[4,5]imidazo[1,2-a] pyridin-2-yl)pyridin-2-yl)oxy)propan-1-amine: it was prepared using a synthetic process similar to that described in Example 3g, wherein the starting materials were 9-(1-methylpiperidin-4-oxy)-2-bromobenzo[4,5]imidazo[1,2-a]pyridine and N,N-dimethyl-3-((5-(4,4,5,5-tetramethyl-1,3,2-dioxaborolan-2-yl)pyridin-2-yl)oxy)propan-1-amine, and purification was performed to obtain the target compound (5 mg, 4.9% yield, white solid).

Example 13 was prepared using a synthetic process similar to that described in Examples 12b and e, wherein the starting materials were 2-bromobenzo[4,5]imidazo[1,2-a]pyrimidine-9-phenol (Example 12a), tetrahydro-2H-pyran-4-yl-4-toluene sulfonate and N,N-dimethyl-3-((5-(4,4,5,5-tetramethyl-1,3,2-dioxaborolan-2-yl)pyridin-2-yl)oxy)propan-1-amine.

Example 14

N,N-dimethyl-3-((5-(9-(tetrahydro-2H-pyran-4-ylamino)benzo[4,5]imidazo[1,2-a]pyridin-2-yl)pyridin-2-yl)oxy)propan-1-amine a) 2-Bromo-N-(tetrahydro-2H-pyran-4-yl)benzo[4,5]imidazo[1,2-a]pyridin-9-amine: at room temperature, 2-bromobenzo[4,5]imidazo[1,2-a]pyridin-9-amine (Example 9d, 300 mg, 1.14 mmol) and tetrahydropyran-4-one (229 mg, 2.28 mmol) were sequentially added into tetrahydrofuran (4 mL) and acetic acid (2 mL), and finally a 1 mol/L borane solution in tetrahydrofuran (2.3 mL, 2.28 mmol) was added dropwise slowly within 10 minutes. After the reaction solution was agitated overnight at room temperature, the reaction was quenched with methanol (10 mL). The reaction solution was concentrated by removing the organic solvent at reduced pressure to obtain a crude product which was isolated and purified by column chromatography (silica gel, 0-10% methanol/dichloromethane) to obtain the target compound (270 mg, 68% yield). LC-MS (ESI): m/z (M+1) 346.02.

b) The title compound was prepared using a synthetic process similar to that described in Example 3g, wherein the starting materials were 2-bromo-N-(tetrahydro-2H-pyran-4-yl)benzo[4,5]imidazo[1,2-a]pyridin-9-amine and N,N-dimethyl-3-((5-(4,4,5,5-tetramethyl-1,3,2-dioxaborolan-2-yl)pyridin-2-yl)oxy)propan-1-amine.

Example 15 was prepared using a synthetic process similar to that described in Example 14, wherein the starting materials were 2-bromobenzo[4,5]imidazo[1,2-a]pyridin-9-amine (Example 9d), 1-methylpiperidin-4-one and N,N-dimethyl-3-((5-(4,4,5,5-tetramethyl-1,3,2-dioxaborolan-2-yl)pyridin-2-yl)oxy)propan-1-amine.

Examples 16-17 were prepared using a synthetic process similar to that described in Example 3, wherein the starting materials were 3-chloro-2-nitroaniline, morpholine, potassium iodide, cuprous bromide, 2-amino-5-bromopyridine and corresponding boronic acid or boronic acid pinacol ester.

Examples 18-23 were prepared using a synthetic process similar to that described in Example 1, wherein the starting materials were 9-benzyloxy-2-bromobenzo[4,5]imidazo[1,2-a]pyridine (Example 1d) and corresponding boronic acid or boronic acid pinacol ester.

Example 24 was prepared using a synthetic process similar to that described in Example 12e, wherein the starting materials were 9-(piperidin-4-oxy)-2-bromobenzo[4,5]imidazo[1,2-a]pyridine (Example 12c) and N,N-dimethyl-3-((5-(4,4,5,5-tetramethyl-1,3,2-dioxaborolan-2-yl)pyridin-2-yl)oxy)propan-1-amine.

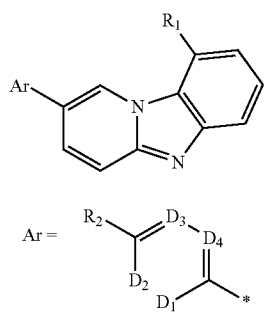

| Example | Ar | $R_1$ | LC-MS (ESI) | $^1$H NMR, 400 MHz |
|---|---|---|---|---|
| 9 | ![Ar structure with dimethylamino-propoxy-pyridinyl group] | ![imidazolyl group] | (M + 1) 413.19 | DMSO-$d_6$: δ 8.24 (d, J = 2.4 Hz, 1H), 8.14 (s, 1H), 8.04-7.99 (m, 1H), 7.94 (dd, J = 9.6, 1.8 Hz, 1H), 7.85 (dd, J = 9.6, 0.7 Hz, 1H), 7.78 (dd, J = 8.6, 2.6 Hz, 1H), 7.76-7.72 (m, 1H), 7.68-7.62 (m, 1H), 7.47 (dd, J = 7.5, 0.7 Hz, 1H), 7.37 (s, 1H), 7.02 (s, 1H), 6.93 (d, J = 8.7 Hz, 1H), 4.33 (t, J = 6.6 Hz, 2H), 2.48-2.44 (m, 2H), 2.24 (s, 6H), 1.94-1.87 (m, 2H). |

-continued

| Example | Ar | R$_1$ | LC-MS (ESI) | $^1$H NMR, 400 MHz |
|---|---|---|---|---|
| 10 | 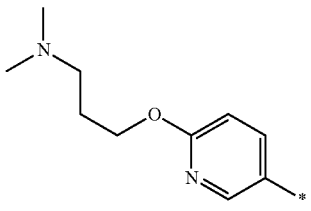 [SMILES: *c1ccc(OCCCN(C)C)nc1] | 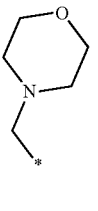 | (M + 1) 446.06 | DMSO-d$_6$: δ 9.51 (s, 1H), 8.58 (s, 1H), 8.10 (d, J = 8.6 Hz, 1H), 7.92 (d, J = 9.5 Hz, 1H), 7.82-7.73 (m, 2H), 7.48-7.38 (m, 1H), 7.24 (d, J = 6.1 Hz, 1H), 7.00-6.93 (m, 1H), 4.34 (t, J = 6.6 Hz, 2H), 4.12 (s, 2H), 3.53-3.44 (m, 4H), 2.53-2.50 (m, 4H), 2.37 (t, J = 7.1 Hz, 2H), 2.16 (s, 6H), 1.92-1.84 (m, 2H). |
| 11 | 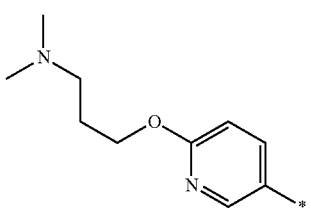 | 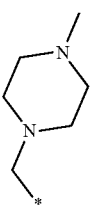 | (M + 1) 459.10 | DMSO-d$_6$: δ 9.47 (s, 1H), 8.60 (d, J = 2.1 Hz, 1H), 8.13 (dd, J = 8.6, 2.3 Hz, 1H), 7.92 (d, J = 9.4 Hz, 1H), 7.82-7.72 (m, 2H), 7.47-7.40 (m, 1H), 7.23 (d, J = 7.1 Hz, 1H), 6.97 (d, J = 8.6 Hz, 1H), 4.35 (t, J = 6.6 Hz, 2H), 4.10 (s, 2H), 2.60-2.51 (m, 4H), 2.39 (t, J = 7.1 Hz, 2H), 2.35-2.10 (m, 10H), 2.06 (s, 3H), 1.93-1.85 (m, 2H). |
| 12 | 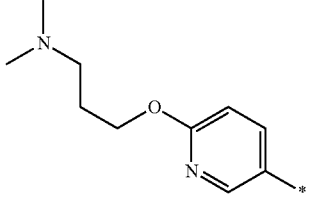 [SMILES: *c1ccc(OCCCN(C)C)nc1] | 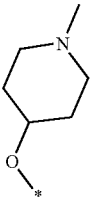 | (M + 1) 460.37 | CDCl$_3$: δ 9.31 (s, 1H), 8.40 (d, J = 2.4 Hz, 1H), 7.82 (dd, J = 8.6, 2.6 Hz, 1H), 7.75 (d, J = 9.5 Hz, 1H), 7.62 (dd, J = 9.5, 1.8 Hz, 1H), 7.52 (d, J = 8.2 Hz, 1H), 7.41 (t, J = 8.1 Hz, 1H), 6.87 (d, J = 8.6 Hz, 1H), 6.82 (d, J = 7.9 Hz, 1H), 4.81-4.69 (m, 1H), 4.44 (t, J = 6.3 Hz, 2H), 2.89-2.70 (m, 4H), 2.49 (s, 6H), 2.38 (s, 3H), 2.27-2.05 (m, 8H). |
| 13 | 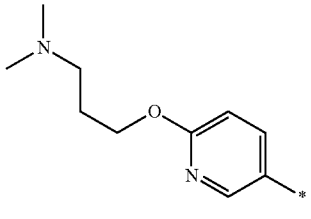 [SMILES: *c1ccc(OCCCN(C)C)nc1] | 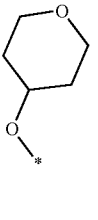 | (M + 1) 447.10 | CDCl$_3$: δ 9.29 (dd, J = 1.7, 0.9 Hz, 1H), 8.40 (d, J = 2.2 Hz, 1H), 7.80 (dd, J = 8.6, 2.6 Hz, 1H), 7.75 (d, J = 9.4 Hz, 1H), 7.62 (dd, J = 9.5, 1.9 Hz, 1H), 7.53 (d, J = 8.1 Hz, 1H), 7.41 (t, J = 8.1 Hz, 1H), 6.89 (d, J = 8.6 Hz, 1H), 6.82 (d, J = 7.9 Hz, 1H), 4.92-4.83 (m, 1H), 4.43 (t, J = 6.4 Hz, 2H), 4.10-4.02 (m, 2H), 3.71-3.68 (m, 2H), 2.61-2.56 (m, 2H), 2.38-2.21 (m, 8H), 2.08-1.96 (m 4H). |
| 14 | 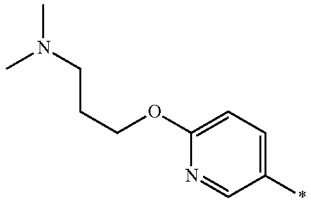 [SMILES: *c1ccc(OCCCN(C)C)nc1] | 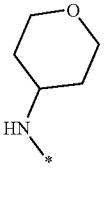 | (M + 1) 446.13 | DMSO-d$_6$: δ 9.31 (s, 1H), 8.64-8.58 (m, 1H), 8.18-8.10 (m, 1H), 7.86 (d, J = 9.5 Hz, 1H), 7.75-7.69 (m, 1H), 7.35-7.28 (m, 1H), 7.22 (d, J = 8.0 Hz, 1H), 7.04-6.97 (m, 1H), 6.79 (d, J = 7.7 Hz, 1H), 5.82 (d, J = 5.8 Hz, 1H), 4.43-4.34 (m, 2H), 3.97-3.90 (m, 2H), 3.72-3.66 (m, 1H), 3.57-3.42 (m, 4H), 2.26 (s, 6H), 2.08-2.02 (m, 2H), 1.97-1.87 (m, 2H), 1.71-1.61 (m, 2H). |
| 15 | 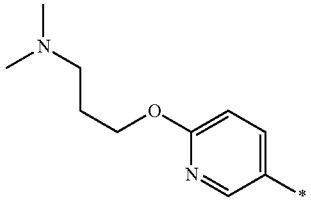 [SMILES: *c1ccc(OCCCN(C)C)nc1] | 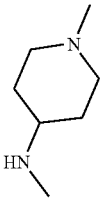 | (M + 1) 459.08 | DMSO-d$_6$: δ 9.31 (s, 1H), 8.59 (d, J = 2.3 Hz, 1H), 8.12 (dd, J = 8.6, 2.6 Hz, 1H), 7.85 (dd, J = 9.5, 1.6 Hz, 1H), 7.71 (d, J = 9.4 Hz, 1H), 7.32 (t, J = 7.9 Hz, 1H), 7.21 (d, J = 8.0 Hz, 1H), 6.99 (d, J = 8.6 Hz, 1H), 6.75 (d, J = 7.7 Hz, 1H), 5.74 (d, J = 5.8 Hz, 1H), 4.35 (t, J = 6.6 Hz, 2H), 2.82-2.75 (m, 2H), 2.39 (t, J = 7.1 Hz, 2H), 2.25-2.09 (m, 10H), 2.08-1.94 (m, 4H), 1.93-1.85 (m, 2H), 1.73-1.63 (m, 2H). |
| 16 | 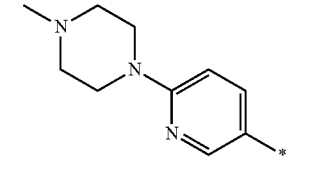 [SMILES: *c1ccc(N2CCN(C)CC2)nc1] | 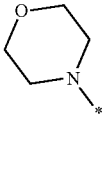 | (M + 1) 429.25 | CDCl$_3$: δ 9.48 (s, 1H), 8.49 (d, J = 2.4 Hz, 1H), 7.93 (d, J = 9.5 Hz, 1H), 7.80 (dd, J = 8.8, 2.5 Hz, 1H), 7.76 (d, J = 8.2 Hz, 1H), 7.70 (dd, J = 9.4, 1.5 Hz, 1H), 7.53 (t, J = 8.0 Hz, 1H), 7.17 (d, J = 7.7 Hz, 1H), 6.86 (d, J = 8.8 Hz, 1H), 4.20-3.82 (m, 8H), 3.37-3.09 (m, 8H), 2.85 (s, 3H). |

-continued

| Example | Ar | R₁ | LC-MS (ESI) | ¹H NMR, 400 MHz |
|---|---|---|---|---|
| 17 | (2,5-dimethyl-4-methylpiperazin-1-yl)pyridin-5-yl | morpholin-4-yl | (M + 1) 457.26 | CDCl₃: δ 9.43 (s, 1H), 8.47 (d, J = 2.3 Hz, 1H), 7.80 (d, J = 9.4 Hz, 1H), 7.76 (dd, J = 8.8, 2.6 Hz, 1H), 7.73 (d, J = 7.7 Hz, 1H), 7.63 (dd, J = 9.5, 1.9 Hz, 1H), 7.49 (t, J = 8.0 Hz, 1H), 7.12 (d, J = 7.3 Hz, 1H), 6.82 (d, J = 8.8 Hz, 1H), 4.30-4.23 (m, 2H), 4.11-4.07 (m, 2H), 3.98-3.92 (m, 2H), 3.24-3.07 (m, 6H), 2.90-2.75 (m, 2H), 2.61 (s, 3H), 1.43 (d, J = 3.3 Hz, 6H). |
| 18 | 5-(3-dimethylaminopropoxy)pyridin-2-yl | 3,6-dihydro-2H-pyran-4-yl | M.W. 428.54 | — |
| 19 | 5-(4-methylpiperazin-1-yl)pyridin-2-yl | 3,6-dihydro-2H-pyran-4-yl | M.W. 425.54 | — |
| 20 | 5-(2,6-dimethyl-4-methylpiperazin-1-yl)pyridin-2-yl | 3,6-dihydro-2H-pyran-4-yl | M.W. 453.59 | — |
| 21 | 5-(3-dimethylaminopropoxy)pyridin-2-yl | tetrahydro-2H-pyran-4-yl | M.W. 430.55 | — |
| 22 | 5-(3-dimethylaminopropoxy)pyridin-2-yl | 1-methylpiperidin-4-yl | M.W. 443.60 | — |
| 23 | 5-(3-dimethylaminopropoxy)pyridin-2-yl | 1H-imidazol-4-yl | M.W. 412.50 | — |

| Example | Ar | $R_1$ | LC-MS (ESI) | $^1$H NMR, 400 MHz |
|---|---|---|---|---|
| 24 | (structure) | (structure) | M.W. 445.57 | — |

Examples 25-32 were prepared using a synthetic process similar to that described in Example 1d-1h, wherein the starting materials were 3-(benzyloxy)-2-iodoaniline (Example 1c), 5-bromo-2-iodopyrimidine or 2-bromo-5-iodopyrazine or 3-bromo-6-iodopyridazine, 6-(3-(dimethylamino)propoxy-3-pyridinyl)boronic acid and corresponding heterocyclic boronic acid pinacol esters.

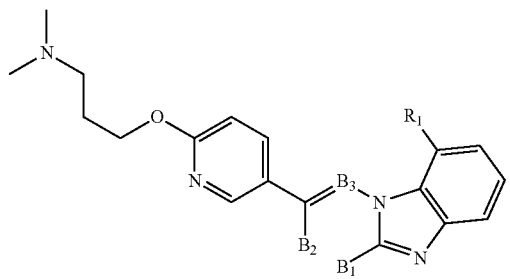

| Example | $B_1$ | $B_2$ | $B_3$ | $R_1$ | M.W. |
|---|---|---|---|---|---|
| 25 | N | CH | CH | (structure) | 429.52 |
| 26 | N | CH | CH | (structure) | 431.54 |
| 27 | N | CH | CH | (structure) | 432.53 |
| 28 | CH | N | CH | (structure) | 429.52 |
| 29 | CH | N | CH | (structure) | 431.54 |
| 30 | CH | N | CH | (structure) | 432.53 |
| 31 | CH | CH | N | (structure) | 429.52 |
| 32 | CH | CH | N | (structure) | 432.53 |

Examples 33-38 were prepared using a synthetic process similar to that described in Example 1, wherein the starting materials were corresponding substituted pyridines, 5-bromo-2-iodopyridine, 6-(3-(dimethylamino)propoxy-3-pyridinylboronic acid and corresponding heterocyclic boronic acid pinacol esters.

| Example | $A_1$ | $A_2$ | $A_3$ | $R_1$ | M.W. |
|---|---|---|---|---|---|
| 33 | N | CH | CH | (structure) | 429.52 |

| Example | A₁ | A₂ | A₃ | R₁ | M.W. |
|---|---|---|---|---|---|
| 34 | N | CH | CH | 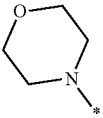 | 432.53 |
| 35 | CH | N | CH | 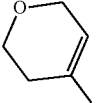 | 429.52 |
| 36 | CH | N | CH | 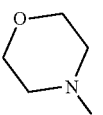 | 432.53 |
| 37 | CH | CH | N | 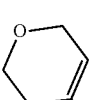 | 429.52 |
| 38 | CH | CH | N | 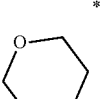 | 432.53 |

Examples 39-40 were prepared using a synthetic process similar to that described in Example 1 e-h, and the starting materials were 9-(benzyloxy)-2-bromobenzo[4,5]imidazo[1,2-a]pyridine (Example 1d), 4-(3-(dimethylamino)propoxy)phenylboronic acid or 6-(3-(dimethylamino)propoxy)-3-pyridinylboronic acid, and 3,6-dihydro-2H-pyran-4-boronic acid pinacol ester.

Example 41 was prepared using a synthetic process similar to that described in Example 4, and the starting materials were 2-(4-(4-(dimethylamino)piperidin-1-yl)phenyl)benzo[4,5]imidazo[1,2-a]pyridin-9-yl trifluoromethanesulfonate (the intermediate in Example 39) and morpholine.

Examples 42-68 were prepared using a synthetic process similar to that described in Example 3, wherein the starting materials were 3-chloro-2-nitroaniline, corresponding N-containing heterocycles, potassium iodide, cuprous bromide, 2-amino-5-bromopyridine and corresponding boronic acid pinacol esters.

Examples 69-70 were prepared using a synthetic process similar to that described in Example 12e, wherein the starting materials were 9-(1-methylpiperidin-4-oxo)-2-bromobenzo[4,5]imidazo[1,2-a] pyridine and corresponding boronic acid pinacol esters.

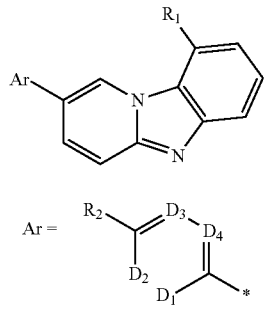

| Example | Ar | R₁ | LC-MS (ESI) | ¹H NMR, 400 MHz |
|---|---|---|---|---|
| 39 | 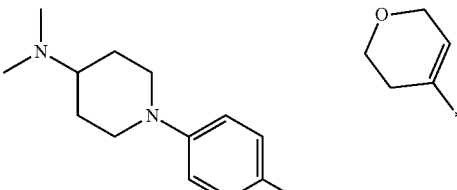 | 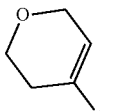 | (M + 1) 453.45 | CDCl₃: δ 8.90 (s, 1H), 7.87 (d, J = 7.6 Hz, 1H), 7.78-7.74 (m, 1H), 7.70 (dd, J = 9.5, 1.7 Hz, 1H), 7.52-7.46 (m, 3H), 7.10 (dd, J = 7.2, 0.8 Hz, 1H), 7.05 (d, J = 8.8 Hz, 2H), 6.05-6.01 (m, 1H), 4.44 (d, J = 2.4 Hz, 2H), 4.09 (t, J = 5.4 Hz, 2H), 3.93-3.87 (m, 2H), 3.04-2.98 (m, 1H), 2.85 (t, J = 11.6 Hz, 2H), 2.65 (s, 6H), 2.58-2.54 (m, 2H), 2.19-2.16 (m, 2H), 1.89-1.82 (m, 2H). |
| 40 | 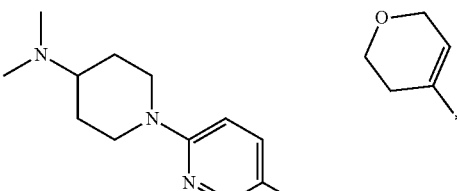 | 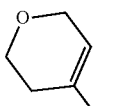 | (M/2 + 1) 227.82 | CDCl₃: δ 9.03 (s, 1H), 8.43 (d, J = 2.4 Hz, 1H), 8.24-8.19 (m, 1H), 7.99 (d, J = 8.4 Hz, 1H), 7.95-7.91 (m, 1H), 7.73 (dd, J = 9.2, 2.8 Hz, 1H), 7.66-7.62 (m, 1H), 7.26-7.24 (m, 1H), 6.84 (d, J = 8.7 Hz, 1H), 6.11 (s, 1H), 4.68-4.62 (m, 2H), 4.47-4.43 (m, 2H), 4.13-4.07 (m, 2H), 3.39-3.35 (m, 1H), 3.01-2.95 (m, 2H), 2.81 (s, 6H), 2.58-2.54 (m, 2H), 2.33-2.28 (m, 2H), 1.84-1.81 (m, 2H). |
| 41 | 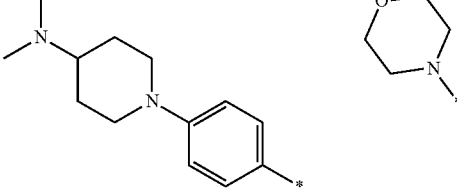 | 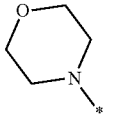 | (M/2 + 1) 228.95 | CDCl₃: δ 9.44 (s, 1H), 7.81-7.66 (m, 3H), 7.53 (d, J = 8.8 Hz, 2H), 7.48 (t, J = 7.9 Hz, 1H), 7.11 (d, J = 7.2 Hz, 1H), 7.06 (d, J = 8.4 Hz, 2H), 4.12-4.06 (m, 2H), 4.02-3.88 (m, 4H), 3.22-3.08 (m, 5H), 2.87 (t, J = 11.6 Hz, 2H), 2.72 (s, 6H), 2.26-2.22 (m, 2H), 1.95-1.87 (m, 2H). |

| Example | Ar | R₁ | LC-MS (ESI) | ¹H NMR, 400 MHz |
|---|---|---|---|---|
| 42 | (4-dimethylamino-piperidinyl pyridine) | (morpholine) | (M + 1) 457.26 | CDCl₃: δ 9.41 (d, J = 0.8 Hz, 1H), 8.46 (d, J = 2.4 Hz, 1H), 7.78-7.70 (m, 3H), 7.62 (dd, J = 9.5, 1.9 Hz, 1H), 7.48 (t, J = 8.0 Hz, 1H), 7.11 (d, J = 7.2 Hz, 1H), 6.83 (d, J = 8.8 Hz, 1H), 4.56-4.50 (m, 2H), 4.11-4.06 (m, 2H), 3.99-3.92 (m, 2H), 3.22-3.11 (m, 4H), 2.99-2.91 (m, 3H), 2.56 (s, 6H), 2.14-2.07 (m, 2H), 1.75-1.63 (m, 2H). |
| 43 | (4-dimethylamino-piperidinyl 2-CF₃ phenyl) | (N-methylpiperazine) | (M + 1) 537.33 | CDCl₃: δ 9.57-9.52 (m, 1H), 7.98 (d, J = 2.1 Hz, 1H), 7.84-7.76 (m, 2H), 7.74-7.66 (m, 2H), 7.52-7.45 (m, 2H), 7.15 (d, J = 7.7 Hz, 1H), 3.36-3.29 (m, 2H), 3.27-3.10 (m, 5H), 3.08-3.01 (m, 2H), 2.91 (t, J = 11.1 Hz, 2H), 2.74 (s, 6H), 2.53-2.41 (m, 5H), 2.29-2.22 (m, 2H), 1.97-1.89 (m, 2H). |
| 44 | (3-dimethylaminopropoxy 2-CF₃ phenyl) | (N-methylpiperazine) | (M + 1) 512.21 | CDCl₃: δ 9.46-9.39 (m, 1H), 7.88 (d, J = 9.5 Hz, 1H), 7.85 (d, J = 2.1 Hz, 1H), 7.81-7.74 (m, 2H), 7.72 (dd, J = 9.5, 1.9 Hz, 1H), 7.53-7.48 (m, 1H), 7.19 (d, J = 8.0 Hz, 2H), 4.31 (t, J = 5.5 Hz, 2H), 3.46-3.33 (m, 4H), 3.32-3.22 (m, 4H), 2.83 (s, 6H), 2.82-2.72 (m, 2H), 2.63 (s, 3H), 2.44-2.35 (m, 2H). |
| 45 | (4-dimethylamino-piperidinyl phenyl) | ((2R,5S)-2,5-dimethyl-N-methylpiperazine) | (M + 1) 497.29 | CDCl₃: δ 9.41-9.36 (m, 1H), 7.79 (d, J = 9.5 Hz, 1H), 7.73-7.68 (m, 2H), 7.51 (d, J = 8.7 Hz, 2H), 7.49-7.44 (m, 1H), 7.12 (d, J = 7.4 Hz, 1H), 7.06 (d, J = 8.8 Hz, 2H), 3.95-3.90 (m, 2H), 3.22-3.13 (m, 3H), 3.06 (t, J = 11.3 Hz, 2H), 2.93-2.84 (m, 4H), 2.72 (s, 6H), 2.54 (s, 3H), 2.26-2.19 (m, 2H), 1.96-1.86 (m, 2H), 1.31 (d, J = 6.3 Hz, 6H). |
| 46 | (4-dimethylamino-piperidinyl 2-F phenyl) | ((2R,5S)-2,5-dimethyl-N-methylpiperazine) | (M + 1) 515.33 | CDCl₃: δ 9.48-9.43 (m, 1H), 7.75 (d, J = 9.5 Hz, 1H), 7.69 (d, 8.2 Hz, 1H), 7.65 (dd, J = 9.5, 1.8 Hz, 1H), 7.49-7.44 (m, 1H), 7.38-7.34 (m, 1H), 7.34-7.31 (m, 1H), 7.12-7.04 (m, 2H), 3.70-3.64 (m, 2H), 3.19-3.14 (m, 2H), 2.95-2.79 (m, 6H), 2.68-2.65 (m, 1H), 2.61 (s, 6H), 2.43 (s, 3H), 2.22-2.15 (m, 2H), 1.98-1.88 (m, 2H), 1.23 (d, J = 6.2 Hz, 6H). |
| 47 | (4-dimethylamino-piperidinyl 2-Cl phenyl) | ((2R,5S)-2,5-dimethyl-N-methylpiperazine) | (M + 1) 531.26 | CDCl₃: δ 9.47-9.42 (m, 1H), 7.79 (d, J = 9.4 Hz, 1H), 7.71 (d, J = 7.9 Hz, 1H), 7.69-7.62 (m, 2H), 7.52-7.44 (m, 2H), 7.16 (d, J = 8.4 Hz, 1H), 7.12 (d, J = 7.3 Hz, 1H), 3.65-3.59 (m, 2H), 3.24-3.14 (m, 3H), 2.99 (t, J = 11.3 Hz, 2H), 2.88-2.75 (m, 4H), 2.72 (s, 6H), 2.50 (s, 3H), 2.25-2.17 (m, 2H), 2.03-1.92 (m, 2H), 1.28 (d, J = 6.4 Hz, 6H). |
| 48 | (4-dimethylamino-piperidinyl 2-CF₃ phenyl) | ((2R,5S)-2,5-dimethyl-N-methylpiperazine) | (M + 1) 565.38 | CDCl₃: δ 9.56-9.51 (m, 1H), 7.93 (d, J = 2.1 Hz, 1H), 7.80-7.74 (m, 2H), 7.72-7.65 (m, 2H), 7.51-7.44 (m, 2H), 7.11 (d, J = 7.4 Hz, 1H), 3.31-3.25 (m, 2H), 3.19-3.14 (m, 2H), 2.87 (t, J = 11.1 Hz, 4H), 2.78-2.71 (m, 1H), 2.67-2.60 (m, 2H), 2.55 (s, 6H), 2.41 (s, 3H), 2.12-2.05 (m, 2H), 1.89-1.79 (m, 2H), 1.21 (d, J = 6.0 Hz, 6H). |

| Example | Ar | R₁ | LC-MS (ESI) | ¹H NMR, 400 MHz |
|---|---|---|---|---|
| 49 | 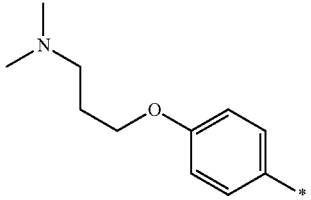 [SMILES: *c1ccc(OCCCN(C)C)cc1] | 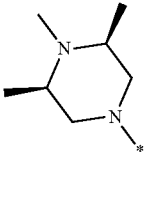 | (M + 1) 472.16 | CDCl₃: δ 9.40-9.37 (m, 1H), 7.82 (d, J = 9.5 Hz, 1H), 7.73-7.68 (m, 2H), 7.53 (d, J = 8.7 Hz, 2H), 7.50-7.45 (m, 1H), 7.13 (d, J = 7.6 Hz, 1H), 7.03 (d, J = 8.7 Hz, 2H), 4.15 (t, J = 5.8 Hz, 2H), 3.21-3.13 (m, 4H), 3.07 (t, J = 10.8 Hz, 2H), 2.92-2.84 (m, 2H), 2.75 (s, 6H), 2.53 (s, 3H), 2.31-2.24 (m, 2H), 1.30 (d, J = 6.3 Hz, 6H). |
| 50 | 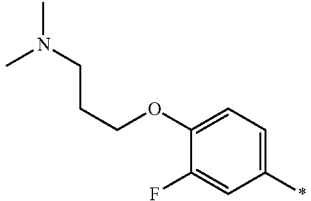 | 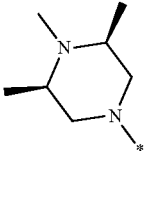 | (M + 1) 490.30 | CDCl₃: δ 9.46-9.40 (m, 1H), 7.76 (d, J = 9.5 Hz, 1H), 7.70 (d, J = 7.8 Hz, 1H), 7.64 (dd, J = 9.5, 1.9 Hz, 1H), 7.49-7.44 (m, 1H), 7.40-7.31 (m, 2H), 7.15-7.07 (m, 2H), 4.22 (t, J = 5.9 Hz, 2H), 3.20-3.14 (m, 2H), 3.04-2.99 (m, 2H), 2.92 (t, J = 11.2 Hz, 2H), 2.71-2.66 (m, 2H), 2.63 (s, 6H), 2.45 (s, 3H), 2.33-2.23 (m, 2H), 1.24 (d, J = 6.0 Hz, 6H). |
| 51 | 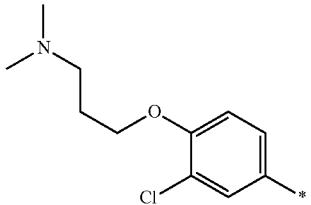 [SMILES: *c1ccc(OCCCN(C)C)c(Cl)c1] | 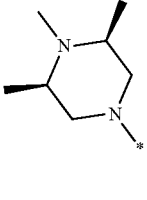 | (M + 1) 506.24 | CDCl₃: δ 9.45-9.38 (m, 1H), 7.78-7.74 (m, 1H), 7.71 (d, J = 7.8 Hz, 1H), 7.67-7.61 (m, 2H), 7.50-7.44 (m, 2H), 7.13-7.07 (m, 2H), 4.25 (t, J = 5.8 Hz, 2H), 3.22-3.16 (m, 2H), 3.15-3.10 (m, 2H), 3.04-2.93 (m, 2H), 2.80-2.67 (m, 8H), 2.50 (s, 3H), 2.41-2.34 (m, 2H), 1.28 (d, J = 6.0 Hz, 6H). |
| 52 | 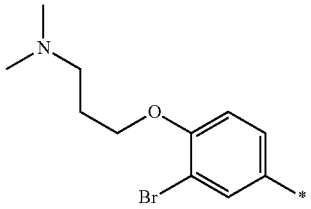 [SMILES: *c1ccc(OCCCN(C)C)c(Br)c1] | 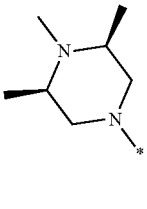 | (M + 1) 550.18 | CDCl₃: δ 9.44-9.39 (m, 1H), 7.85-7.78 (m, 2H), 7.71 (d, J = 8.2 Hz, 1H), 7.68 (dd, J = 9.6, 1.8 Hz, 1H), 7.52 (dd, J = 8.5, 2.2 Hz, 1H), 7.50-7.45 (m, 1H), 7.13 (d, J = 7.6 Hz, 1H), 7.04 (d, J = 8.5 Hz, 1H), 4.22 (t, J = 5.7 Hz, 2H), 3.20-3.16 (m, 4H), 3.05-2.99 (m, 2H), 2.86-2.80 (m, 2H), 2.74 (s, 6H), 2.54 (s, 3H), 2.36-2.29 (m, 2H), 1.31 (d, J = 6.3 Hz, 6H). |
| 53 | 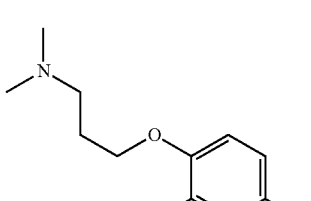 | 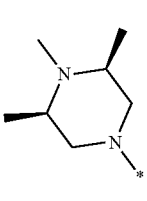 | (M + 1) 540.23 | CDCl₃: δ 9.49-9.44 (m, 1H), 7.84 (d, J = 2.1 Hz, 1H), 7.80 (d, J = 8.8 Hz, 1H), 7.75 (dd, J = 8.6, 2.2 Hz, 1H), 7.72 (d, J = 7.7 Hz, 1H), 7.67 (dd, J = 9.5, 1.9 Hz, 1H), 7.50-7.45 (m, 1H), 7.18 (d, J = 8.6 Hz, 1H), 7.14 (d, J = 7.4 Hz, 1H), 4.30 (t, J = 5.7 Hz, 2H), 3.22-3.16 (m, 2H), 3.15-3.11 (m, 2H), 3.07-2.98 (m, 2H), 2.79-2.71 (m, 8H), 2.50 (s, 3H), 2.40-2.34 (m, 2H), 1.28 (d, J = 6.0 Hz, 6H). |
| 54 | 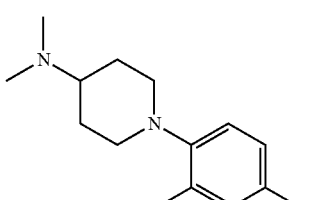 | 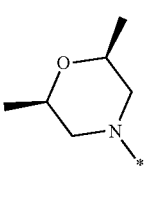 [SMILES: *N1C[C@@H](C)O[C@@H](C)C1] | (M + 1) 552.31 | CDCl₃: δ 9.50-9.45 (m, 1H), 7.86 (d, J = 2.1 Hz, 1H), 7.80 (d, J = 9.5 Hz, 1H), 7.77-7.71 (m, 2H), 7.66 (dd, J = 9.5, 1.8 Hz, 1H), 7.52-7.46 (m, 2H), 7.12 (d, J = 7.7 Hz, 1H), 4.07-3.99 (m, 2H), 3.37-3.31 (m, 2H), 3.29-3.23 (m, 1H), 3.19-3.12 (m, 2H), 2.96-2.89 (m, 2H), 2.82 (s, 6H), 2.75-2.69 (m, 2H), 2.36-2.31 (m, 2H), 2.00-1.93 (m, 2H), 1.30 (d, J = 6.0 Hz, 6H). |

-continued

| Example | Ar | R₁ | LC-MS (ESI) | ¹H NMR, 400 MHz |
|---|---|---|---|---|
| 55 | 3-(dimethylamino)propoxy-2-(trifluoromethyl)phenyl | 2,6-dimethylmorpholin-4-yl | (M + 1) 527.24 | CDCl₃: δ 9.45-9.40 (m, 1H), 7.82-7.76 (m, 2H), 7.75-7.70 (m, 2H), 7.64 (dd, J = 9.5, 1.8 Hz, 1H), 7.51-7.46 (m, 1H), 7.18 (d, J = 8.6 Hz, 1H), 7.11 (d, J = 7.6 Hz, 1H), 4.32 (t, J = 5.5 Hz, 2H), 4.06-3.98 (m, 2H), 3.24-3.19 (m, 2H), 3.18-3.12 (m, 2H), 2.83 (s, 6H), 2.75-2.68 (m, 2H), 2.51-2.45 (m, 2H), 1.29 (d, J = 6.0 Hz, 6H). |
| 56 | 4-[4-(dimethylamino)piperidin-1-yl]phenyl | 4-(dimethylamino)piperidin-1-yl | (M + 1) 497.37 | DMSO-d₆: δ 9.34-9.26 (m, 1H), 7.88 (dd, J = 9.5, 1.7 Hz, 1H), 7.74 (d, J = 9.6 Hz, 1H), 7.64-7.48 (m, 3H), 7.46-7.39 (m, 1H), 7.17-7.01 (m, 3H), 3.84-3.77 (m, 2H), 3.35-3.30 (m, 2H), 2.84 (t, J = 11.6 Hz, 2H), 2.74 (t, J = 11.4 Hz, 2H), 2.48-2.39 (m, 2H), 2.31 (s, 6H), 2.24 (s, 6H), 2.03-1.93 (m, 2H), 1.91-1.83 (m, 2H), 1.81-1.70 (m, 2H), 1.55-1.45 (m, 2H). |
| 57 | 4-[4-(dimethylamino)piperidin-1-yl]-3-fluorophenyl | 4-(dimethylamino)piperidin-1-yl | (M + 1) 515.28 | CDCl₃: δ 9.41-9.35 (m, 1H), 7.78-7.73 (m, 1H), 7.73-7.69 (m, 1H), 7.67 (dd, J = 9.5, 1.9 Hz, 1H), 7.48-7.43 (m, 1H), 7.39-7.34 (m, 1H), 7.31 (dd, J = 13.6, 2.1 Hz, 1H), 7.15-7.10 (m, 1H), 7.08 (d, J = 7.2 Hz, 1H), 3.68-3.62 (m, 2H), 3.48-3.41 (m, 2H), 2.99-2.88 (m, 3H), 2.86-2.79 (m, 3H), 2.63 (s, 6H), 2.60 (s, 6H), 2.27-2.16 (m, 4H), 2.03-1.88 (m, 4H). |
| 58 | 4-[4-(dimethylamino)piperidin-1-yl]-3-chlorophenyl | 4-(dimethylamino)piperidin-1-yl | (M + 1) 531.25 | CDCl₃: δ 9.35-9.32 (m, 1H), 7.79 (d, J = 9.5 Hz, 1H), 7.73 (d, J = 8.2 Hz, 1H), 7.68 (dd, J = 9.5, 1.8 Hz, 1H), 7.63 (d, J = 2.1 Hz, 1H), 7.52 (dd, J = 8.3, 2.2 Hz, 1H), 7.50-7.45 (m, 1H), 7.22 (d, J = 8.3 Hz, 1H), 7.09 (d, J = 7.6 Hz, 1H), 3.61-3.55 (m, 2H), 3.50-3.44 (m, 2H), 3.20-3.11 (m, 2H), 2.99 (t, J = 11.5 Hz, 2H), 2.81 (t, J = 11.3 Hz, 2H), 2.73 (s, 12H), 2.23-2.27 (m, 2H), 2.23-2.17 (m, 2H), 2.08-1.94 (m, 4H). |
| 59 | 4-[4-(dimethylamino)piperidin-1-yl]-3-bromophenyl | 4-(dimethylamino)piperidin-1-yl | (M + 1) 575.23 | CDCl₃: δ 9.33-9.28 (m, 1H), 7.83 (d, J = 2.0 Hz, 1H), 7.79 (d, J = 9.5 Hz, 1H), 7.72 (d, J = 8.2 Hz, 1H), 7.66 (dd, J = 9.5, 1.7 Hz, 1H), 7.56 (dd, J = 8.3, 2.0 Hz, 1H), 7.50-7.44 (m, 1H), 7.20 (d, J = 8.3 Hz, 1H), 7.09 (d, J = 7.7 Hz, 1H), 3.58-3.52 (m, 2H), 3.50-3.43 (m, 2H), 3.17-3.07 (m, 2H), 2.98 (t, J = 11.6 Hz, 2H), 2.80 (t, J = 11.3 Hz, 2H), 2.68 (s, 12H), 2.31-2.23 (m, 2H), 2.19-2.13 (m, 2H), 2.07-1.92 (m, 4H). |
| 60 | 4-[4-(dimethylamino)piperidin-1-yl]-3-(trifluoromethyl)phenyl | 4-(dimethylamino)piperidin-1-yl | (M + 1) 565.33 | CDCl₃: δ 9.30-9.26 (m, 1H), 7.80 (d, J = 2.1 Hz, 1H), 7.74-7.69 (m, 2H), 7.64 (d, J = 7.8 Hz, 1H), 7.58 (dd, J = 9.5, 1.9 Hz, 1H), 7.45-7.38 (m, 2H), 7.03 (d, J = 7.4 Hz, 1H), 3.39-3.34 (m, 2H), 3.22-3.16 (m, 2H), 2.87 (t, J = 11.5 Hz, 2H), 2.79 (t, J = 11.0 Hz, 2H), 2.73-2.67 (m, 1H), 2.63-2.57 (m, 1H), 2.49 (s, 6H), 2.41 (s, 6H), 2.13-2.07 (m, 2H), 2.06-2.01 (m, 2H), 1.85-1.73 (m, 4H). |

| Example | Ar | R₁ | LC-MS (ESI) | ¹H NMR, 400 MHz |
|---|---|---|---|---|
| 61 | 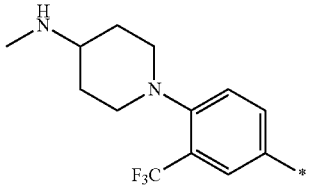 [SMILES: *c1ccc(N2CCC(NC)CC2)c(C(F)(F)F)c1] | 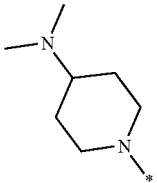 | (M + 1) 551.33 | CDCl₃: δ 9.36-9.31 (m, 1H), 7.86 (d, J = 2.0 Hz, 1H), 7.83-7.76 (m, 2H), 7.72 (d, J = 8.0 Hz, 1H), 7.66 (dd, J = 9.5, 1.8 Hz, 1H), 7.57 (d, J = 8.4 Hz, 1H), 7.49-7.44 (m, 1H), 7.09 (d, J = 7.6 Hz, 1H), 3.48-3.41 (m, 2H), 3.33-3.23 (m, 2H), 3.08-2.83 (m, 6H), 2.69 (s, 3H), 2.55 (s, 6H), 2.29-2.15 (m, 4H), 2.02-1.88 (m, 4H). |
| 62 | 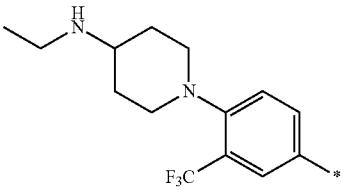 [SMILES: *c1ccc(N2CCC(NCC)CC2)c(C(F)(F)F)c1] | 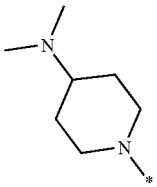 | (M + 1) 565.29 | CDCl₃: δ 9.36-9.31 (m, 1H), 7.86 (d, J = 2.0 Hz, 1H), 7.81-7.75 (m, 2H), 7.70 (d, J = 8.1 Hz, 1H), 7.65 (dd, J = 9.5, 1.8 Hz, 1H), 7.52 (d, J = 8.3 Hz, 1H), 7.49-7.44 (m, 1H), 7.09 (d, J = 7.6 Hz, 1H), 3.46-3.38 (m, 2H), 3.29-3.20 (m, 2H), 3.08-2.96 (m, 3H), 2.95-2.78 (m, 4H), 2.75-2.67 (m, 1H), 2.48 (s, 6H), 2.24-2.10 (m, 4H), 2.01-1.84 (m, 4H), 1.42 (t, J = 7.2 Hz, 3H). |
| 63 | 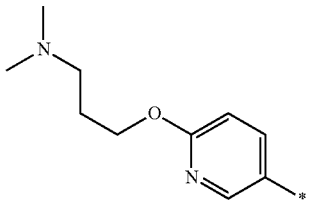 [SMILES: *c1ccc(OCCCN(C)C)nc1] | 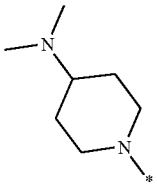 | (M + 1) 473.26 | CDCl₃: δ 9.38-9.34 (m, 1H), 8.42 (d, J = 2.4 Hz, 1H), 7.83 (dd, J = 8.6, 2.6 Hz, 1H), 7.77 (d, J = 9.5 Hz, 1H), 7.70 (d, J = 8.2 Hz, 1H), 7.62 (dd, J = 9.5, 1.9 Hz, 1H), 7.48-7.43 (m, 1H), 7.08 (d, J = 7.6 Hz, 1H), 6.87 (d, J = 8.6 Hz, 1H), 4.41 (t, J = 6.4 Hz, 2H), 3.44-3.38 (m, 2H), 2.95-2.87 (m, 2H), 2.60-2.57 (m, 2H), 2.53-2.51 (m, 1H), 2.42 (s, 6H), 2.36 (s, 6H), 2.12-2.02 (m, 4H), 1.89-1.80 (m, 2H). |
| 64 | 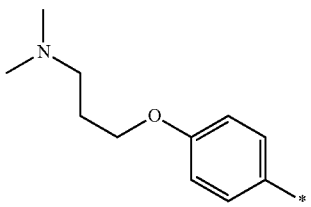 [SMILES: *c1ccc(OCCCN(C)C)cc1] | 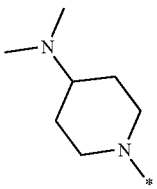 | (M + 1) 472.26 | CDCl₃: δ 9.34-9.29 (m, 1H), 7.77-7.74 (m, 1H), 7.73-7.67 (m, 2H), 7.60-7.53 (m, 2H), 7.47-7.43 (m, 1H), 7.11-7.02 (m, 3H), 4.18 (t, J = 5.9 Hz, 2H), 3.51-3.45 (m, 2H), 3.09-3.04 (m, 2H), 3.00-2.92 (m, 3H), 2.78-2.65 (m, 12H), 2.35-2.27 (m, 4H), 2.13-2.03 (m, 2H). |
| 65 | 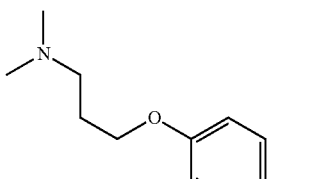 | 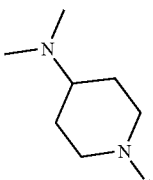 | (M + 1) 490.23 | CDCl₃: δ 9.38-9.34 (m, 1H), 7.78 (d, J = 9.5 Hz, 1H), 7.72 (d, J = 8.1 Hz, 1H), 7.67 (dd, J = 9.5, 1.9 Hz, 1H), 7.49-7.45 (m, 1H), 7.38-7.35 (m, 1H), 7.35-7.33 (m, 1H), 7.13 (d, J = 8.5 Hz, 1H), 7.09 (d, J = 7.8 Hz, 1H), 4.19 (t, J = 5.9 Hz, 2H), 3.47-3.42 (m, 2H) 3.06-2.94 (m, 5H), 2.65 (s, 6H), 2.62 (s, 6H), 2.27-2.20 (m, 4H), 2.04-1.97 (m, 2H). |
| 66 | 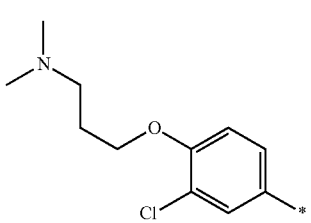 [SMILES: *c1ccc(OCCCN(C)C)c(Cl)c1] | 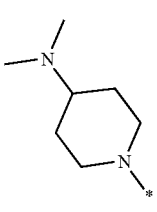 | (M + 1) 506.19 | CDCl₃: δ 9.35-9.27 (m, 1H), 7.76 (d, J = 9.5 Hz, 1H), 7.71 (d, J = 8.1 Hz, 1H), 7.68-7.61 (m, 2H), 7.52-7.44 (m, 2H), 7.14-7.05 (m, 2H), 4.19 (t, J = 6.0 Hz, 2H), 3.50-3.40 (m, 2H), 3.01-2.85 (m, 5H), 2.60 (s, 6H), 2.54 (s, 6H), 2.27-2.16 (m, 4H), 2.03-1.92 (m, 2H). |

| Example | Ar | R₁ | LC-MS (ESI) | ¹H NMR, 400 MHz |
|---|---|---|---|---|
| 67 | (dimethylaminopropoxy-bromophenyl) | (N-methylpiperidin-4-yl)(methyl)amino | (M + 1) 550.18 | CDCl₃: δ 9.32-9.25 (m, 1H), 7.81 (d, J = 2.2 Hz, 1H), 7.76 (d, J = 9.5 Hz, 1H), 7.71 (d, J = 8.1 Hz, 1H), 7.64 (dd, J = 9.5, 1.8 Hz, 1H), 7.54 (dd, J = 8.5, 2.2 Hz, 1H), 7.49-7.43 (m, 1H), 7.13-7.03 (m, 2H), 4.20 (t, J = 6.0 Hz, 2H), 3.49-3.41 (m, 2H), 2.99-2.90 (m, 3H), 2.85-2.81 (m, 2H), 2.58 (s, 6H), 2.50 (s, 6H), 2.29-2.15 (m, 4H), 2.03-1.92 (m, 2H). |
| 68 | (dimethylaminopropoxy-trifluoromethylphenyl) | (N-methylpiperidin-4-yl)(methyl)amino | (M + 1) 540.23 | CDCl₃: δ 9.32-9.28 (m, 1H), 7.82-7.76 (m, 3H), 7.73 (d, J = 8.2 Hz, 1H), 7.66 (dd, J = 9.5, 1.8 Hz, 1H), 7.50-7.45 (m, 1H), 7.31-7.27 (m, 1H), 7.09 (d, J = 7.6 Hz, 1H), 4.28 (t, J = 5.8 Hz, 2H), 3.50-3.44 (m, 2H), 2.99-2.89 (m, 5H), 2.63 (s, 6H), 2.59 (s, 6H), 2.32-2.23 (m, 4H), 2.03-1.93 (m, 2H). |
| 69 | (4-(N-methylpiperidin-4-yl)amino-trifluoromethylphenyl) | (1-methylpiperidin-4-yl)oxy | (M + 1) 552.27 | CDCl₃: δ 9.31-9.26 (m, 1H), 7.86 (d, J = 2.1 Hz, 1H), 7.84-7.80 (m, 1H), 7.78 (dd, J = 8.3, 2.0 Hz, 1H), 7.70 (dd, J = 9.5, 1.9 Hz, 1H), 7.59-7.54 (m, 1H), 7.50-7.46 (m, 1H), 7.46-7.41 (m, 1H), 6.81 (d, J = 7.9 Hz, 1H), 4.89-4.85 (m, 1H), 3.31-3.21 (m, 3H), 3.08-2.94 (m, 4H), 2.94-2.87 (m, 2H), 2.73 (s, 6H), 2.55 (s, 3H), 2.47-2.38 (m, 2H), 2.30-2.22 (m, 2H), 2.18-2.11 (m, 2H), 1.96-1.86 (m, 2H). |
| 70 | (dimethylaminopropoxy-trifluoromethylphenyl) | (1-methylpiperidin-4-yl)oxy | (M + 1) 527.19 | CDCl₃: δ 9.33-9.27 (m, 1H), 7.82 (d, J = 2.1 Hz, 1H), 7.78 (d, J = 9.5 Hz, 1H), 7.74 (dd, J = 8.6, 2.2 Hz, 1H), 7.67 (dd, J = 9.5, 1.9 Hz, 1H), 7.54 (d, J = 8.2 Hz, 1H), 7.46-7.39 (m, 1H), 7.14 (d, J = 8.6 Hz, 1H), 6.81 (d, J = 7.9 Hz, 1H), 4.88-4.79 (m, 1H), 4.23 (t, J = 5.7 Hz, 2H), 3.05-2.96 (m, 2H), 2.94-2.83 (m, 2H), 2.83-2.69 (m, 2H), 2.62 (s, 6H), 2.45 (s, 3H), 2.37-2.14 (m, 6H). |

Example 71

N,N-dimethyl-1-(4-(4-((3S,5R)-3,4,5-trimethylpiperazin-1-yl)pyridazino[6,1-f]purin-7-yl)phenyl)piperidin-4-amine

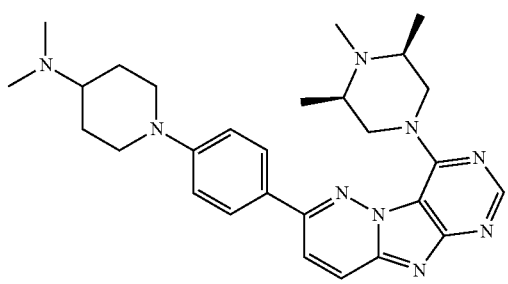 [SMILES: C[C@@H]1CN(c2ncnc3nc4ccc(-c5ccc(N6CCC(N(C)C)CC6)cc5)nn4c23)C[C@H](C)N1C]

a) 6-((3S,5R)-3,4,5-Trimethylpiperazin-1-yl)pyrimidin-4-amine: 6-chloropyrimidin-4-amine (500 mg, 3.9 mmol) was dissolved in anhydrous N,N-dimethylformamide (10 mL). (2R,6S)-1,2,6-Trimethylpiperazine hydrochloride (1.2 g, 5.8 mmol) and potassium carbonate (1.6 g, 10.6 mmol) were added sequentially. After reaction under agitation at 120° C. for 2 days, the reaction solution was cooled to room temperature, filtered, and concentrated by removing the organic solvent at reduced pressure to obtain a crude product. Isolation and purification by column chromatography (silica gel, methylene dichloride:methanol=5:1 as an eluant) were performed to obtain the target compound (431 mg, 50.5% yield). LC-MS (ESI): m/z (M+1) 222.17.

b) 5-Iodo-6-((3S,5R)-3,4,5-trimethylpiperazin-1-yl)pyrimidin-4-amine: 6-((3S,5R)-3,4,5-trimethylpiperazin-1-yl)pyrimidin-4-amine (380 mg, 1.7 mmol) was dissolved in trifluoromethanesulfonic acid (10 mL), and N-iodosuccinimide (579 mg, 2.6 mmol) was added. After reaction under agitation overnight at room temperature, the reaction mixture was cooled to 0° C., and the pH value of the reaction solution was adjusted to 7-8 using a saturated sodium bicarbonate aqueous solution (50 mL). Ethyl acetate (20 mL) and water (10 mL) were added to perform extraction and liquid separation. The aqueous phase was extracted with ethyl acetate (15 mL×2). The organic phases were combined, washed with a saturated saline solution, dried with anhydrous sodium sulfate, filtered and concentrated by removing the organic solvent at reduced pressure to obtain a crude product. Isolation and purification by column chromatography (silica gel, methylene dichloride:methanol=5:1 as an eluant) were performed to obtain the target compound (400 mg, 67% yield). LC-MS (ESI): m/z (M+1) 348.06.

c) 6-Bromo-4-((3S,5R)-3,4,5-trimethylpiperazin-1-yl)pyridazo[6,1-f]purine: 5-iodo-6-((3S,5R)-3,4,5-trimethylpiperazin-1-yl)pyrimidin-4-amine (400 mg, 1.15 mmol) was dissolved in anhydrous xylene (20 mL). 3,6-dibromopyridazine (329 mg, 1.38 mmol), cesium carbonate (1.1 g, 3.46 mmol), cuprous iodide (44 mg, 0.23 mmol) and 1,10-phenanthroline (83 mg, 0.46 mmol) were added sequentially. After reaction under agitation at 150° C. for 3 hours, the reaction mixture was cooled to room temperature, and concentrated by removing the organic solvent at reduced pressure to obtain a crude product. Isolation and purification by column chromatography (silica gel, methylene dichloride:methanol=10:1 as an eluant) were performed to obtain the target compound (279 mg, 64.4% yield). LC-MS (ESI): m/z (M+1) 376.18.

d) N,N-Dimethyl-1-(4-(443S,5R)-3,4,5-trimethylpiperazin-1-yl)pyridazino[6,1-f]purin-7-yl)phenyl)piperidin-4-amine: at room temperature, 7-bromo-4-(3S,5R)-3,4,5-trimethylpiperazin-1-yl)pyridazo[6,1-f]purine (80 mg, 0.21 mmol) was dissolved in a mixed solvent of dioxane (1.0 mL) and water (0.25 mL), and N,N-dimethyl-1-(4-(4,4,5,5-tetramethyl-1,3,2-dioxaborolan-2-yl) phenyl)piperidin-4-amine (140 mg, 0.42 mmol), cesium carbonate (208 mg, 0.64 mmol), tetrakis(triphenylphosphine) palladium (24 mg, 0.02 mmol) were added sequentially. After reaction under agitation overnight at 100° C., the reaction mixture was cooled to room temperature, and concentrated by removing the organic solvent at reduced pressure to obtain a crude product. Isolation and purification by preparative liquid chromatography (C18 column, 10-100% acetonitrile/water as a mobile phase) were performed to obtain the target compound (10 mg, 9.4% yield, yellow solid). LC-MS (ESI): m/z (M+1) 500.34. $^1$H NMR (400 MHz, CDCl$_3$): δ 8.77 (s, 1H), 8.21 (d, J=9.7 Hz, 1H), 7.89 (d, J=8.9 Hz, 2H), 7.85 (d, J=9.7 Hz, 1H), 7.07 (d, J=8.9 Hz, 2H), 4.78-4.72 (m, 2H), 4.06-4.01 (m, 2H), 3.64-3.57 (m, 2H), 3.26-3.20 (m, 2H), 2.98-2.91 (m, 3H), 2.74 (s, 6H), 2.66 (s, 3H), 2.26-2.22 (m, 2H), 1.93-1.86 (m, 2H), 1.40 (d, J=6.3 Hz, 6H).

Example 72

In Vitro Inhibition of ATM by N,N-dimethyl-3-((5-(9-(3,6-dihydro-2H-pyran-4-yl)benzo[4,5]imidazo[1,2-a]pyridin-2-yl)pyridin-2-yl)oxy)propan-1-amine and its Analogues was Determined by ATM Kinase Assay ATM enzyme (human) was added to the reaction solution containing 30 nM GST-cMyc-p53 and 10 μM Mg/ATP, and then 50 times the concentration of the tested compound (or reference compound AZD0156) dissolved in 100% DMSO was added to the final concentration of 10 μM/1 μM/0.1 μM/0.01 μM. The reaction was initiated by the addition of a Mg/ATP mixture and incubation for 30 minutes at room temperature, the reaction was quenched by the addition of a stop solution containing EDTA. Finally, the detection buffer containing the d2-labeled anti-GST monoclonal antibody and the europium-labeled anti-phospho p53 (Ser15) antibody was added. The plate was then read in time resolved fluorescence mode and the homogeneous time resolved fluorescence (HTRF) signal was determined according to the equation: HTRF=10000×(Em$_{665nm}$/Em$_{620nm}$). Each compound sample was repeated in duplicate. The negative control contained all components except the ATM enzyme, and the positive control contained all components. All reactions were quenched by adding EDTA.

Table 1 summarizes the ATM kinase inhibition data of compounds (% inhibition rate).

TABLE 1

Inhibition of ATM kinase by N,N-dimethyl-3-((5-(9-(3,6-dihydro-2H-pyran-4-yl)benzo[4,5]imidazo[1,2-a]pyridin-2-yl)pyridin-2-yl)oxy) propan-1-amine and its analogues

| Example | 1 | 2 | 4 | 5 | 6 | 7 | 8 | 9 |
|---|---|---|---|---|---|---|---|---|
| Detected concentration (μm) | 10 | 1 | 1 | 1 | 1 | 1 | 1 | 1 |
| inhibition(%) | 100 | 81 | 74 | 61 | 77 | 64 | 99 | 60 |
| Example | 10 | 11 | 12 | 13 | 14 | 15 | 16 | 17 |
| Detected concentration (μm) | 1 | 1 | 1 | 1 | 1 | 1 | 1 | 1 |
| inhibition(%) | 77 | 63 | 88 | 86 | 48 | 39 | 53 | 37 |
| Example | 39 | 40 | 41 | 42 | 43 | 44 | | |
| Detected concentration (μm) | 1 | 0.1 | 0.01 | 1 | 1 | 1 | 1 | 1 |
| inhibition(%) | 91 | 62 | 17 | 96 | 82 | 88 | 99 | 97 |
| Example | 45 | 46 | 47 | 48 | 53 | 56 | AZD0156 | |
| Detected concentratio (μm) | 1 | 1 | 1 | 1 | 1 | 1 | 1 | |
| inhibition(%) | 100 | 100 | 100 | 100 | 100 | 81 | 100 | |

The compounds were serially diluted to 10 concentrations with 100% DMSO at the ratio of 1:3 and 1:10 (the last concentration was negative control of DMSO), then added to the ATM buffer and diluted to a final concentration of 10, 3, 1, 0.3, 0.1, 0.03, 0.01, 0.003, 0.001 and 0 μM, respectively. ATM kinase inhibition was detected by using the method described above. The curve equation for calculating IC$_{50}$ value is as follows:

$$Y(\text{Inh } \%) = \frac{100}{1 + 10^{(\log IC_{50} - \log C) \times D}}$$

wherein, C is the concentration of compound and D is the slope factor. Table 2 summarizes the IC$_{50}$ values of compounds inhibiting ATM kinase.

TABLE 2

In vitro inhibitory effects of N,N-dimethyl-3-((5-(9-(3,6-dihydro-2H-pyran-4-yl)benzo[4,5]imidazo[1,2-a]pyridin-2-yl)pyridin-2-yl)oxy)propan-1-amine and its analogues on ATM kinase (IC$_{50}$ value)

| Example | 1 |
|---|---|
| IC$_{50}$ (nM) | 239 |

Therefore, N,N-dimethyl-3-((5-(9-(3,6-dihydro-2H-pyran-4-yl)benzo[4,5]imidazo[1,2-a]pyridin-2-yl)pyridin-2-yl)oxy)propan-1-amine (Example 1) and its analogues show a good effect on ATM kinase by ATM kinase (human) assay.

Example 73

Inhibitory effects of N,N-dimethyl-3-((5-(9-(3,6-dihydro-2H-pyran-4-yl)benzo[4,5]imidazo[1,2-a]pyridin-2-yl)pyridin-2-yl)oxy)propan-1-amine and its analogues combined with CPT-11 on the growth of human colon cancer cell SW620 were determined by MTT assay The revived SW620 cells were cultured and passaged until they grew well and had a confluence about 90%. SW620 cells were digested by trypsinase, centrifuged at 800 rpm for 5 minutes, the supernatant was discarded, resuspended with fresh medium (RPMI 1640 medium+10% FBS) and counted. The cells were seeded into 96-well cell culture plate with appropriate cell density and incubated overnight in a 37° C. 5% $CO_2$ incubator. The stock solutions of the tested compound and the reference compound AZD0156 were serially diluted to 8 concentrations by DMSO at the ratios of 1:3 and 1:10, respectively, and the last concentration was negative control of DMSO (0 μM, the final concentration of DMSO was 1%). 5 μL of each concentration was added to 120 μL of medium (25 times diluted) and mixed by shaking. The overnight cells were taken and the culture medium was removed, 195 μL of fresh medium containing 205 nM CPT-11 was added to each well, and 5 μL of diluted medium containing the corresponding concentration of the tested sample was added respectively, and the culture plate was then placed in the 5% $CO_2$ cell culture incubator at 37° C. for 5 days. After removing the original solution, 100 μL of fresh serum-free DMEM medium containing MTT (0.5 mg/mL) was added to each well, the culture was continued. After 4 hours, the original solution was removed, 100 μL of DMSO was added into each well, the 96-well plates were shaken away from light for 10 minutes and placed in a multi-function reader to read the absorbance at the wavelength of 552/630/690 nm. GraphPad Prism 6.0 was used to analyze the data. The inhibitory activity of compounds on cell proliferation was plotted based on cell viability and compound concentration. The $IC_{50}$ value was fitted by a sigmoidal dose response curve equation $Y=100/(1+10^{\wedge}(Log\ C-Log\ IC_{50}))$, where C was the concentration of compound.

Table 3 summarizes the inhibitory effects of compounds combined with CPT-11 on the growth of human colon cancer cell SW620 ($IC_{50}$).

TABLE 3

Inhibitory effects of N,N-dimethyl-3-((5-(9-(3,6-dihydro-2H-pyran-4-yl)benzo[4,5]imidazo[1,2a]pyridin-2-yl)pyridin-2-yl)oxy)propan-1-amine and its analogues combined with CPT-11 on the growth of human colon cancer cell SW620

| Example | 1 | 2 | 3 | 4 | 5 | 6 |
|---|---|---|---|---|---|---|
| $IC_{50}$ (nm) | 1340 | 1665 | 563.2 | 5481 | >$10^4$ | 2472 |
| Example | 7 | 8 | 9 | 10 | 11 | 12 |
| $IC_{50}$ (nm) | >$10^4$ | 433.8 | 9309 | >$10^4$ | 1041 | 528.1 |
| Example | 13 | 14 | 15 | 16 | 17 | 39 |
| $IC_{50}$ (nm) | 1570 | >$10^4$ | 2423 | >$10^4$ | 3251 | 1514 |
| Example | 40 | 41 | 42 | 43 | 44 | 45 |
| $IC_{50}$ (nm) | 2367 | 3478 | 2097 | 1049 | >500 | >500 nM |
| Example | 46 | 47 | 48 | 50 | 53 | 54 |
| $IC_{50}$ (nm) | 152.1 | 166 | >$10^3$ | >$10^3$ | 161.5 | 193.1 |
| Example | 55 | 56 | 71 | AZD0156 | | |
| $IC_{50}$ (nm) | 228.3 | 40.87 | 1245 | 8.502 | | |

Therefore, by MTT assay, N,N-dimethyl-1-(4-(9-(4-(dimethylamino)piperidin-1-yl)benzo[4,5]imidazo[1,2-a]pyridin-2-yl)phenyl)piperidin-4-amine (Example 56) and its analogues inhibited the growth of SW620 cell.

Example 74

Inhibitory effects of N,N-dimethyl-3-((5-(9-(3,6-dihydro-2H-pyran-4-yl)benzo[4,5]imidazo[1,2-a]pyridin-2-yl)pyridin-2-yl)oxy)propan-1-amine and its analogues on the growth of human breast cancer cell MDA-MB-468 were determined by MTT assay The revived MDA-MB-468 cells were cultured and passaged until they grew well and had a confluence about 90%. MDA-MB-468 cells were digested by trypsinase, centrifuged at 800 rpm for 5 minutes, the supernatant was discarded, resuspended with fresh medium (RPMI 1640 medium+10% FBS) and counted. The cells were seeded into 96-well cell culture plate with appropriate cell density and incubated overnight in a 37° C. 5% $CO_2$ incubator. The stock solutions of the tested compound and the reference compound AZD0156 were serially diluted to 8 concentrations by DMSO at the ratios of 1:3 and 1:10, respectively: the last concentration was negative control of DMSO (0 μM, the final concentration of DMSO was 1%). 5 μL of each concentration was added to 120 μL of medium (25 times diluted) and mixed by shaking. The overnight cells were taken and the culture medium was removed, 195 μL of fresh medium (PRMI 1640+5% FBS) was added to each well, and 5 μL of diluted medium containing the corresponding concentration of the tested sample was added respectively, and the culture plate was then placed in the 5% $CO_2$ cell culture incubator at 37° C. for 7 days (On the fourth day, the medium containing drugs was removed and fresh medium containing drugs was added for continuous cultivation). After removing the original solution, 100 μL of fresh serum-free DMEM medium containing MTT (0.5 mg/mL) was added to each well, the culture was continued. After 4 hours, the original solution was removed, 100 μL of DMSO was added into each well, the 96-well plates were shaken away from light for 10 minutes and placed in a multi-function reader to read the absorbance at the wavelength of 552/630/690 nm. GraphPad Prism 6.0 was used to analyze the data. The inhibitory activity of compounds on cell proliferation was plotted based on cell viability and compound concentration. The $IC_{50}$ value was fitted by a sigmoidal dose response curve equation $Y=100/(1+10^{\wedge}(Log\ C-Log\ IC_{50}))$, where C was the concentration of compound.

Table 4 summarizes the inhibitory effects of compounds on the growth of human breast cancer cell MDA-MB-468 ($IC_{50}$).

TABLE 4

Inhibitory effects of N,N-dimethyl-3-((5-(9-(3,6-dihydro-2H-pyran-4-yl)benzo[4,5]imidazo[1,2-a]pyridin-2-yl)pyridin-2-yl) oxy) propan-1-amineand its analogues on the growth of human colon cancer cell MDA-MB-468

| Example | 1 | 3 | 8 | 9 | 10 | 12 |
|---|---|---|---|---|---|---|
| $IC_{50}$ (nm) | 2799 | 329.6 | 25.09 | 3656 | >$10^4$ | 702.6 |
| Example | 15 | 16 | 17 | 42 | 43 | 44 |
| $IC_{50}$ (nm) | >$10^4$ | >$10^4$ | 2616 | 2399 | 542.4 | >$10^5$ |
| Example | 45 | 46 | 47 | 48 | 50 | 54 |
| $IC_{50}$ (nm) | 321.9 | 55.03 | 60.45 | >$10^3$ | >$10^3$ | 220.1 |
| Example | 55 | 56 | 71 | AZD0156 | | |
| $IC_{50}$ (nm) | 255 | 41.43 | 1798 | 10.57 | | |

Therefore, by MTT assay, N,N-dimethyl-1-(4-(9-(4-(dimethylamino)piperidin-1-yl)benzo[4,5]imidazo[1,2-a]pyridin-2-yl)phenyl)piperidin-4-amine (Example 56) and its analogues inhibited the growth of MDA-MB-468 cell.

Having now fully described this disclosure, it will be understood by those of ordinary skill in the art that the same can be performed within a wide and equivalent range of conditions, formulations and other parameters without affecting the scope of the disclosure or any embodiment thereof. All patents, patent applications and publications cited herein are fully incorporated by reference herein in their entirety.

What is claimed is:

1. A compound having the Formula I:

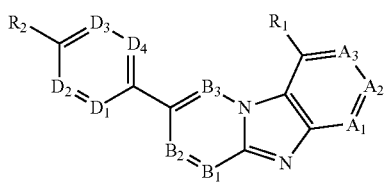

Formula I or a pharmaceutically acceptable salt thereof, wherein:
$A_1$-$A_3$ each are independently N or CR'; $B_1$-$B_3$ each are independently N or CR"; and $D_1$-$D_4$ each are independently N or CR''';
$R_1$ is optionally substituted alkyl, optionally substituted alkoxy, optionally substituted amino, optionally substituted carbocyclic group, optionally substituted heterocyclic group, optionally substituted aryl, optionally substituted heterocyclic oxy group, or optionally substituted heteroaryl;
$R_2$ is optionally substituted alkoxy, optionally substituted amino, optionally substituted carbocyclic group, optionally substituted heterocyclic group, optionally substituted aryl or optionally substituted heteroaryl;
R', R" and R''' each are independently hydrogen, halo, optionally substituted amino, optionally substituted alkoxy, optionally substituted $C_{1-10}$ alkyl, alkenyl, alkynyl, nitro, cyano, acylamido, hydroxy, thiol, acyloxy, azido, carboxy, ethylenedioxo, hydroxyacylamido or optionally substituted alkylthiol.

2. The compound of claim 1, wherein the compound has Formula IIa or IIb:

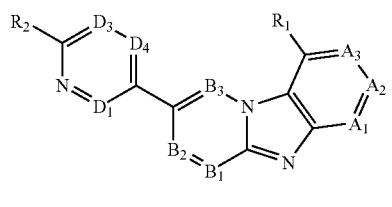

Formula IIa

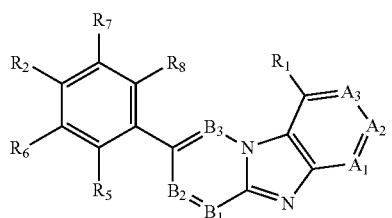

Formula IIb or pharmaceutically acceptable salts thereof, wherein:
$A_1$-$A_3$, $B_1$-$B_3$, $D_1$, $D_3$-$D_4$ and $R_1$-$R_2$ are defined as in claim 1;

$R_5$-$R_8$ are independently H, halo, optionally substituted amino, optionally substituted alkoxy, optionally substituted $C_{1-10}$ alkyl, alkenyl, alkynyl, nitro, cyano, acylamido, hydroxy, thiol, acyloxy, azido, carboxy, ethylenedioxo, hydroxyacylamido or optionally substituted alkylthiol.

3. The compound of claim 2, wherein,
the ring including $A_1$-$A_3$ is phenyl or pyridyl; the ring including $B_1$-$B_3$ is pyridyl, pyrimidinyl, pyrazinyl or pyridazinyl;
the ring including $D_1$-$D_4$ is pyridyl or phenyl;
$R_1$ is selected from the group consisting of dihydropyranyl; tetrahydropyranyl; piperidyl that is not substituted or optionally substituted with 1-4 $C_{1-6}$ alkyl or —$NR_3R_4$ groups; morpholinyl; imidazolyl; piperazinyl that is optionally substituted with 1-4 $C_{1-6}$ alkyl groups; and a $C_{1-6}$ alkyl or amino or oxy group that is optionally substituted with a heterocyclic group;
$R_2$ is selected from the group consisting of $C_{1-6}$ alkoxyl optionally substituted with —$NR_3R_4$, piperazinyl optionally substituted with 1-3 $C_{1-4}$ alkyl groups, and piperidyl optionally substituted with —$NR_3R_4$; wherein, $R_3$ and $R_4$ are independently selected from H and $C_{1-6}$ alkyl; and
R', R" and R''' are H.

4. The compound of claim 1, wherein,
the ring including $A_1$-$A_3$, imidazolyl ring and the ring including $B_1$-$B_3$ are fused to benzo[4,5]imidazo[1,2-a]pyridinyl; the ring including $D_1$-$D_4$ is pyridyl or phenyl; R', R" and R''' are H; $R_1$ is selected from the group consisting of dihydropyranyl; tetrahydropyranyl; piperidyl that is not substituted or optionally substituted with 1-4 $C_{1-6}$ alkyl or —$NR_3R_4$ groups; morpholinyl; imidazolyl; piperazinyl that is optionally substituted with 1-4 $C_{1-6}$ alkyl groups; and a $C_{1-6}$ alkyl amino or oxy group that is optionally substituted with morpholinyl, piperazinyl optionally substituted by 1-3 $C_{1-6}$ alkyl, piperidyl optionally substituted with 1-3 $C_{1-6}$ alkyl or tetrahydropyranyl; $R_2$ is selected from the group consisting of $C_{1-6}$ alkoxyl optionally substituted with —$NR_3R_4$, and piperazinyl optionally substituted with 1-3 $C_{1-4}$ alkyl groups; wherein $R_3$ and $R_4$ are independently selected from H and $C_{1-6}$ alkyl groups; or
the ring including $A_1$-$A_3$, imidazolyl ring and the ring including $B_1$-$B_3$ are fused to form benzo[4,5]imidazo[1,2-a]pyrimidinyl or benzo[4,5]imidazo[1,2-a]pyrazinyl; the ring including $D_1$-$D_4$ is pyridyl; R', R" and R''' are H; $R_1$ is selected from the group consisting of dihydropyranyl, tetrahydropyranyl and morpholinyl; and $R_2$ is selected from the group consisting of $C_{1-6}$ alkoxy substituted by —$NR_3R_4$, wherein, $R_3$ and $R_4$ are independently selected from H and $C_{1-6}$ alkyl; or
the ring including $A_1$-$A_3$, imidazolyl ring and the ring including $B_1$-$B_3$ are fused to form benzo[4,5]imidazo[1,2-b]pyridazinyl, imidazo[1,2-a:4,5-c']dipyridinyl or imidazo[1,2-a:5,4-c']dipyridinyl; the ring including $D_1$-$D_4$ is pyridyl; $R_1$ is selected from dihydropyranyl or morpholinyl; and $R_2$ is selected from $C_{1-6}$ alkoxy optionally substituted by —$NR_3R_4$, wherein $R_3$ and $R_4$ are independently selected from the group consisting of H and $C_{1-6}$ alkyl.

5. The compound of claim 2, wherein the compound is the compound of Formula IIb, or its pharmaceutically acceptable salts, wherein $A_1$-$A_3$ and $B_1$-$B_3$ are all CH; $R_6$ is H, haloalkyl or halo; $R_5$, $R_7$ and $R_8$ are H; $R_1$ is optionally substituted heterocyclic group; $R_2$ is optionally substituted heterocyclic group, or $C_{1-6}$ alkoxy substituted by —$NR_3R_4$; wherein, $R_3$ and $R_4$ are independently H or $C_{1-6}$.

6. The compound of claim 1, wherein said compound is selected from the group consisting of:
- N,N-dimethyl-3-((5-(9-(3,6-dihydro-2H-pyran-4-yl)benzo[4,5]imidazo[1,2-a]pyridin-2-yl)pyridin-2-yl)oxy)propan-1-amine;
- N,N-dimethyl-3-(4-(9-(3,6-dihydro-2H-pyran-4-yl)benzo[4,5]imidazo[1,2-a]pyridin-2-yl)phenoxy)propan-1-amine;
- N,N-dimethyl-3-(4-(9-(4-methylpiperazin-1-yl)benzo[4,5]imidazo[1,2-a]pyridin-2-yl)phenoxy)propan-1-amine;
- N,N-dimethyl-3-(4-(9-morpholinobenzo[4,5]imidazo[1,2-a]pyridin-2-yl)phenoxy)propan-1-amine;
- N,N-dimethyl-3-((5-(9-(piperidin-1-yl)benzo[4,5]imidazo[1,2-a]pyridin-2-yl)pyridin-2-yl)oxy)propan-1-amine;
- N,N-dimethyl-3-((5-(9-morpholinobenzo[4,5]imidazo[1,2-a]pyridin-2-yl)pyridin-2-yl)oxy)propan-1-amine;
- N,N-dimethyl-3-((5-(9-(4-methylpiperazin-1-yl)benzo[4,5]imidazo[1,2-a]pyridin-2-yl)pyridin-2-yl)oxy)propan-1-amine;
- N,N-dimethyl-3-((5-(9-((3S,5R)-3,4,5-trimethylpiperazin-1-yl)benzo[4,5]imidazo[1,2-a]pyridin-2-yl)pyridin-2-yl)oxy)propan-1-amine;
- N,N-dimethyl-3-((5-(9-(1H-imidazol-1-yl)benzo[4,5]imidazo[1,2-a]pyridin-2-yl)pyridin-2-yl)oxy)propan-1-amine;
- N,N-dimethyl-3-((5-(9-(morpholinomethyl)benzo[4,5]imidazo[1,2-a]pyridin-2-yl)pyridin-2-yl)oxy)propan-1-amine;
- N,N-dimethyl-3-((5-(9-((4-methylpiperazin-1-yl)methyl)benzo[4,5]imidazo[1,2-a]pyridin-2-yl)pyridin-2-yl)oxy)propan-1-amine;
- N,N-dimethyl-3-((5-(94(1-methylpiperidin-4-yl)oxy)benzo[4,5]imidazo[1,2-a]pyridin-2-yl)pyridin-2-yl)oxy)propan-1-amine;
- N,N-dimethyl-3-((5-(9-((tetrahydro-2H-pyran-4-yl)oxy)benzo[4,5]imidazo[1,2-a]pyridin-2-yl)pyridin-2-yl)oxy)propan-1-amine;
- N,N-dimethyl-3-((5-(9-(tetrahydro-2H-pyran-4-ylamino)benzo[4,5]imidazo[1,2-a]pyridin-2-yl)pyridin-2-yl)oxy)propan-1-amine;
- N,N-dimethyl-3-((5-(9-(1-methylpiperidin-4-ylamino)benzo[4,5]imidazo[1,2-a]pyridin-2-yl)pyridin-2-yl)oxy)propan-1-amine;
- 1-(6-(4-methylpiperazin-1-yl)pyridin-3-yl)-8-morpholinobenzo[4,5]imidazo[1,2-a]pyridine;
- 1-(6-((3S,5R)-3,4,5-trimethylpiperazin-1-yl)pyridin-3-yl)-8-morpholinobenzo[4,5]imidazo[1,2-a]pyridine;
- N,N-dimethyl-3-((6-(9-(3,6-dihydro-2H-pyran-4-yl)benzo[4,5]imidazo[1,2-a]pyridin-2-yl)pyridin-3-yl)oxy)propan-1-amine;
- 1-(6-(4-methylpiperazin-1-yl)pyridin-3-yl)-8-(3,6-dihydro-2H-pyran-4-yl)benzo[4,5]imidazo[1,2-a]pyridine;
- 1-(6-((3S,5R)-3,4,5-trimethylpiperazin-1-yl)pyridin-3-yl)-8-(3,6-dihydro-2H-pyran-4-yl)benzo[4,5]imidazo[1,2-a]pyridine;
- N,N-dimethyl-3-((5-(9-(tetrahydro-2H-pyran-4-yl)benzo[4,5]imidazo[1,2-a]pyridin-2-yl)pyridin-2-yl)oxy)propan-1-amine;
- N,N-dimethyl-3-((5-(9-(1-methylpiperidin-4-yl)benzo[4,5]imidazo[1,2-a]pyridin-2-yl)pyridin-2-yl)oxy)propan-1-amine;
- N,N-dimethyl-3-((5-(9-(1H-imidazol-4-yl)benzo[4,5]imidazo[1,2-a]pyridin-2-yl)pyridin-2-yl)oxy)propan-1-amine;
- N,N-dimethyl-3-((5-(9-(piperidin-4-yloxy)benzo[4,5]imidazo[1,2-a]pyridin-2-yl)pyridin-2-yl)oxy)propan-1-amine;
- N,N-dimethyl-3-((5-(6-(3,6-dihydro-2H-pyran-4-yl)benzo[4,5]imidazo[1,2-a]pyrimidin-3-yl)pyridin-2-yl)oxy)propan-1-amine;
- N,N-dimethyl-3-((5-(6-(tetrahydro-2H-pyran-4-yl)benzo[4,5]imidazo[1,2-a]pyrimidin-3-yl)pyridin-2-yl)oxy)propan-1-amine;
- N,N-dimethyl-3-((5-(6-morpholinobenzo[4,5]imidazo[1,2-a]pyrimidin-3-yl)pyridin-2-yl)oxy)propan-1-amine;
- N,N-dimethyl-3-((5-(6-(3,6-dihydro-2H-pyran-4-yl)benzo[4,5]imidazo[1,2-a]pyrazin-3-yl)pyridin-2-yl)oxy)propan-1-amine;
- N,N-dimethyl-3-((5-(6-(tetrahydro-2H-pyran-4-yl)benzo[4,5]imidazo[1,2-a]pyrazin-3-yl)pyridin-2-yl)oxy)propan-1-amine;
- N,N-dimethyl-3-((5-(6-morpholinobenzo[4,5]imidazo[1,2-a]pyrazin-3-yl)pyridin-2-yl)oxy)propan-1-amine;
- N,N-dimethyl-3-((5-(9-(3,6-dihydro-2H-pyran-4-yl)benzo[4,5]imidazo[1,2-b]pyridazin-2-yl)pyridin-2-yl)oxy)propan-1-amine;
- N,N-dimethyl-3-((5-(9-morpholinobenzo[4,5]imidazo[1,2-b]pyridazin-2-yl)pyridin-2-yl)oxy)propan-1-amine;
- N,N-dimethyl-3-((5-(4-(3,6-dihydro-2H-pyran-4-yl)imidazo[1,2-a:4,5-b]dipyridin-7-yl)pyridin-2-yl)oxy)propan-1-amine;
- N,N-dimethyl-3-((5-(4-morpholinoimidazo[1,2-a:4,5-b']dipyridin-7-yl)pyridin-2-yl)oxy)propan-1-amine;
- N,N-dimethyl-3-((5-(4-(3,6-dihydro-2H-pyran-4-yl)imidazo[1,2-a:4,5-c]dipyridin-7-yl)pyridin-2-yl)oxy)propan-1-amine;
- N,N-dimethyl-3-((5-(4-morpholinoimidazo[1,2-a:4,5-c']dipyridin-7-yl)pyridin-2-yl)oxy)propan-1-amine;
- N,N-dimethyl-3-((5-(1-(3,6-dihydro-2H-pyran-4-yl)imidazo[1,2-a:5,4-c']dipyridin-8-yl)pyridin-2-yl)oxy)propan-1-amine;
- N,N-dimethyl-3-((5-(1-morpholinoimidazo[1,2-a:5,4-c']dipyridin-8-yl)pyridin-2-yl)oxy)propan-1-amine;
- N,N-dimethyl-1-(4-(9-(3,6-dihydro-2H-pyran-4-yl)benzo[4,5]imidazo[1,2-a]pyridin-2-yl)phenyl)piperidin-4-amine;
- N,N-dimethyl-1-(5-(9-(3,6-dihydro-2H-pyran-4-yl)benzo[4,5]imidazo[1,2-a]pyridin-2-yl)pyridin-2-yl)piperidin-4-amine;
- N,N-dimethyl-1-(4-(9-morpholinobenzo[4,5]imidazo[1,2-a]pyridin-2-yl)phenyl)piperidin-4-amine;
- N,N-dimethyl-1-(5-(9-morpholinobenzo[4,5]imidazo[1,2-a]pyridin-2-yl)piperidin-4-amine;
- N,N-dimethyl-1-(2-(trifluoromethyl)-4-(9-(4-methylpiperazin-1-yl)benzo[4,5]imidazo[1,2-a]pyridin-2-yl)phenyl)piperidin-4-amine;
- N,N-dimethyl-3-(2-(trifluoromethyl-4-(9-(4-methylpiperazin-1-yl)benzo[4,5]imidazo[1,2-a]pyridin-2-yl))phenoxy)propan-1-amine;
- N,N-dimethyl-1-(4-(9-((3S,5R)-3,4,5-trimethylpiperazin-1-yl)benzo[4,5]imidazo[1,2-a]pyridin-2-yl)phenyl)piperidin-4-amine;
- N,N-dimethyl-1-(2-fluoro-4-(9-((3S,5R)-3,4, 5-trimethylpiperazin-1-yl)benzo[4,5]imidazo[1,2-a]pyridin-2-yl)phenyl)piperidin-4-amine;
- N,N-dimethyl-1-(2-chloro-4-(9-((3S,5R)-3,4,5-trimethylpiperazin-1-yl)benzo[4,5]imidazo[1,2-a]pyridin-2-yl)phenyl)piperidin-4-amine;

N,N-dimethyl-1-(2-(trifluoromethyl)-4-(9-((3S,5R)-3,4,5-trimethylpiperazin-1-yl)benzo[4,5]imidazo[1,2-a]pyridin-2-yl)phenyl)piperidin-4-amine;

N,N-dimethyl-3-(4-(9-((3S,5R)-3,4,5-trimethylpiperazin-1-yl)benzo[4,5]imidazo[1,2-a]pyridin-2-yl)phenoxy)propan-1-amine;

N,N-dimethyl-3-(2-fluoro-4-(9-((3S,5R)-3,4,5-trimethylpiperazin-1-yl)benzo[4,5]imidazo[1,2-a]pyridin-2-yl)phenoxy)propan-1-amine;

N,N-dimethyl-3-(2-chloro-4-(9-((3S,5R)-3,4,5-trimethylpiperazin-1-yl)benzo[4,5]imidazo[1,2-a]pyridin-2-yl)phenoxy)propan-1-amine;

N,N-dimethyl-3-(2-bromo-4-(9-((3S,5R)-3,4,5-trimethylpiperazin-1-yl)benzo[4,5]imidazo[1,2-a]pyridin-2-yl)phenoxy)propan-1-amine;

N,N-dimethyl-3-(2-(trifluoromethyl)-4-(9-((3S,5R)-3,4,5-trimethylpiperazin-1-yl)benzo[4,5]imidazo[1,2-a]pyridin-2-yl)phenoxy)propan-1-amine;

N,N-dimethyl-1-(2-(trifluoromethyl)-4-(9-((2S,6R)-2,6-dimethylmorpholino)benzo[4,5]imidazo[1,2-a]pyridin-2-yl)phenyl)piperidin-4-amine;

N,N-dimethyl-3-(2-(trifluoromethyl)-4-(9-((2S,6R)-2,6-dimethylmorpholino)benzo[4,5]imidazo[1,2-a]pyridin-2-yl)phenoxy)propan-1-amine;

N,N-dimethyl-1-(4-(9-(4-(dimethylamino)piperidin-1-yl)benzo[4,5]imidazo[1,2-a]pyridin-2-yl)phenyl)piperidin-4-amine;

N,N-dimethyl-1-(2-(3-fluoro-4-(4-(dimethylamino)piperidin-1-yl)phenyl)benzo[4,5]imidazo[1,2-a]pyridin-9-yl)piperidin-4-amine;

N,N-dimethyl-1-(2-(3-chloro-4-(4-(dimethylamino)piperidin-1-yl)phenyl)benzo[4,5]imidazo[1,2-a]pyridin-9-yl)piperidin-4-amine;

N,N-dimethyl-1-(2-(3-bromo-4-(4-(dimethylamino)piperidin-1-yl)phenyl)benzo[4,5]imidazo[1,2-a]pyridin-9-yl)piperidin-4-amine;

N,N-dimethyl-1-(2-(3-(trifluoromethyl)-4-(4-(dimethylamino)piperidin-1-yl)phenyl)benzo[4,5]imidazo[1,2-a]pyridin-9-yl)piperidin-4-amine;

N,N-dimethyl-1-(2-(3-(trifluoromethyl)-4-(4-(methylamino)piperidin-1-yl)phenyl)benzo[4,5]imidazo[1,2-a]pyridin-9-yl)piperidin-4-amine;

N,N-dimethyl-1-(2-(3-(trifluoromethyl)-4-(4-(ethylamino)piperidin-1-yl)phenyl)benzo[4,5]imidazo[1,2-a]pyridin-9-yl)piperidin-4-amine;

N,N-dimethyl-1-(2-(6-(3-(dimethylamino)propoxy)pyridin-3-yl)benzo[4,5]imidazo[1,2-a]pyridin-9-yl)piperidin-4-amine;

N,N-dimethyl-1-(2-(4-(3-(dimethylamino)propoxy)phenyl)benzo[4,5]imidazo[1,2-a]pyridin-9-yl)piperidin-4-amine;

N,N-dimethyl-1-(2-(3-fluoro-4-(3-(dimethylamino)propoxy)phenyl)benzo[4,5]imidazo[1,2-a]pyridin-9-yl)piperidin-4-amine;

N,N-dimethyl-1-(2-(3-chloro-4-(3-(dimethylamino)propoxy)phenyl)benzo[4,5]imidazo[1,2-a]pyridin-9-yl)piperidin-4-amine;

N,N-dimethyl-1-(2-(3-bromo-4-(3-(dimethylamino)propoxy)phenyl)benzo[4,5]imidazo[1,2-a]pyridin-9-yl)piperidin-4-amine;

N,N-dimethyl-1-(2-(3-(trifluoromethyl)-4-(3-(dimethylamino)propoxy)phenyl)benzo[4,5]imidazo[1,2-a]pyridin-9-yl)piperidin-4-amine;

N,N-dimethyl-1-(2-(trifluoromethyl)-4-(9-((1-methylpiperidin-4-yl)oxy)benzo[4,5]imidazo[1,2-a]pyridin-2-yl)phenyl)piperidin-4-amine;

N,N-dimethyl-3-(2-(trifluoromethyl)-4-(9-((1-methylpiperidin-4-yl)oxy)benzo[4,5]imidazo[1,2-a]pyridin-2-yl)phenoxy)propan-1-amine;

N,N-dimethyl-1-(4-(4-((3S,5R)-3,4,5-trimethylpiperazin-1-yl)pyridazino[6,1-f]purin-7-yl)phenyl)piperidin-4-amine;

and pharmaceutically acceptable salts thereof.

7. A method of treating a disease caused by DDR functional defects or benefiting from the inhibition of ATM kinase activity, comprising administering to a subject in need thereof an effective amount of the compound of claim 1 or a pharmaceutically acceptable salt thereof, or a pharmaceutical composition comprising the compound of claim 1 or a pharmaceutically acceptable salt thereof.

8. The compound of claim 1, wherein each of $A_1$-$A_3$ is CR'; each of $B_1$-$B_3$ is CR''; and each of R', R'', and R''' is H.

9. The compound of claim 2, wherein $R_5$-$R_8$ are each independently H, halo, or haloalkyl.

10. The compound of claim 3, wherein the ring including $A_1$-$A_3$, imidazolyl ring and the ring including $B_1$-$B_3$ are fused to form benzo[4,5]imidazo[1,2-a]pyridinyl, benzo[4,5]imidazo[1,2-a]pyrimidinyl, benzo[4,5]imidazo[1,2-a]pyrazinyl, benzo[4,5]imidazo[1,2-b]pyridazinyl, imidazo[1,2-a:4,5-b']dipyridinyl, imidazo[1,2-a:4,5-c']dipyridinyl or imidazo[1,2-a:5,4c']dipyridinyl.

11. The method of claim 7, wherein the disease is cancer.

12. The method of claim 11, wherein the cancer is selected from liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoide, head and neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, or prostatic carcinoma.

13. The method of claim 12, further comprising administering at least one known anticancer drug, or its pharmaceutically acceptable salts.

14. The method of claim 13, wherein the known anticancer drug is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, methylhydroxy ellipticine, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, mAb, panitumumab, ofatumumab, avastin, trastuzumab, rituximab, imatinib, gefitinib, erlotinib, lapatinib, sorafinib, sunitinib, nilotinib, dasatinib, pazopanib, torisel, everolimus, vorinostat, romidepsin, tamoxifen, letrozole, fulvestrant, mitoguazone, octreotide, retinoic acid, arsenic trioxide, zoledronic acid, bortezomib, thalidomide, lenalidomide, venetoclax, aldesleukin (recombinant human interleukin-2), sipueucel-T, palbociclib, olaparib, niraparib, rucaparib and talazoparib.

15. The method of claim 7, wherein the compound or a pharmaceutically acceptable salt thereof or the pharmaceutical composition is used in combination with radiotherapy.

16. A pharmaceutical composition comprising a compound of claim 1 or a pharmaceutically acceptable salt thereof and a pharmaceutically acceptable carrier.

17. The pharmaceutical composition of claim 16, wherein the pharmaceutical composition further comprises at least one known anticancer drug, or its pharmaceutically acceptable salts.

18. The pharmaceutical composition of claim 17, wherein the known anticancer drug is selected from the group consisting of: busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, methylhydroxy ellipticine, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, mAb, panitumumab, ofatumumab, avastin, trastuzumab, rituximab, imatinib, gefitinib, erlotinib, lapatinib, sorafinib, sunitinib, nilotinib, dasatinib, pazopanib, torisel, everolimus, vorinostat, romidepsin, tamoxifen, letrozole, fulvestrant, mitoguazone, octreotide, retinoic acid, arsenic trioxide, zoledronic acid, bortezomib, thalidomide, lenalidomide, venetoclax, aldesleukin (recombinant human interleukin-2), sipueucel-T, palbociclib, olaparib, niraparib, rucaparib and talazoparib.

19. The composition of claim 16, wherein in the compound,
the ring including $A_1$-$A_3$, imidazolyl ring and the ring including $B_1$-$B_3$ are fused to form benzo[4,5]imidazo [1,2-a]pyridinyl; the ring including $D_1$-$D_4$ is pyridyl or phenyl; R', R" and R'" are H; $R_1$ is selected from the group consisting of dihydropyranyl; tetrahydropyranyl; piperidyl that is not substituted or optionally substituted with 1-4 $C_{1-6}$ alkyl or —$NR_3R_4$ groups; morpholinyl; imidazolyl; piperazinyl that is optionally substituted with 1-4 $C_{1-6}$ alkyl groups; and a $C_{1-6}$ alkyl or amino or oxy group that is optionally substituted with morpholinyl, piperazinyl optionally substituted by 1-3 $C_{1-6}$ alkyl, piperidyl optionally substituted with 1-3 $C_{1-6}$ alkyl or tetrahydropyranyl; $R_2$ is selected from the group consisting of $C_{1-6}$ alkoxyl optionally substituted with —$NR_3R_4$, and piperazinyl optionally substituted with 1-3 $C_{1-4}$ alkyl groups; wherein $R_3$ and $R_4$ are independently selected from H and $C_{1-6}$ alkyl groups; or
the ring including $A_1$-$A_3$, imidazolyl ring and the ring including $B_1$-$B_3$ are fused to form benzo[4,5]imidazo [1,2-a]pyrimidinyl or benzo[4,5]imidazo[1,2-a]pyrazinyl; the ring including $D_1$-$D_4$ is pyridyl; R', R" and R'" are H; $R_1$ is selected from the group consisting of dihydropyranyl, tetrahydropyranyl and morpholinyl; and $R_2$ is selected from the group consisting of $C_{1-6}$ alkoxy substituted by —$NR_3R_4$, wherein, $R_3$ and $R_4$ are independently selected from H and $C_{1-6}$ alkyl; or
the ring including $A_1$-$A_3$, imidazolyl ring and the ring including $B_1$-$B_3$ are fused to form benzo[4,5]imidazo [1,2-b]pyridazinyl, imidazo[1,2-a:4,5-c']dipyridinyl or imidazo[1,2-a:5,4-c']dipyridinyl; the ring including $D_1$-$D_4$ is pyridyl; $R_1$ is selected from dihydropyranyl or morpholinyl; and $R_2$ is selected from $C_{1-6}$ alkoxy optionally substituted by —$NR_3R_4$, wherein, $R_3$ and $R_4$ are independently selected from the group consisting of H and $C_{1-6}$ alkyl.

20. The composition of claim 16, wherein the compound is selected from the group consisting of:
N,N-dimethyl-3-((5-(9-(3,6-dihydro-2H-pyran-4-yl) benzo[4,5]imidazo[1,2-a]pyridin-2-yl)pyridin-2-yl) oxy)propan-1-amine;
N,N-dimethyl-3-(4-(9-(3,6-dihydro-2H-pyran-4-yl)benzo [4,5]imidazo[1,2-a]pyridin-2-yl)phenoxy)propan-1-amine;
N,N-dimethyl-3-(4-(9-(4-methylpiperazin-1-yl)benzo[4,5]imidazo[1,2-a]pyridin-2-yl)phenoxy)propan-1-amine;
N,N-dimethyl-3-(4-(9-morpholinobenzo[4,5]imidazo[1,2-a]pyridin-2-yl)phenoxy)propan-1-amine;
N,N-dimethyl-3-((5-(9-(piperidin-1-yl)benzo[4,5]imidazo[1,2-a]pyridin-2-yl)pyridin-2-yl)oxy)propan-1-amine;
N,N-dimethyl-3-((5-(9-morpholinobenzo[4,5]imidazo[1,2-a]pyridin-2-yl)pyridin-2-yl)oxy)propan-1-amine;
N,N-dimethyl-3-((5-(9-(4-methylpiperazin-1-yl)benzo[4,5]imidazo[1,2-a]pyridin-2-yl)pyridin-2-yl)oxy)propan-1-amine;
N,N-dimethyl-3-((5-(9-((3S,5R)-3,4,5-trimethylpiperazin-1-yl)benzo[4,5]imidazo[1,2-a]pyridin-2-yl)pyridin-2-yl)oxy)propan-1-amine;
N,N-dimethyl-3-((5-(9-(1H-imidazol-1-yl)benzo[4,5] imidazo[1,2-a]pyridin-2-yl)pyridin-2-yl)oxy)propan-1-amine;
N,N-dimethyl-3-((5-(9-(morpholinomethyl)benzo[4,5] imidazo[1,2-a]pyridin-2-yl)pyridin-2-yl)oxy)propan-1-amine;
N,N-dimethyl-3-((5-(9-(4-methylpiperazin-1-yl)methyl) benzo[4,5]imidazo[1,2-a]pyridin-2-yl)pyridin-2-yl) oxy)propan-1-amine;
N,N-dimethyl-3-((5-(9-((1-methylpiperidin-4-yl)oxy) benzo[4,5]imidazo[1,2-a]pyridin-2-yl)pyridin-2-yl) oxy)propan-1-amine;
N,N-dimethyl-3-((5-(9-((tetrahydro-2H-pyran-4-yl)oxy) benzo[4,5]imidazo[1,2-a]pyridin-2-yl)pyridin-2-yl) oxy)propan-1-amine;
N,N-dimethyl-3-((5-(9-(tetrahydro-2H-pyran-4-ylamino) benzo[4,5]imidazo[1,2-a]pyridin-2-yl)pyridin-2-yl) oxy)propan-1-amine;
N,N-dimethyl-3-((5-(9-(1-methylpiperidin-4-ylamino) benzo[4,5]imidazo[1,2-a]pyridin-2-yl)pyridin-2-yl) oxy)propan-1-amine;
1-(6-(4-methylpiperazin-1-yl)pyridin-3-yl)-8-morpholinobenzo[4,5]imidazo[1,2-a]pyridine;
1-(6-((3S,5R)-3,4,5-trimethylpiperazin-1-yl)pyridin-3-yl)-8-morpholinobenzo[4,5]imidazo[1,2-a]pyridine;
N,N-dimethyl-3-((6-(9-(3,6-dihydro-2H-pyran-4-yl) benzo[4,5]imidazo[1,2-a]pyridin-2-yl)pyridin-3-yl) oxy)propan-1-amine;
1-(6-(4-methylpiperazin-1-yl)pyridin-3-yl)-8-(3,6-dihydro-2H-pyran-4-yl)benzo[4,5]imidazo[1,2-a]pyridine;
1-(6-((3S,5R)-3,4,5-trimethylpiperazin-1-yl)pyridin-3-yl)-8-(3,6-dihydro-2H-pyran-4-yl)benzo[4,5]imidazo [1,2-a]pyridine;
N,N-dimethyl-3-((5-(9-(tetrahydro-2H-pyran-4-yl)benzo [4,5]imidazo[1,2-a]pyridin-2-yl)pyridin-2-yl)oxy)propan-1-amine;
N,N-dimethyl-3-((5-(9-(1-methylpiperidin-4-yl)benzo[4,5]imidazo[1,2-a]pyridin-2-yl)pyridin-2-yl)oxy)propan-1-amine;

N,N-dimethyl-3-((5-(9-(1H-imidazol-4-yl)benzo[4,5]
  imidazo[1,2-a]pyridin-2-yl)pyridin-2-yl)oxy)propan-
  1-amine;
N,N-dimethyl-3-((5-(9-(piperidin-4-yloxy)benzo[4,5]
  imidazo[1,2-a]pyridin-2-yl)pyridin-2-yl)oxy)propan-
  1-amine;
N,N-dimethyl-3-((5-(6-(3,6-dihydro-2H-pyran-4-yl)
  benzo[4,5]imidazo[1,2-a]pyrimidin-3-yl)pyridin-2-yl)
  oxy)propan-1-amine;
N,N-dimethyl-3-((5-(6-(tetrahydro-2H-pyran-4-yl)benzo
  [4,5]imidazo[1,2-a]pyrimidin-3-yl)pyridin-2-yl)oxy)
  propan-1-amine;
N,N-dimethyl-3-((5-(6-morpholinobenzo[4,5]imidazo[1,
  2-a]pyrimidin-3-yl)pyridin-2-yl)oxy)propan-1-amine;
N,N-dimethyl-3-((5-(6-(3,6-dihydro-2H-pyran-4-yl)
  benzo[4,5]imidazo[1,2-a]pyrazin-3-yl)pyridin-2-yl)
  oxy)propan-1-amine;
N,N-dimethyl-3-((5-(6-(tetrahydro-2H-pyran-4-yl)benzo
  [4,5]imidazo[1,2-a]pyrazin-3-yl)pyridin-2-yl)oxy)pro-
  pan-1-amine;
N,N-dimethyl-3-((5-(6-morpholinobenzo[4,5]imidazo[1,
  2-a]pyrazin-3-yl)pyridin-2-yl)oxy)propan-1-amine;
N,N-dimethyl-3-((5-(9-(3,6-dihydro-2H-pyran-4-yl)
  benzo[4,5]imidazo[1,2-b]pyridazin-2-yl)pyridin-2-yl)
  oxy)propan-1-amine;
N,N-dimethyl-3-((5-(9-morpholinobenzo[4,5]imidazo[1,
  2-b]pyridazin-2-yl)pyridin-2-yl)oxy)propan-1-amine;
N,N-dimethyl-3-((5-(4-(3,6-dihydro-2H-pyran-4-yl)imi-
  dazo[1,2-a:4,5-b']dipyridin-7-yl)pyridin-2-yl)oxy)pro-
  pan-1-amine;
N,N-dimethyl-3-((5-(4-morpholinoimidazo[1,2-a:4,5-b']
  dipyridin-7-yl)pyridin-2-yl)oxy)propan-1-amine;
N,N-dimethyl-3-((5-(4-(3,6-dihydro-2H-pyran-4-yl)imi-
  dazo[1,2-a:4,5-c']dipyridin-7-yl)pyridin-2-yl)oxy)pro-
  pan-1-amine;
N,N-dimethyl-3-((5-(4-morpholinoimidazo[1,2-a:4,5-c']
  dipyridin-7-yl)pyridin-2-yl)oxy)propan-1-amine;
N,N-dimethyl-3-((5-(1-(3,6-dihydro-2H-pyran-4-yl)imi-
  dazo[1,2-a: 5,4-c']dipyridin-8-yl)pyridin-2-yl)oxy)pro-
  pan-1-amine;
N,N-dimethyl-3-((5-(1-morpholinoimidazo[1,2-a: 5,4-c']
  dipyridin-8-yl)pyridin-2-yl)oxy)propan-1-amine;
N,N-dimethyl-1-(4-(9-(3,6-dihydro-2H-pyran-4-yl)benzo
  [4,5]imidazo[1,2-a]pyridin-2-yl)phenyl)piperidin-4-
  amine;
N,N-dimethyl-1-(5-(9-(3,6-dihydro-2H-pyran-4-yl)benzo
  [4,5]imidazo[1,2-a]pyridin-2-yl)pyridin-2-yl)piperi-
  din-4-amine;
N,N-dimethyl-1-(4-(9-morpholinobenzo[4,5]imidazo[1,
  2-a]pyridin-2-yl)phenyl)piperidin-4-amine;
N,N-dimethyl-1-(5-(9-morpholinobenzo[4,5]imidazo[1,
  2-a]pyridin-2-yl)pyridin-2-yl)piperidin-4-amine;
N,N-dimethyl-1-(2-(trifluoromethyl)-4-(9-(4-methylpip-
  erazin-1-yl)benzo[4,5]imidazo[1,2-a]pyridin-2-yl)phe-
  nyl)piperidin-4-amine;
N,N-dimethyl-3-(2-(trifluoromethyl-4-(9-(4-methylpiper-
  azin-1-yl)benzo[4,5]imidazo[1,2-a]pyridin-2-yl))phe-
  noxy)propan-1-amine;
N,N-dimethyl-1-(4-(9-((3S,5R)-3,4,5-trimethylpiperazin-
  1-yl)benzo[4,5]imidazo[1,2-a]pyridin-2-yl)phenyl)pip-
  eridin-4-amine;
N,N-dimethyl-1-(2-fluoro-4-(9-((3S,5R)-3,4, 5-trimeth-
  ylpiperazin-1-yl)benzo[4,5]imidazo[1,2-a]pyridin-2-
  yl)phenyl)piperidin-4-amine;
N,N-dimethyl-1-(2-chloro-4-(9-((3S,5R)-3,4,5-trimeth-
  ylpiperazin-1-yl)benzo[4,5]imidazo[1,2-a]pyridin-2-
  yl)phenyl)piperidin-4-amine;
N,N-dimethyl-1-(2-(trifluoromethyl)-4-(9-(3S,5R)-3,4,5-
  trimethylpiperazin-1-yl)benzo[4,5]imidazo[1,2-a]pyri-
  din-2-yl)phenyl)piperidin-4-amine;
N,N-dimethyl-3-(4-(9-((3S,5R)-3,4,5-trimethylpiperazin-
  1-yl)benzo[4,5]imidazo[1,2-a]pyridin-2-yl)phenoxy)
  propan-1-amine;
N,N-dimethyl-3-(2-fluoro-4-(9-((3S,5R)-3,4, 5-trimeth-
  ylpiperazin-1-yl)benzo[4,5]imidazo[1,2-a]pyridin-2-
  yl)phenoxy)propan-1-amine;
N,N-dimethyl-3-(2-chloro-4-(9-((3S,5R)-3,4,5-trimeth-
  ylpiperazin-1-yl)benzo[4,5]imidazo[1,2-a]pyridin-2-
  yl)phenoxy)propan-1-amine;
N,N-dimethyl-3-(2-bromo-4-(9-((3S,5R)-3,4,5-trimeth-
  ylpiperazin-1-yl)benzo[4,5]imidazo[1,2-a]pyridin-2-
  yl)phenoxy)propan-1-amine;
N,N-dimethyl-3-(2-(trifluoromethyl)-4-(9-((3S,5R)-3,4,
  5-trimethylpiperazin-1-yl)benzo[4,5]imidazo[1,2-a]
  pyridin-2-yl)phenoxy)propan-1-amine;
N,N-dimethyl-1-(2-(trifluoromethyl)-4-(9-((2S,6R)-2,6-
  dimethylmorpholino)benzo[4,5]imidazo[1,2-a]pyridin-
  2-yl)phenyl)piperidin-4-amine;
N,N-dimethyl-3-(2-(trifluoromethyl)-4-(9-((2S,6R)-2,6-
  dimethylmorpholino)benzo[4,5]imidazo[1,2-a]pyridin-
  2-yl)phenoxy)propan-1-amine;
N,N-dimethyl-1-(4-(9-(4-(dimethylamino)piperidin-1-yl)
  benzo[4,5]imidazo[1,2-a]pyridin-2-yl)phenyl)piperi-
  din-4-amine;
N,N-dimethyl-1-(2-(3-fluoro-4-(4-(dimethylamino)pip-
  eridin-1-yl)phenyl)benzo[4,5]imidazo[1,2-a]pyridin-9-
  yl)piperidin-4-amine;
N,N-dimethyl-1-(2-(3-chloro-4-(4-(dimethylamino)pip-
  eridin-1-yl)phenyl)benzo[4,5]imidazo[1,2-a]pyridin-9-
  yl)piperidin-4-amine;
N,N-dimethyl-1-(2-(3-bromo-4-(4-(dimethylamino)pip-
  eridin-1-yl)phenyl)benzo[4,5]imidazo[1,2-a]pyridin-9-
  yl)piperidin-4-amine;
N,N-dimethyl-1-(2-(3-(trifluoromethyl)-4-(4-(dimethyl-
  amino)piperidin-1-yl)phenyl)benzo[4,5]imidazo[1,2-a]
  pyridin-9-yl)piperidin-4-amine;
N,N-dimethyl-1-(2-(3-(trifluoromethyl)-4-(4-(methyl-
  amino)piperidin-1-yl)phenyl)benzo[4,5]imidazo[1,2-a]
  pyridin-9-yl)piperidin-4-amine;
N,N-dimethyl-1-(2-(3-(trifluoromethyl)-4-(4-(ethyl
  amino)piperidin-1-yl)phenyl)benzo[4,5]imidazo[1,2-a]
  pyridin-9-yl)piperidin-4-amine;
N,N-dimethyl-1-(2-(6-(3-(dimethylamino)propoxy)pyri-
  din-3-yl)benzo[4,5]imidazo[1,2-a]pyridin-9-yl)piperi-
  din-4-amine;
N,N-dimethyl-1-(2-(4-(3-(dimethylamino)propoxy)phe-
  nyl)benzo[4,5]imidazo[1,2-a]pyridin-9-yl)piperidin-4-
  amine;
N,N-dimethyl-1-(2-(3-fluoro-4-(3-(dimethylamino)
  propoxy)phenyl)benzo[4,5]imidazo[1,2-a]pyridin-9-
  yl)piperidin-4-amine;
N,N-dimethyl-1-(2-(3-chloro-4-(3-(dimethylamino)
  propoxy)phenyl)benzo[4,5]imidazo[1,2-a]pyridin-9-
  yl)piperidin-4-amine;
N,N-dimethyl-1-(2-(3-bromo-4-(3-(dimethylamino)
  propoxy)phenyl)benzo[4,5]imidazo[1,2-a]pyridin-9-
  yl)piperidin-4-amine;
N,N-dimethyl-1-(2-(3-(trifluoromethyl)-4-(3-(dimethyl-
  amino)propoxy)phenyl)benzo[4,5]imidazo[1,2-a]pyri-
  din-9-yl)piperidin-4-amine;
N,N-dimethyl-1-(2-(trifluoromethyl)-4-(9-((1-methylpip-
  eridin-4-yl)oxy)benzo[4,5]imidazo[1,2-a]pyridin-2-yl)
  phenyl)piperidin-4-amine;

N,N-dimethyl-3-(2-(trifluoromethyl)-4-(9-((1-methylpiperidin-4-yl)oxy)benzo[4,5]imidazo[1,2-a]pyridin-2-yl)phenoxy)propan-1-amine; and N,N-dimethyl-1-(4-(4-((3S,5R)-3,4,5-trimethylpiperazin-1-yl)pyridazino[6,1-f]purin-7-yl)phenyl)piperidin-4-amine.

\* \* \* \* \*